(12) United States Patent
Kamiyama et al.

(10) Patent No.: US 7,410,981 B2
(45) Date of Patent: Aug. 12, 2008

(54) PRODRUGS OF IMIDAZOLE DERIVATIVES, FOR USE AS PROTON PUMP INHIBITORS IN THE TREATMENT OF E.G. PEPTIC ULCERS

(75) Inventors: Keiji Kamiyama, Ibaraki (JP); Hiroshi Banno, Kawanishi (JP); Fumihiko Sato, Suita (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 330 days.

(21) Appl. No.: 10/517,633

(22) PCT Filed: Jun. 13, 2003

(86) PCT No.: PCT/JP03/07546

§ 371 (c)(1),
(2), (4) Date: Dec. 13, 2004

(87) PCT Pub. No.: WO03/105845

PCT Pub. Date: Dec. 24, 2003

(65) Prior Publication Data

US 2005/0222210 A1    Oct. 6, 2005

(30) Foreign Application Priority Data

Jun. 14, 2002  (JP)  ............... 2002-175086
Feb. 19, 2003  (JP)  ............... 2003-041085

(51) Int. Cl.
*A61K 31/4439* (2006.01)
*C07D 401/12* (2006.01)
(52) U.S. Cl. .................. 514/338; 546/273.7
(58) Field of Classification Search .......... 546/273.7; 514/338
See application file for complete search history.

(56) References Cited

U.S. PATENT DOCUMENTS

| | | | |
|---|---|---|---|
| 4,045,563 A | 8/1977 | Berntsson et al. | 424/263 |
| 4,686,230 A | 8/1987 | Rainer et al. | 514/338 |
| 4,873,337 A | 10/1989 | Sih et al. | 546/271 |
| 4,965,269 A | 10/1990 | Brandstrom et al. | 514/253 |
| 5,021,433 A | 6/1991 | Alminger et al. | 514/338 |
| 5,039,806 A | 8/1991 | Brandstram et al. | 546/271 |
| 6,093,734 A | 7/2000 | Garst | 514/338 |

FOREIGN PATENT DOCUMENTS

| | | |
|---|---|---|
| EP | 1 334 971 | 8/2003 |
| EP | 1 437 352 | 7/2004 |

*Primary Examiner*—Patricia L Morris
(74) *Attorney, Agent, or Firm*—Wenderoth, Lind & Ponack, LLP

(57) ABSTRACT

An imidazole compound represented by the formula (I), a salt thereof and a compound of the formula (V), which is one of the intermediates thereof. wherein each symbol is as defined in the present specification. The compound of the present invention shows a superior anti-ulcer activity, a gastric acid secretion inhibitory action, a mucosa-protecting action, an anti-Helicobacter pylori action and the like. Since it shows low toxicity, the compound is useful as a pharmaceutical product.

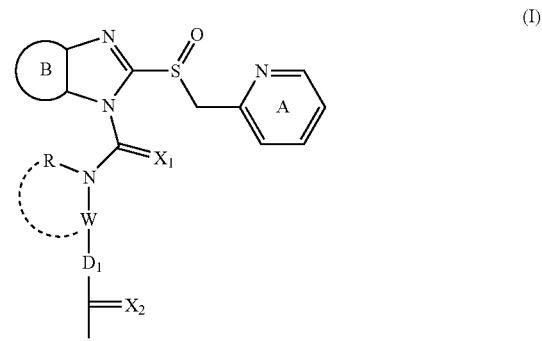

(I)

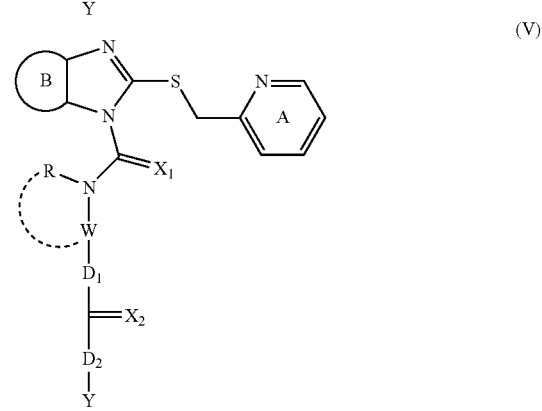

(V)

13 Claims, No Drawings

PRODRUGS OF IMIDAZOLE DERIVATIVES, FOR USE AS PROTON PUMP INHIBITORS IN THE TREATMENT OF E.G. PEPTIC ULCERS

This application is a U.S. national stage of International Application No. PCT/JP03/07546 filed Jun. 13, 2003.

TECHNICAL FIELD

The present invention relates to an imidazole compound, which is converted to a proton pump inhibitor in living organisms and shows an anti-ulcer activity and the like, a production method thereof and use thereof.

BACKGROUND ART

There are known variously substituted 2-(pyridylmethylsulfinyl)-1H-benzimidazole derivatives and structurally related sulfoxides, that inhibit the proton pump and show anti-ulcer activity and the like. For example, a compound having a general name lansoprazole, 2-[[[3-methyl-4-(2,2,2-trifluoroethoxy)-2-pyridyl]methyl]sulfinyl]-1H-benzimidazole, and a salt thereof are reported in JP-A-61-50978 and the like. In addition, a compound having a general name, omeprazole (5-methoxy-2-[[(4-methoxy-3,5-dimethyl-2-pyridyl)-methyl]sulfinyl]-1H-benzimidazole) and a salt thereof are described in JP-A-54-141783 and the like, a compound having a general name, pantoprazole (5-difluoromethoxy-2-[[(3,4-dimethoxy-2-pyridyl)-methyl]sulfinyl]-1H-benzimidazole) and a salt thereof are described in JP-A-61-22079 and the like, a compound having a general name, rabeprazole (2-[[[4-(3-methoxypropoxy)-3-methyl-2-pyridyl]methyl]sulfinyl]-1H-benzimidazole) and a salt thereof are described in JP-A-1-6270 and the like, and a compound having a general name, tenatoprazole (5-methoxy-2-[[(4-methoxy-3,5-dimethyl-2-pyridyl)methyl]sulfinyl]imidazo[4,5-b]pyridine) and a salt thereof are described in JP-A-63-146882 and the like.

However, since the above-mentioned compounds are unstable to acids, for oral administration, they are formulated into an enteric-coated preparation, filled in a capsule and administered, or filled in an enteric capsule and administered, or formulated into an enteric tablet and administered, thereby to prevent decomposition by gastric acid.

Therefore, the development of a prodrug of the above-mentioned compound, which is stable to acid and which resists decomposition by gastric acid, has been desired, and such prodrug has been reported in U.S. Pat. No. 6,093,734. In addition, prodrugs of proton pump inhibitors other than the above-mentioned prodrug have been disclosed in U.S. Pat. Nos. 4,045,563, 4,686,230, 4,873,337, 4,965,269, 5,021,433, 5,039,806 and the like.

In view of the above situation, the development of a prodrug of a proton pump inhibitor having superior stability to acid has been desired.

It is therefore an object of the present invention to provide a compound having superior stability to acid, which is converted to a proton pump inhibitor in living organisms and shows an anti-ulcer activity and the like, an intermediate therefor, a production method thereof and use thereof.

DISCLOSURE OF THE INVENTION

The present inventors have first synthesized a compound represented by the following formula (I) and first found that this compound has unexpectedly superior stability to acid, gradually eliminates the substituent on the nitrogen atom of benzimidazole ring and affords a sustained acid secretion-suppressive action. Further studies based on these findings have resulted in the completion of the present invention.

According to the present invention, variously substituted 2-(pyridylmethylsulfinyl)-1H-benzimidazole derivatives and structurally related sulfoxides are modified to give a prodrug (the compound of the formula (I)) stable to acid, which enables oral administration of the compound as a conventional tablet and the like without formulating an enteric-coated preparation. This has a consequence that the cost for formulating an enteric-coated preparation can be eliminated and the preparation of tablet and the like can be made smaller. A smaller preparation is advantageous in that it is easily swallowed by patients having difficulty in swallowing, particularly the elderly and children. In addition, absorption is rapid due to the absence of a sustained release effect afforded by enteric-coated preparations, expression of a gastric acid secretion-suppressive action is rapid, and alleviation of symptoms such as pain and the like is rapid. Furthermore, because the compound is gradually converted to a proton pump inhibitor in living organisms, a sustainable anti-ulcer agent and the like can be provided.

Accordingly, the present invention provides the following.

[1] An imidazole compound represented by the formula (I):

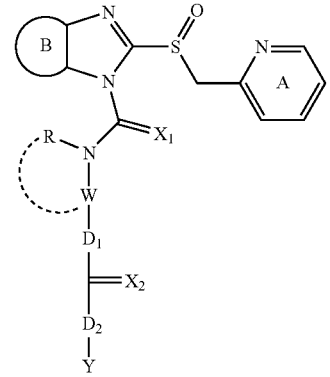

(I)

wherein ring A is a pyridine ring optionally having substituents, ring B is a benzene ring optionally having substituents or a monocyclic aromatic heterocycle optionally having substituents, $X_1$ and $X_2$ are each an oxygen atom or a sulfur atom, W is a divalent chain hydrocarbon group optionally having substituents or a divalent group represented by the formula:

—$W_1$-Z-$W_2$— wherein $W_1$ and $W_2$ are each a divalent chain hydrocarbon group or a bond, Z is a divalent hydrocarbon ring group optionally having substituents, a divalent heterocyclic group optionally having substituents, an oxygen atom, $SO_n$ wherein n is 0, 1 or 2, or >N-E wherein E is a hydrogen atom, a hydrocarbon group optionally having substituents, a heterocyclic group optionally having substituents, a lower alkanoyl group, a lower alkoxycarbonyl group, an aralkyloxycarbonyl group, a thiocarbamoyl group, a lower alkylsulfinyl group, a lower alkylsulfonyl group, a sulfamoyl group, a mono-lower alkylsulfamoyl group, a di-lower alkylsulfamoyl group, an arylsulfamoyl group, an arylsulfinyl group, an arylsulfonyl group, an arylcarbonyl group or a carbamoyl group optionally having substituents, and when Z is an oxygen atom, SO$_n$ or >N-E, W$_1$ and W$_2$ are each a divalent chain hydrocarbon group, R is a hydrocarbon group optionally having substituents or a heterocyclic group optionally having substituents, R and W may be bonded to each other, D$_1$ and D$_2$ are each a bond, an oxygen atom, a sulfur atom or >NR$_1$ wherein R$_1$ is a hydrogen atom or a hydrocarbon group optionally having substituents, except for when D$_1$ and D$_2$ are each a bond, and Y is a hydrocarbon group optionally having substituents or a heterocyclic group optionally having substituents, or a salt thereof.

[2] The compound of the above-mentioned [1], wherein Z is a divalent hydrocarbon ring group optionally having substituents or a divalent heterocyclic group optionally having substituents.

[3] The compound of the above-mentioned [1], wherein ring B is a benzene ring optionally having substituents.

[4] The compound of the above-mentioned [1], which is represented by the formula (II):

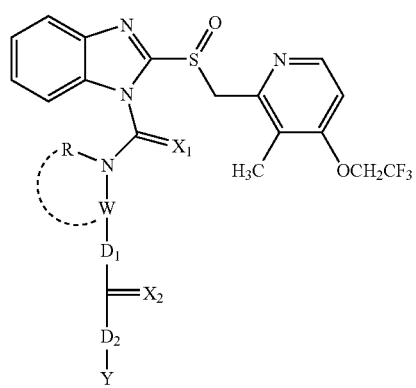

(II)

wherein each symbol in the formula is as defined in the above-mentioned [1].

[5] The compound of any of the above-mentioned [1] to [4], wherein X$_1$ and X$_2$ are each an oxygen atom.

[6] The compound of the above-mentioned [1], wherein D$_1$ and D$_2$ are each a bond or an oxygen atom, except for when D$_1$ and D$_2$ are each a bond.

[7] The compound of the above-mentioned [1], wherein W is a divalent chain hydrocarbon group optionally having substituents.

[8] The compound of the above-mentioned [1], wherein W is an ethylene group.

[9] The compound of the above-mentioned [1], wherein R is a C$_{1-6}$ hydrocarbon group optionally having substituents.

[10] The compound of the above-mentioned [1], wherein Y is a C$_{1-6}$ hydrocarbon group optionally having substituents or a saturated heterocyclic group optionally having substituents, which contains, as ring-constituting atom, 1 to 4 heteroatom(s) selected from oxygen atom, nitrogen atom and sulfur atom.

[11] The compound of the above-mentioned [1], wherein X$_1$ and X$_2$ are each an oxygen atom, D$_1$ and D$_2$ are each a bond or an oxygen atom except for when D$_1$ and D$_2$ are both a bond, W is an ethylene group, R is a C$_{1-6}$ alkyl group, and Y is a C$_{1-6}$ hydrocarbon group optionally having substituents or a saturated oxygen-containing heterocyclic group optionally having substituents, which may further contain, as ring-constituting atom, 1 to 3 heteroatom(s) selected from oxygen atom, nitrogen atom and sulfur atom.

[12] The compound of the above-mentioned [1], which is a compound selected from

2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate, ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate, 2-[methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate, ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate, ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate, 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl acetate, 2-[methyl[[2-[[[3-methyl-4-(2,2,2-trifluoroethoxy)-2-pyridyl]methyl]sulfinyl]-1H-benzimidazol-1-yl]carbonyl]amino]ethyl acetate, ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate, ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate, ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate, and 2-[[[5-(difluoromethoxy)-2-[[(3,4-dimethoxy-2-pyridyl)methyl]sulfinyl]-1H-benzimidazol-1-yl]carbonyl](methyl)amino]ethyl ethyl carbonate or a salt thereof.

[13] A compound represented by the formula (V):

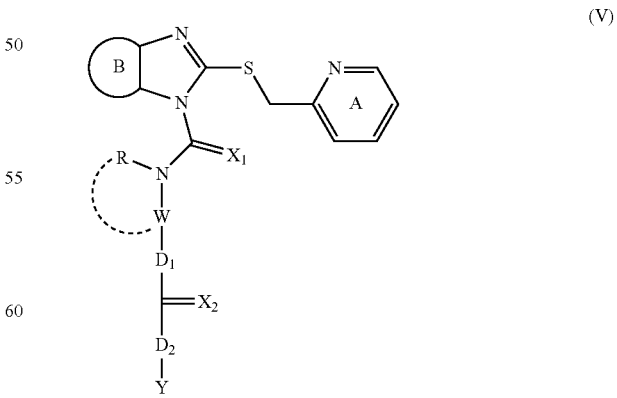

(V)

wherein ring A is a pyridine ring optionally having substituents, ring B is a benzene ring optionally having substituents or a monocyclic aromatic heterocycle optionally having substituents, $X_1$ and $X_2$ are each an oxygen atom or a sulfur atom, W is a divalent chain hydrocarbon group optionally having substituents or a divalent group represented by the formula:

—$W_1$-Z-$W_2$— wherein $W_1$ and $W_2$ are each a divalent chain hydrocarbon group or a bond, Z is a divalent hydrocarbon ring group optionally having substituents; a divalent heterocyclic group optionally having substituents, an oxygen atom, $SO_n$ wherein n is 0, 1 or 2, or >N-E wherein E is a hydrogen atom, a hydrocarbon group optionally having substituents, a heterocyclic group optionally having substituents, a lower alkanoyl group, a lower alkoxycarbonyl group, an aralkyloxycarbonyl group, a thiocarbamoyl group, a lower alkylsulfinyl group, a lower alkylsulfonyl group, a sulfamoyl group, a mono-lower alkylsulfamoyl group, a di-lower alkylsulfamoyl group, an arylsulfamoyl group, an arylsulfinyl group, an arylsulfonyl group, an arylcarbonyl group or a carbamoyl group optionally having substituents, and when Z is an oxygen atom, $SO_n$ or >N-E, $W_1$ and $W_2$ are each a divalent chain hydrocarbon group, R is a hydrocarbon group optionally having substituents or a heterocyclic group optionally having substituents, R and W may be bonded to each other, $D_1$ and $D_2$ are each a bond, an oxygen atom, a sulfur atom or >$NR_1$ wherein $R_1$ is a hydrogen atom or a hydrocarbon group optionally having substituents, except for when $D_1$ and $D_2$ are each a bond, and Y is a hydrocarbon group optionally having substituents or a heterocyclic group optionally having substituents, or a salt thereof.

[14] A production method of a compound of the above-mentioned [1], which comprises:

(1) condensing a compound represented by the formula (III):

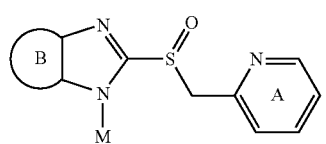

(III)

wherein ring A is a pyridine ring optionally having substituents, ring B is a benzene ring optionally having substituents or a monocyclic aromatic heterocycle optionally having substituents and M is a hydrogen atom, a metal cation or a quaternary ammonium ion, or a salt thereof, with a compound represented by the formula (IV):

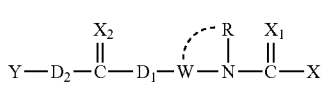

(IV)

wherein

X is a leaving group, $X_1$ and $X_2$ are each an oxygen atom or a sulfur atom,

W is a divalent chain hydrocarbon group optionally having substituents, or a divalent group of the formula:

—$W_1$-Z-$W_2$— wherein $W_1$ and $W_2$ are each a divalent chain hydrocarbon group or a bond, Z is a divalent hydrocarbon ring group optionally having substituents, a divalent heterocyclic group optionally having substituents, an oxygen atom, $SO_n$ wherein n is 0, 1 or 2, or >N-E wherein E is a hydrogen atom, a hydrocarbon group optionally having substituents, a heterocyclic group optionally having substituents, a lower alkanoyl group, a lower alkoxycarbonyl group, an aralkyloxycarbonyl group, a thiocarbamoyl group, a lower alkylsulfinyl group, a lower alkylsulfonyl group, a sulfamoyl group, a mono-lower alkylsulfamoyl group, a di-lower alkylsulfamoyl group, an arylsulfamoyl group, an arylsulfinyl group, an arylsulfonyl group, an arylcarbonyl group or a carbamoyl group optionally having substituents, and when Z is an oxygen atom, $SO_n$ or >N-E, $W_1$ and $W_2$ are each a divalent chain hydrocarbon group, R is a hydrocarbon group optionally having substituents or a heterocyclic group optionally having substituents, R and W may be bonded to each other, $D_1$ and $D_2$ are each a bond, an oxygen atom, a sulfur atom, or >$NR_1$ wherein $R_1$ is a hydrogen atom or a hydrocarbon group optionally having substituents, except for when $D_1$ and $D_2$ are each a bond, and Y is a hydrocarbon group optionally having substituents or a heterocyclic group optionally having substituents, or a salt thereof, or (2) subjecting a compound represented by the formula (V):

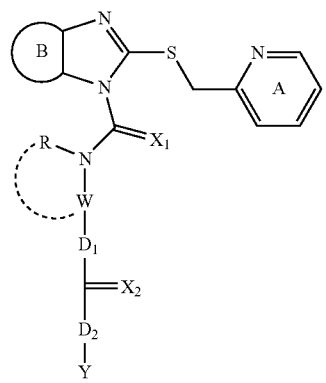

(V)

wherein each symbol in the formula is as defined above, or a salt thereof, to an oxidization reaction.

[15] A pharmaceutical composition comprising a compound of the above-mentioned [1].

[16] The pharmaceutical composition of the above-mentioned [15], which is an agent for the prophylaxis or treatment of peptic ulcer, gastritis, peptic esophagitis, symptomatic gastroesophageal reflux disease (symptomatic GERD) free of esophagitis, NUD, gastric cancer, gastric MALT lymphoma, Zollinger-Ellison syndrome, acid indigestion or upper gastrointestinal hemorrhage.

[17] A commercial package comprising a pharmaceutical composition of the above-mentioned [16] and written matter associated therewith, the written matter stating that the pharmaceutical composition can or should be used for the prophylaxis or treatment of peptic ulcer, gastritis, peptic esophagitis, symptomatic gastroesophageal reflux disease (symptomatic GERD) free of esophagitis, NUD, gastric cancer, gastric MALT lymphoma, Zollinger-Ellison syndrome, acid indigestion or upper gastrointestinal hemorrhage.

[18] The pharmaceutical composition of the above-mentioned [15], which is an agent for the eradication of *Helicobacter pylori*.

[19] A commercial package comprising a pharmaceutical composition of the above-mentioned [18] and written matter associated therewith, the written matter stating that the pharmaceutical composition can or should be used for the eradication of *Helicobacter pylori*.

[20] A method for the prophylaxis or treatment of peptic ulcer, gastritis, peptic esophagitis, symptomatic gastroesophageal reflux disease (symptomatic GERD) free of esophagitis, NUD, gastric cancer, gastric MALT lymphoma, Zollinger-Ellison syndrome, acid indigestion or upper gastrointestinal hemorrhage, which comprises administering an effective amount of a compound of the above-mentioned [1] to an animal.

[21] A method for eradicating *Helicobacter pylori* from an animal infected with *Helicobacter pylori*, which comprises administering an effective amount of a compound of the above-mentioned [1] to an animal.

[22] Use of a compound of the above-mentioned [1] for the production of a prophylactic or therapeutic agent of peptic ulcer, gastritis, peptic esophagitis, symptomatic gastroesophageal reflux disease (symptomatic GERD) free of esophagitis, NUD, gastric cancer, gastric MALT lymphoma, Zollinger-Ellison syndrome, acid indigestion or upper gastrointestinal hemorrhage.

[23] Use of a compound of the above-mentioned [1] for the production of an agent for eradicating *Helicobacter pylori*.

[24] The pharmaceutical composition of the above-mentioned [15], further comprising at least one antibacterial agent in combination with the compound of the above-mentioned [1], wherein active components are formulated altogether in a fixed formulation, or formulated independently for concurrent administration or administration at staggered times to a single subject.

In the present invention, ring A designates a "pyridine ring optionally having substituents".

The pyridine ring of the "pyridine ring optionally having substituents" represented by ring A optionally has 1 to 4 substituents at substitutable positions thereof. As the substituent, for example, a halogen atom (e.g., fluorine, chlorine, bromine, iodine etc.), a hydrocarbon group optionally having substituents (e.g., alkyl group having 1 to 6 carbon atoms such as methyl group, ethyl group, n-propyl group etc., and the like), an amino group optionally having substituents (e.g., amino; amino group mono- or di-substituted by alkyl group having 1 to 6 carbon atoms, such as methylamino, dimethylamino, ethylamino, diethylamino group etc., and the like), an amide group (e.g., $C_{1-3}$ acylamino group such as formamide, acetamide etc., and the like), a lower alkoxy group optionally having substituents (e.g., alkoxy group having 1 to 6 carbon atoms such as methoxy, ethoxy, 2,2,2-trifluoroethoxy, 3-methoxypropoxy group and the like), a lower alkylenedioxy group (e.g., $C_{1-3}$ alkylenedioxy group such as methylenedioxy, ethylenedioxy etc., and the like) and the like can be mentioned.

As the substituent, which is the substituent of the "pyridine ring optionally having substituents" represented by ring A can have, for example, a halogen atom (e.g., fluorine, chlorine, bromine, iodine etc.), a lower alkyl group (e.g., alkyl group having 1 to 6 carbon atoms such as methyl, ethyl, propyl group and the like), a lower alkenyl group (e.g., alkenyl group having 2 to 6 carbon atoms such as vinyl, allyl group and the like), a lower alkynyl group (e.g., alkynyl group having 2 to 6 carbon atoms such as ethynyl, propargyl group and the like), a cycloalkyl group (e.g., cycloalkyl group having 3 to 8 carbon atoms such as cyclopropyl, cyclobutyl, cyclopentyl, cyclohexyl group and the like), a lower alkoxy group (e.g., alkoxy group having 1 to 6 carbon atoms such as methoxy, ethoxy group and the like), a nitro group, a cyano group, a hydroxy group, a thiol group, a carboxyl group, a lower alkanoyl group (e.g., formyl; $C_1$-$C_6$ alkyl-carbonyl group, such as acetyl, propionyl, butyryl group and the like), a lower alkanoyloxy group (e.g., formyloxy; $C_1$-$C_6$ alkyl-carbonyloxy group, such as acetyloxy, propionyloxy group and the like), a lower alkoxycarbonyl group (e.g., $C_1$-$C_6$ alkoxy-carbonyl group, such as methoxycarbonyl, ethoxycarbonyl, propoxycarbonyl group and the like), an aralkyloxycarbonyl group (e.g., $C_{7-11}$ aralkyloxy-carbonyl group, such as benzyloxycarbonyl group and the like), an aryl group (e.g., aryl group having 6 to 14 carbon atoms such as phenyl, naphthyl group and the like), an aryloxy group (e.g., aryloxy group having 6 to 14 carbon atoms such as phenyloxy, naphthyloxy group and the like), an arylcarbonyl group (e.g., $C_6$-$C_{14}$ aryl-carbonyl group, such as benzoyl, naphthoyl group and the like), an arylcarbonyloxy group (e.g., $C_6$-$C_{14}$ aryl-carbonyloxy group, such as benzoyloxy, naphthoyloxy group and the like), a carbamoyl group optionally having substituents (e.g., carbamoyl; carbamoyl group mono- or di-substituted by alkyl group having 1 to 6 carbon atoms, such as methylcarbamoyl, dimethylcarbamoyl group etc., and the like), an amino group optionally having substituents (e.g., amino; amino group mono- or di-substituted by alkyl group having 1 to 6 carbon atoms, such as methylamino, dimethylamino, ethylamino, diethylamino group etc., and the like) and the like, can be mentioned, wherein the number of substituents and the position of the substitution are not particularly limited.

While the number of substituents and the position of substitution of the "pyridine ring optionally having substituents" represented by ring A are not particularly limited, 1 to 3 substituents mentioned above preferably substitute any of the 3-, 4- and 5-positions of the pyridine ring.

As the "pyridine ring optionally having substituents" represented by ring A, 3-methyl-4-(2,2,2-trifluoroethoxy)-2-pyridyl is preferable.

In the present invention, ring B represents a "benzene ring optionally having substituents" or an "aromatic monocyclic heterocycle optionally having substituents", which is condensed with an imidazole part. Of these, the former is preferable.

The benzene ring of the "benzene ring optionally having substituents" represented by ring B may have 1 to 4 substituents at substitutable positions thereof. As the substituent, for example, a halogen atom (e.g., fluorine, chlorine, bromine, iodine etc.), a hydrocarbon group optionally having substituents (e.g., alkyl group having 1 to 6 carbon atoms selected from methyl group, ethyl group, n-propyl group etc., and the like), an amino group optionally having substituents (e.g., amino; amino group mono- or di-substituted by alkyl group having 1 to 6 carbon atoms, such as methylamino, dimethylamino, ethylamino, diethylamino group etc., and the like), an amide group (e.g., $C_{1-3}$ acylamino group such as formamide, acetamide etc., and the like), a lower alkoxy group optionally having substituents (e.g., alkoxy group having 1 to 6 carbon atoms, such as methoxy, ethoxy, difluoromethoxy group etc., and the like), a lower alkylenedioxy group (e.g., $C_{1-3}$ alkylenedioxy group such as methylenedioxy, ethylenedioxy etc., and the like), and the like can be mentioned.

As the substituent, which is the substituent of the "benzene ring optionally having substituents" represented by ring B can have, for example, a halogen atom (e.g., fluorine, chlorine, bromine, iodine etc.), a lower alkyl group (e.g., alkyl group having 1 to 6 carbon atoms such as methyl, ethyl, propyl group and the like), a lower alkenyl group (e.g., alkenyl group having 2 to 6 carbon atoms such as vinyl, allyl group and the like), a lower alkynyl group (e.g., alkynyl group having 2 to 6 carbon atoms such as ethynyl, propargyl group and the like), a cycloalkyl group (e.g., cycloalkyl group having 3 to 8 carbon atoms such as cyclopropyl, cyclobutyl, cyclopentyl, cyclohexyl group and the like), a lower alkoxy group (e.g., alkoxy group having 1 to 6 carbon atoms such as methoxy, ethoxy group and the like), a nitro group, a cyano group, a hydroxy group, a thiol group, a carboxyl group, a lower alkanoyl group (e.g., formyl; $C_{1-6}$ alkyl-carbonyl group, such as acetyl, propionyl, butyryl group and the like), a lower alkanoyloxy group (e.g., formyloxy; $C_{1-6}$ alkyl-carbonyloxy group, such as acetyloxy, propionyloxy group and the like), a lower alkoxycarbonyl group (e.g., $C_{1-6}$ alkoxycarbonyl group, such as methoxycarbonyl, ethoxycarbonyl, propoxycarbonyl group and the like), an aralkyloxycarbonyl group (e.g., $C_{7-17}$ aralkyloxy-carbonyl group, such as benzyloxycarbonyl group and the like), an aryl group (e.g., aryl group having 6 to 14 carbon atoms such as phenyl, naphthyl group and the like), an aryloxy group (e.g., aryloxy group having 6 to 14 carbon atoms such as phenyloxy, naphthyloxy group and the like), an arylcarbonyl group (e.g., $C_{6-14}$ arylcarbonyl group, such as benzoyl, naphthoyl group and the like), an arylcarbonyloxy group (e.g., $C_{6-14}$ aryl-carbonyloxy group, such as benzoyloxy, naphthoyloxy group and the like), a carbamoyl group optionally having substituents (e.g., carbamoyl; carbamoyl group mono- or di-substituted by alkyl group having 1 to 6 carbon atoms such as methylcarbamoyl, dimethylcarbamoyl group etc., and the like), an amino group optionally having substituents (e.g., amino; amino group mono- or di-substituted by alkyl group having 1 to 6 carbon atoms such as methylamino, dimethylamino, ethylamino, diethylamino group etc., and the like) and the like can be mentioned, wherein the number of substituents and the position of the substitution are not particularly limited.

As the "benzene ring optionally having substituents" represented by ring B, a benzene ring is preferable.

As the "aromatic monocyclic heterocycle" of the "aromatic monocyclic heterocycle optionally having substituents" represented by ring B, for example, a 5- or 6-membered aromatic monocyclic heterocycle such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetraxole, pyridine, pyridazine, pyrimidine, pyrazine, triazine etc., and the like can be mentioned. As the "aromatic monocyclic heterocycle" represented by ring B, a pyridine ring is particularly preferable. It may have, at substitutable positions thereof, 1 to 4 substituents similar to those for the "benzene ring optionally having substituents" represented by ring B.

The position where the "aromatic monocyclic heterocycle" of the "aromatic monocyclic heterocycle optionally having substituents" is condensed with the imidazole part is not particularly limited.

In the present invention, $X_1$ and $X_2$ represent an oxygen atom and a sulfur atom, respectively. Both $X_1$ and $X_2$ preferably represent an oxygen atom.

In the present invention, W represents a "divalent chain hydrocarbon group optionally having substituents", or the formula:

$$—W_1\text{-}Z\text{-}W_2—$$

wherein $W_1$ and $W_2$ are each a "divalent chain hydrocarbon group" or a bond, and Z is a divalent group such as a "divalent hydrocarbon ring group optionally having substituents", a "divalent heterocyclic group optionally having substituents", an oxygen atom, $SO_n$ wherein n is 0, 1 or 2 or >N-E wherein E is a hydrogen atom, a hydrocarbon group optionally having substituents, a heterocyclic group optionally having substituents, a lower alkanoyl group, a lower alkoxycarbonyl group, an aralkyloxycarbonyl group, a thiocarbamoyl group, a lower alkylsulfinyl group, a lower alkylsulfonyl group, a sulfamoyl group, a mono-lower alkylsulfamoyl group, a di-lower alkylsulfamoyl group, an arylsulfamoyl group, an arylsulfinyl group, an arylsulfonyl group, an arylcarbonyl group, or a carbamoyl group optionally having substituents, when Z is an oxygen atom, $SO_n$ or >N-E, $W_1$ and $W_2$ are each a "divalent chain hydrocarbon group". Particularly, W is preferably a "divalent chain hydrocarbon group optionally having substituents".

As the "divalent chain hydrocarbon group" of the "divalent chain hydrocarbon group optionally having substituents" represented by W and "divalent chain hydrocarbon group" represented by $W_1$ and $W_2$, for example, a $C_{1-6}$ alkylene group (e.g., methylene, ethylene, trimethylene etc.), a $C_{2-6}$ alkenylene group (e.g., ethenylene etc.), a $C_{2-6}$ alkynylene group (e.g., ethynylene etc.) and the like can be mentioned. The divalent chain hydrocarbon group for W may have 1 to 6 substituents similar to those for the "benzene ring optionally having substituents" represented by ring B at substitutable positions thereof.

As the "divalent chain hydrocarbon group" of the "divalent chain hydrocarbon group optionally having substituents" represented by W and "divalent chain hydrocarbon group" represented by $W_1$ and $W_2$, a methylene group and an ethylene group are preferable. As W, an ethylene group is particularly preferable. When Z is an oxygen atom, $SO_n$ or >N-E (n and E are as defined above), the "divalent chain hydrocarbon group" represented by $W_1$ is preferably a hydrocarbon group having 2 or more carbon atoms.

As the "hydrocarbon ring" of the "divalent hydrocarbon ring group optionally having substituents" represented by Z, for example, an alicyclic hydrocarbon ring, an aromatic hydrocarbon ring and the like can be mentioned, with preference given to one having 3 to 16 carbon atoms, which may have 1 to 4 substituents similar to those for the "benzene ring optionally having substituents" represented by ring B at substitutable positions thereof. As the hydrocarbon ring, for example, cycloalkane, cycloalkene, arene and the like are used.

As a cycloalkane in the "divalent hydrocarbon ring group optionally having substituents" represented by Z, for example, a lower cycloalkane and the like are preferable, and, for example, $C_{3-10}$ cycloalkane such as cyclopropane, cyclobutane, cyclopentane, cyclohexane, cycloheptane, cyclooctane, bicyclo[2.2.1]heptane, adamantane etc., and the like are generally used.

As a cycloalkene in the "divalent hydrocarbon ring group optionally having substituents" represented by Z, for example, a lower cycloalkene is preferable, and, for example, $C_{4-9}$ cycloalkene such as cyclopropene, cyclobutene, cyclopentene, cyclohexene, cycloheptene, cyclooctene etc., and the like are generally used.

As an arene in the "divalent hydrocarbon ring group optionally having substituents" represented by Z, for example, a $C_{6-14}$ arene such as benzene, naphthalene, phenanthrene etc., and the like are preferable, and, for example, phenylene and the like are generally used.

As a heterocycle in the "divalent heterocyclic group optionally having substituents" represented by Z, a 5- to 12-membered "aromatic heterocycle" or "saturated or unsaturated non-aromatic heterocycle" containing, as ring-constituting atom (ring atom), 1 to 3 (preferably 1 or 2) kinds of at least 1 (preferably 1 to 4, more preferably 1 or 2) hetero atoms selected from oxygen atom, sulfur atom and nitrogen atom etc., and the like can be mentioned, which may have 1 to 4 substituents similar to those for the "benzene ring optionally having substituents" represented by ring B at substitutable positions thereof.

As an aromatic heterocycle in the "divalent heterocyclic group optionally having substituents" represented by Z, an aromatic monocyclic heterocycle, an aromatic fused heterocycle and the like can be mentioned.

As the "aromatic monocyclic heterocycle", for example, a 5- or 6-membered aromatic monocyclic heterocycle such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine etc., and the like can be mentioned.

As the "aromatic fused heterocycle", for example, a 8- to 12-membered aromatic fused heterocycle such as benzofuran, isobenzofuran, benzothiophene, isobenzothiophene, indole, isoindole, 1H-indazole, benzimidazole, benzoxazole, 1,2-benzisoxazole, benzothiazole, 1,2-benzisothiazole, 1H-benzotriazole, quinoline, isoquinoline, cinnoline, quinazoline, quinoxaline, phthalazine, naphthyridine, purine, pteridine, carbazole, carboline, acridine, phenoxazine, phenothiazine, phenazine, phenoxathiin, thianthrene, phenanthridine, phenanthroline, indolizine, pyrrolo[1,2-b]pyridazine, pyrazolo[1,5-a]pyridine, imidazo[1,2-a]pyridine, imidazo[1,5-a]pyridine, imidazo[1,2-b]pyridazine, imidazo[1,2-a]pyrimidine, 1,2,4-triazolo[4,3-a]pyridine, 1,2,4-triazolo[4,3-b]pyridazine etc., and the like can be mentioned.

As a saturated or unsaturated non-aromatic heterocycle in the "divalent heterocyclic group optionally having substituents" represented by Z, for example, a 3- to 8-membered (preferably 5- or 6-membered) saturated or unsaturated (preferably saturated) non-aromatic heterocycle (aliphatic heterocycle) such as oxylane, azetidine, oxetane, thietane, pyrrolidine, tetrahydrofuran, tetrahydrothiophene, piperidine, tetrahydropyran, tetrahydrothiopyran, morpholine, thiomorpholine, piperazine, azepane, oxepane, thiene, oxazepane, thiazepane, azocane, oxocane, thiocane, oxazocane, thiazocane etc., and the like can be mentioned. These may be oxo-substituted and may be, for example, 2-oxoazetidine, 2-oxopyrrolidine, 2-oxopiperidine, 2-oxazepane, 2-oxazocane, 2-oxotetrahydrofuran, 2-oxotetrahydropyran, 2-oxotetrahydrothiophene, 2-oxothiane, 2-oxopiperazine, 2-oxooxepane, 2-oxooxazepane, 2-oxothiepane, 2-oxothiazepane, 2-oxooxocane, 2-oxothiocane, 2-oxooxazocane, 2-oxothiazocane and the like.

The two bonds from the "hydrocarbon ring group" of the "divalent hydrocarbon ring group optionally having substituents" or the "heterocyclic group" of the "divalent heterocyclic group optionally having substituents" represented by Z may be present at any possible position.

The "hydrocarbon group optionally having substituents" and "heterocyclic group optionally having substituents" represented by E is as defined in the following.

As the "lower alkanoyl group" represented by E, for example, formyl, a $C_{1-6}$ alkyl-carbonyl group such as acetyl, propionyl, butyryl, isobutyryl etc., and the like can be used.

As the "lower alkoxycarbonyl group" represented by E, for example, a $C_{1-6}$ alkoxy-carbonyl group such as methoxycarbonyl, ethoxycarbonyl, propoxycarbonyl, butoxycarbonyl etc., and the like are used.

As the "aralkyloxycarbonyl" represented by E, for example, a $C_{7-11}$ aralkyloxy-carbonyl group such as benzyloxycarbonyl etc., and the like are used.

As the "lower alkylsulfinyl group" represented by E, for example, a $C_{1-6}$ alkylsulfinyl group such as methylsulfinyl, ethylsulfinyl etc., and the like are used.

As the "lower alkylsulfonyl group" represented by E, for example, a $C_{1-6}$ alkylsulfonyl group such as methylsulfonyl, ethylsulfonyl etc., and the like are used.

As the "mono-lower alkylsulfamoyl group" represented by E, for example, a mono-$C_{1-6}$ alkylsulfamoyl group such as methylsulfamoyl, ethylsulfamoyl etc., and the like are used.

As the "di-lower alkylsulfamoyl group" represented by E, for example, a di-$C_{1-6}$ alkylsulfamoyl group such as dimethylsulfamoyl, diethylsulfamoyl etc., and the like are used.

As the "arylsulfamoyl group" represented by E, for example, a $C_{6-10}$ arylsulfamoyl group such as phenylsulfamoyl, naphthylsulfamoyl etc., and the like are used.

As the "arylsulfinyl group" represented by E, for example, a $C_{6-10}$ arylsulfinyl group such as phenylsulfinyl, naphthylsulfinyl etc., and the like are used.

As the "arylsulfonyl group" represented by E, for example, a $C_{6-10}$ arylsulfonyl group such as phenylsulfonyl, naphthylsulfonyl etc., and the like are used.

As the "arylcarbonyl group" represented by E, for example, $C_{6-10}$ aryl-carbonyl group such as benzoyl, naphthoyl etc., and the like are used.

The "carbamoyl group optionally having substituents" represented by E is, for example, a group of the formula —$CONR_2R_3$ wherein $R_2$ and $R_3$ are each a hydrogen atom, a hydrocarbon group optionally having substituents or a heterocyclic group optionally having substituents, and in the formula —$CONR_2R_3$, $R_2$ and $R_3$ may form a ring together with the adjacent nitrogen atom, and the like.

In the present invention, R is a "hydrocarbon group optionally having substituents" or a "heterocyclic group optionally having substituents", and R can be bonded to W. Of these, a $C_{1-6}$ hydrocarbon group optionally having substituents is preferable and a lower ($C_{1-6}$) alkyl group is particularly preferable. The "hydrocarbon group optionally having substituents" and "heterocyclic group optionally having substituents" represented by R are as defined in the following. A detailed explanation of the case where R is bonded to W is given in the following.

In the present invention, $D_1$ and $D_2$ are each a bond, an oxygen atom, a sulfur atom or >$NR_1$, and in the formula, $R_1$ is a hydrogen atom or a hydrocarbon group optionally having substituents. However, the present invention excludes a case where $D_1$ and $D_2$ are both respectively a bond. Among others, each of $D_1$ and $D_2$ is preferably a bond or an oxygen atom, and particularly preferably, $D_1$ is an oxygen atom and $D_2$ is an oxygen atom or a bond. The "hydrocarbon group optionally having substituents" represented by $R_1$ is as defined in the following.

In the present invention, Y is a "hydrocarbon group optionally having substituents" or a "heterocyclic group optionally having substituents". Of these, a $C_{1-6}$ hydrocarbon group optionally having substituents or a saturated heterocyclic group optionally having substituents, which contains, as ring-constituting atom, 1 to 4 hetero atoms selected from oxygen atom, sulfur atom and nitrogen atom is preferable. As Y, among others, a $C_{1-6}$ hydrocarbon group optionally having substituents or a saturated oxygen-containing heterocyclic group optionally having substituents, which further contains, as ring-constituting atom, 1 to 3 hetero atoms selected from oxygen atom, sulfur atom and nitrogen atom is preferable. The "hydrocarbon group optionally having substituents" and "heterocyclic group optionally having substituents" represented by Y are as defined in the following.

As the "hydrocarbon group" of the "hydrocarbon group optionally having substituents" represented by the above-mentioned E, R, $R_1$ and Y, for example, a saturated or unsaturated aliphatic hydrocarbon group, a saturated or unsaturated alicyclic hydrocarbon group, a saturated or unsaturated alicyclic-aliphatic hydrocarbon group, an aromatic hydrocarbon group, an aromatic-saturated or unsaturated alicyclic hydrocarbon group and the like can be mentioned, with preference given to those having 1 to 16, more preferably 1 to 6, carbon atoms. Specific examples thereof include alkyl group, alkenyl group, alkynyl group, cycloalkyl group, cycloalkenyl group, cycloalkylalkyl group, cycloalkenylalkyl group, aryl group and arylalkyl group and the like.

For example, the "alkyl group" is preferably a lower alkyl group ($C_{1-6}$ alkyl group) and the like, and, for example, a $C_{1-6}$ alkyl group such as methyl, ethyl, propyl, isopropyl, butyl, isobutyl, sec-butyl, tert-butyl, pentyl, 1-ethylpropyl, hexyl etc., and the like are generally used. For R, a lower alkyl group ($C_{1-6}$ alkyl group) is preferable, particularly a methyl group is preferable.

For example, the "alkenyl group" is preferably a lower alkenyl group and the like, and, for example, a $C_{2-7}$ alkenyl group such as vinyl, 1-propenyl, allyl, isopropenyl, butenyl, isobutenyl, 2,2-dimethyl-pent-4-enyl etc., and the like are generally used.

For example, the "alkynyl group" is preferably a lower alkynyl group and the like, and, for example, a $C_{2-6}$ alkynyl group such as ethynyl, propargyl, 1-propynyl etc., and the like are generally used.

For example, the "cycloalkyl group" is preferably a lower cycloalkyl group and the like, and, for example, a $C_{3-10}$ cycloalkyl group such as cyclopropyl, cyclobutyl, cyclopentyl, cyclohexyl, cycloheptyl, cyclooctyl, bicyclo[2.2.1]heptanyl and adamantyl etc., and the like are generally used.

For example, the "cycloalkenyl group" is preferably a lower cycloalkenyl group, and, for example, a $C_{3-10}$ cycloalkenyl group such as cyclopropenyl, cyclobutenyl, cyclopentenyl, cyclohexenyl, cycloheptenyl, cyclooctenyl, bicyclo[2.2.1]hept-5-en-2-yl etc., and the like are generally used.

For example, the "cycloalkylalkyl group" is preferably a lower cycloalkylalkyl group, and, for example, a $C_{4-9}$ cycloalkylalkyl group such as cyclopropylmethyl, cyclopropylethyl, cyclobutylmethyl, cyclopentylmethyl, cyclohexylmethyl and cyclohexylethyl etc., and the like are generally used.

For example, the "cycloalkenylalkyl group" is preferably a lower cycloalkenylalkyl group, and, for example, $C_{4-9}$ cycloalkenylalkyl such as cyclopentenylmethyl, cyclohexenylmethyl, cyclohexenylethyl, cyclohexenylpropyl, cycloheptenylmethyl, cycloheptenylethyl and bicyclo[2.2.1]hept-5-en-2-ylmethyl etc., and the like are generally used.

For example, the "aryl group" is preferably a $C_{6-14}$ aryl group such as phenyl, 1-naphthyl, 2-naphthyl, biphenylyl, 2-anthryl etc., and the like, and, for example, phenyl group and the like are generally used.

The "arylalkyl group" contains, as the aryl moiety, the "aryl group" defined above, and as the alkyl moiety, the "alkyl group" defined above. Of these, for example, a $C_{6-14}$ aryl-$C_{1-6}$ alkyl group is preferable, and, for example, benzyl, phenethyl and the like are generally used.

As the substituent that the "hydrocarbon group" of the "hydrocarbon group optionally having substituents" represented by the above-mentioned E, R, $R_1$ and Y may have, for example, a halogen atom (e.g., fluorine, chlorine, bromine, iodine etc.), a nitro group, a cyano group, a hydroxy group, a thiol group, a sulfo group, a sulphino group, a phosphono group, an optionally halogenated lower alkyl group (e.g., $C_{1-6}$ alkyl such as methyl, ethyl, propyl, isopropyl, butyl, isobutyl, sec-butyl, tert-butyl, pentyl, 1-ethylpropyl, hexyl and the like, a mono-, di- or tri-halogeno-$C_{1-6}$ alkyl group such as chloromethyl, dichloromethyl, trichloromethyl, fluoromethyl, difluoromethyl, trifluoromethyl, 2-bromoethyl, 2,2,2-trifluoroethyl, pentafluoroethyl, 3,3,3-trifluoropropyl, 4,4,4-trifluorobutyl, 5,5,5-trifluoropentyl, 6,6,6-trifluorohexyl etc., and the like), an oxo group, an amidino group, an imino group, an alkylenedioxy group (e.g., $C_{1-3}$ alkylenedioxy group such as methylenedioxy, ethylenedioxy etc., and the like), a lower alkoxy group (e.g., $C_{1-6}$ alkoxy group such as methoxy, ethoxy, propoxy, isopropoxy, butoxy, isobutoxy, pentyloxy, hexyloxy etc., and the like), an optionally halogenated lower alkoxy group (e.g., a mono-, di- or tri-halogeno-$C_{1-6}$ alkoxy group such as chloromethyloxy, dichloromethyloxy, trichloromethyloxy, fluoromethyloxy, difluoromethyloxy, trifluoromethyloxy, 2-bromoethyloxy, 2,2,2-trifluoroethyloxy, pentafluoroethyloxy, 3,3,3-trifluoropropyloxy, 4,4,4-trifluorobutyloxy, 5,5,5-trifluoropentyloxy, 6,6,6-trifluorohexyloxy etc., and the like), a lower alkylthio group (e.g., a $C_{1-6}$ alkylthio group such as methylthio, ethylthio, propylthio, isopropylthio, butylthio, isobutylthio, pentylthio, hexylthio etc., and the like), a carboxyl group, a lower alkanoyl group (e.g., formyl; a $C_{1-6}$ alkyl-carbonyl group such as acetyl, propionyl, butyryl, isobutyryl etc., and the like), a lower alkanoyloxy group (e.g., formyloxy; a $C_{1-6}$ alkyl-carbonyloxy group such as acetyloxy, propionyloxy, butyryloxy, isobutyryloxy etc., and the like), a lower alkoxy-carbonyl group (e.g., a $C_{1-6}$ alkoxy-carbonyl group such as methoxycarbonyl, ethoxycarbonyl, propoxycarbonyl, butoxycarbonyl etc., and the like), aralkyloxycarbonyl group (e.g., a $C_{7-11}$ aralkyloxy-carbonyl group such as benzyloxycarbonyl etc., and the like), a thiocarbamoyl group, a lower alkylsulfinyl group (e.g., a $C_{1-6}$ alkylsulfinyl group such as methylsulfinyl, ethylsulfinyl etc., and the like), a lower alkylsulfonyl group (e.g., a $C_{1-6}$ alkylsulfonyl group such as methylsulfonyl, ethylsulfonyl etc., and the like), a sulfamoyl group, a mono-lower alkylsulfamoyl group (e.g., a mono-$C_{1-6}$ alkylsulfamoyl group such as methylsulfamoyl, ethylsulfamoyl etc., and the like), di-lower alkylsulfamoyl group (e.g., a di-$C_{1-6}$ alkylsulfamoyl group such as dimethylsulfamoyl, diethylsulfamoyl etc., and the like), an arylsulfamoyl group (e.g., a $C_{6-10}$ arylsulfamoyl group such as phenylsulfamoyl, naphthylsulfamoyl etc., and the like), an aryl group (e.g., a $C_{6-10}$ aryl group such as phenyl, naphthyl etc., and the like), an aryloxy group (e.g., a $C_{6-10}$ aryloxy group such as phenyloxy, naphthyloxy etc., and the like), an arylthio group (e.g., a $C_{6-10}$ arylthio group such as phenylthio, naphthylthio etc., and the like), an arylsulfinyl group (e.g., a $C_{6-10}$ arylsulfinyl group such as phenylsulfinyl, naphthylsulfinyl etc., and the like), an arylsulfonyl group (e.g., a $C_{6-10}$ arylsulfonyl group such as phenylsulfonyl, naphthylsulfonyl etc., and the like), an arylcarbonyl group (e.g., a $C_{6-10}$ aryl-carbonyl group such as benzoyl, naphthoyl etc., and the like), an arylcarbonyloxy group (e.g., a $C_{6-10}$ aryl-carbonyloxy group such as benzoyloxy, naphthoyloxy etc., and the like), an optionally halogenated lower alkylcarbonylamino group (e.g., an optionally halogenated $C_{1-6}$ alkyl-carbonylamino group such as acetylamino, trifluoroacetylamino etc., and the like), a carbamoyl group optionally having substituents (e.g., a group of the formula —$CONR_2R_3$ wherein $R_2$ and $R_3$ are each a hydrogen atom, a hydrocarbon group optionally having substituents or a heterocyclic group optionally having substituents and in the formula —$CONR_2R_3$, $R_2$ and $R_3$ may form a ring together with the adjacent nitrogen atom), an amino group optionally having substituents (e.g., a group of the formula —$NR_2R_3$ wherein $R_2$ and $R_3$ are as defined above and in the formula —$NR_2R_3$, $R_2$ and $R_3$ may form a ring together with the adjacent nitrogen atom), a ureido group optionally having substituents (e.g., a group of the formula —$NHCONR_2R_3$ wherein $R_2$ and $R_3$ are as defined above and in the formula —$NHCONR_2R_3$, $R_2$ and $R_3$ may form a ring together with the adjacent nitrogen atom), a carboxamide group optionally having substituents (e.g., a group of the formula —$NR_2COR_3$ wherein $R_2$ and $R_3$ are as defined above), a sulfonamide group optionally having substituents (e.g., a group of the formula —$NR_2SO_2R_3$ wherein $R_2$ and $R_3$ are as defined above), a heterocyclic group optionally having substituents (as defined for $R_2$ and $R_3$) and the like are used.

As the "hydrocarbon group" of the "hydrocarbon group optionally having substituents" for $R_2$ and $R_3$, for example, a lower alkyl group (e.g., alkyl group having 1 to 6 carbon atoms such as methyl, ethyl, propyl group and the like), a lower alkenyl group (e.g., alkenyl group having 2 to 6 carbon atoms such as vinyl, allyl group and the like), a lower alkynyl group (e.g., alkynyl group having 2 to 6 carbon atoms such as ethynyl, propargyl group and the like), a cycloalkyl group (e.g., cycloalkyl group having 3 to 8 carbon atoms such as cyclopropyl, cyclobutyl, cyclopentyl, cyclohexyl group and the like), a cycloalkenyl group (e.g., cycloalkenyl group having 3 to 8 carbon atoms such as cyclobutenyl, cyclopentenyl, cyclohexenyl group and the like), a cycloalkylalkyl group (e.g., $C_3$-$C_8$ cycloalkyl-$C_1$-$C_6$ alkyl group, such as cyclopropylmethyl, cyclobutylmethyl, cyclopentylmethyl, cyclohexylmethyl group and the like), a cycloalkenylalkyl group (e.g., $C_3$-$C_8$ cycloalkenyl-$C_1$-$C_6$ alkyl group, such as cyclobutenylmethyl, cyclopentenylmethyl, cyclohexenylmethyl group and the like), an aryl group (e.g., aryl group having 6 to 14 carbon atoms such as phenyl, naphthyl group and the like), an arylalkyl group (e.g., $C_6$-$C_{14}$ aryl-$C_1$-$C_6$ alkyl group, such as benzyl, naphthylmethyl group and the like) and the like can be mentioned.

As the "heterocyclic group" of the "heterocyclic group optionally having substituents" represented by $R_2$ and $R_3$, a 5- to 12-membered monocyclic or fused heterocyclic group containing 1 or 2 kinds of 1 to 4 hetero atoms selected from nitrogen atom, sulfur atom and oxygen atom such as pyridyl, pyrrolidinyl, piperazinyl, piperidinyl, 2-oxazepinyl, furyl, decahydroisoquinolyl, quinolyl, indolyl, isoquinolyl, thienyl, imidazolyl, morpholinyl etc., and the like can be mentioned. As the substituent for the "hydrocarbon group optionally having substituents" and "heterocyclic group optionally having substituents" for $R_2$ and $R_3$, for example, a halogen atom (e.g., fluorine, chlorine, bromine, iodine etc.), a lower alkyl group (e.g., alkyl group having 1 to 6 carbon atoms such as methyl, ethyl, propyl group and the like), a lower alkenyl group (e.g., alkenyl group having 2 to 6 carbon atoms such as vinyl, allyl group and the like), a lower alkynyl group (e.g., alkynyl group having 2 to 6 carbon atoms such as ethynyl, propargyl group and the like), a cycloalkyl group (e.g., cycloalkyl group having 3 to 8 carbon atoms such as cyclopropyl, cyclobutyl, cyclopentyl, cyclohexyl group and the like), a lower alkoxy group (e.g., alkoxy group having 1 to 6 carbon atoms such as methoxy, ethoxy group and the like), a nitro group, a cyano group, a hydroxy group, a thiol group, a carboxyl group, a lower alkanoyl group (e.g., formyl; $C_{1-6}$ alkyl-carbonyl group, such as acetyl, propionyl, butyryl group and the like), a lower alkanoyloxy group (e.g., formyloxy; $C_{1-6}$ alkyl-carbonyloxy group, such as acetyloxy, propionyloxy group and the like), a lower alkoxycarbonyl group (e.g., $C_{1-6}$ alkoxy-carbonyl group, such as methoxycarbonyl, ethoxycarbonyl, propoxycarbonyl group and the like), an aralkyloxycarbonyl group (e.g., $C_{7-17}$ aralkyloxy-carbonyl group, such as benzyloxycarbonyl group and the like), an aryl group (e.g., $C_{6-14}$ aryl group, such as phenyl, naphthyl group and the like), an aryloxy group (e.g., $C_{6-14}$ aryloxy group having, such as phenyloxy, naphthyloxy group and the like), an arylcarbonyl group (e.g., $C_{6-14}$ aryl-carbonyl group, such as benzoyl, naphthoyl group and the like), an arylcarbonyloxy group (e.g., $C_{6-14}$ aryl-carbonyloxy group, such as benzoyloxy, naphthoyloxy group and the like), a carbamoyl group optionally having substituents (e.g., carbamoyl; carbamoyl group mono- or di-substituted by alkyl group having 1 to 6 carbon atoms such as methylcarbamoyl, dimethylcarbamoyl group etc., and the like), an amino group optionally having substituents (e.g., amino; amino group mono- or di-substituted by alkyl group having 1 to 6 carbon atoms such as methylamino, dimethylamino, ethylamino, diethylamino group etc., and the like) and the like can be mentioned. The number and the position of the substitutions are not particularly limited.

As the ring formed by $R_2$ and $R_3$ together with the adjacent nitrogen atom, for example, pyrrolidine, piperidine, homopiperidine, morpholine, piperazine, tetrahydroquinoline, tetrahydroisoquinoline and the like can be mentioned.

The "hydrocarbon group" of the "hydrocarbon group optionally having substituents" represented by the above-mentioned E, R, $R_1$ and Y may have 1 to 5, preferably 1 to 3, the aforementioned substituent at substitutable positions of the hydrocarbon group, wherein, when the number of substituents is not less than 2, each substituents are the same or different.

As the "heterocyclic group" of the "heterocyclic group optionally having substituents" represented by the above-mentioned E, R and Y, a 5- to 12-membered aromatic heterocyclic group and saturated or unsaturated non-aromatic heterocyclic group containing, as ring-constituting atom (ring atom), 1 to 3 (preferably 1 or 2) kinds of at least 1 (preferably 1 to 4, more preferably 1 to 3) hetero atoms selected from oxygen atom, sulfur atom and nitrogen atom and the like can be mentioned. As the mentioned above, as the "heterocyclic group" of the "heterocyclic group optionally having substituents" represented by Y, a saturated oxygen-containing heterocyclic group containing, as ring atoms, 1 to 4, more preferably 1 to 3, hetero atoms selected from oxygen atom, sulfur atom and nitrogen atom etc., and the like are preferable, particularly a 5- to 12-membered saturated oxygen-containing heterocyclic group and the like are preferable.

As the "aromatic heterocyclic group", an aromatic monocyclic heterocyclic group, an aromatic fused heterocyclic group and the like can be mentioned.

As the "aromatic monocyclic heterocyclic group", for example, a 5- or 6-membered aromatic monocyclic heterocyclic group such as furyl, thienyl, pyrrolyl, oxazolyl, isooxazolyl, thiazolyl, isothiazolyl, imidazolyl, pyrazolyl, 1,2,3- oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc., and the like can be mentioned.

As the "aromatic fused heterocyclic group", for example, a 8- to 12-membered aromatic fused heterocyclic group (preferably a heterocyclic group wherein the aforementioned 5- or 6-membered aromatic monocyclic heterocyclic group is condensed with a benzene ring, or a heterocyclic group wherein the same or different two heterocyclic groups of the aforementioned 5- or 6-membered aromatic monocyclic heterocyclic group are condensed), such as benzofuranyl, isobenzofuranyl, benzothienyl, isobenzothienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl etc., and the like can be mentioned.

As the "saturated or unsaturated non-aromatic heterocyclic group", for example, a 3- to 8-membered (preferably 5- or 6-membered) saturated or unsaturated (preferably saturated) non-aromatic heterocyclic group (aliphatic heterocyclic group) such as oxylanyl, azetidinyl, oxetanyl, thietanyl, pyrrolidinyl, tetrahydrofuryl, thiolanyl, piperidinyl, tetrahydropyranyl, thianyl, morpholinyl, thiomorpholinyl, piperazinyl, azepanyl, oxepanyl, thiepanyl, oxazepanyl, thiazepanyl, azocanyl, oxocanyl, thiocanyl, oxazocanyl, thiazocanyl and the like can be mentioned. These may be oxo-substituted and examples thereof include 2-oxoazetidinyl, 2-oxopyrrolidinyl, 2-oxopiperidinyl, 2-oxazepanyl, 2-oxazocanyl, 2-oxotetrahydrofuryl, 2-oxotetrahydropyranyl, 2-oxothiolanyl, 2-oxothianyl, 2-oxopiperazinyl, 2-oxooxepanyl, 2-oxooxazepanyl, 2-oxothiepanyl, 2-oxothiazepanyl, 2-oxooxocanyl, 2-oxothiocanyl, 2-oxooxazocanyl, 2-oxothiazocanyl and the like. A 5-membered non-aromatic heterocyclic group such as 2-oxopyrrolidinyl and the like is preferable.

As the substituent that the "heterocyclic group" of the "heterocyclic group optionally having substituents" represented by the above-mentioned E, R and Y may have, for example, those similar to the "substituent" of the "hydrocarbon group optionally having substituents" represented by the aforementioned E, R, $R_1$ and Y and the like are used.

The "heterocyclic group" of the "heterocyclic group optionally having substituents" represented by E, R and Y may each have 1 to 5, preferably 1 to 3, substituents mentioned above at substitutable positions of the heterocyclic group, and when the number of substituents is two or more, the substituents are the same or different.

The bond between R and W in the compound of the present invention is explained below. When R and W are bonded, the position of the bond between R and W is not particularly limited as long as R and W can be bonded.

The bondable position of R is the position where the "hydrocarbon group" and "substituent" of the "hydrocarbon group optionally having substituents" defined above for R can be bonded, and the position where the "heterocyclic group" and "substituent" of the "heterocyclic group optionally having substituents" defined above for R can be bonded.

As the bondable position of W, a bondable position of the "divalent chain hydrocarbon group" of the "divalent chain hydrocarbon group optionally having substituents" defined above for W, a bondable position of the "divalent chain hydrocarbon group" defined above for $W_1$ and $W_2$, a bondable position of the "hydrocarbon ring" of the "hydrocarbon ring optionally having substituents" defined above for ring Z, and a bondable position of the "heterocyclic group" of the "heterocyclic group optionally having substituents" defined above for ring Z can be mentioned.

R and W can be bonded at the bondable position thereof and can form a ring together with the adjacent nitrogen atom. As such ring, for example, a saturated nitrogen-containing ring (e.g., azetidine, pyrrolidine, piperidine, homopiperidine etc.), an unsaturated nitrogen-containing ring (e.g., tetrahydropyridine etc.), an aromatic nitrogen-containing ring (e.g., pyrrole etc.), a hetero ring (e.g., piperazine, morpholine etc.) containing, besides the nitrogen atom to which R and W are adjacent, at least one hetero atom selected from the group consisting of nitrogen, oxygen and sulfur, a fused ring (e.g., indole, indoline, isoindole, isoindoline, tetrahydroquinoline, tetrahydroisoquinoline etc.) and the like can be mentioned. Of these, a 4- to 7-membered ring is preferable.

The ring formed by R and W, which are bonded at each bondable position thereof, together with the adjacent nitrogen atom may have 1 to 4 substituents at substitutable positions thereof. When the number of substituents is 2 or more, the substituents are the same or different. As the substituent, the substituents of the "hydrocarbon group optionally having substituents" and "heterocyclic group optionally having substituents" defined for R, and the substituents of the "divalent chain hydrocarbon group optionally having substituents" defined for W can be mentioned. Specifically, a halogen atom (e.g., fluorine, chlorine, bromine, iodine etc.), a $C_{1-6}$ alkyl group such as methyl, ethyl, propyl, isopropyl, butyl, isobutyl, sec-butyl, tert-butyl, pentyl, 1-ethylpropyl, hexyl etc., and the like can be mentioned.

By the bond between R and W, for example,

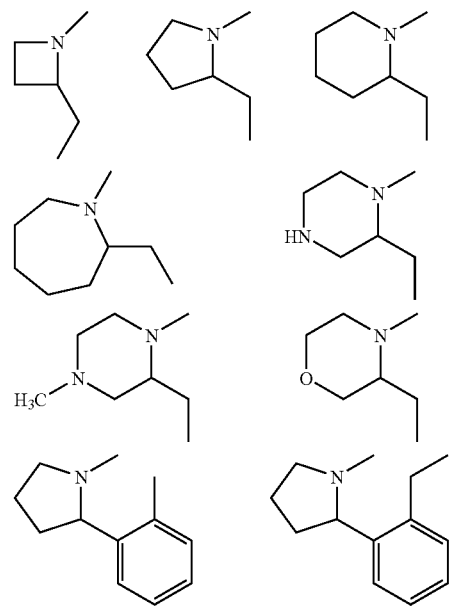

and the like are formed, but the ring is not limited to these. These may have substituents as defined above, and it would be understood for those of ordinary skill in the art that they may also have an isomer.

In the present invention, X represents a leaving group, such as a halogen atom, a benzotriazolyl group, a (2,5-dioxypyrrolidin-1-yl)oxy group and the like. Of these, a halogen atom such as fluorine, chlorine, bromine, iodine and the like is preferable, and chlorine is particularly preferable.

In the present invention, M represents a hydrogen atom, a metal cation or a quaternary ammonium ion.

In the present invention, the "metal cation" is exemplified by alkali metal ion (e.g., $Na^+$, $K^+$, $Li^+$, $Cs^+$ and the like), with preference given to $Na^+$.

In the present invention, the "quaternary ammonium ion" is exemplified by tetramethylammonium ion, tetraethylammonium ion, tetrapropylammonium ion, tetrabutylammonium ion and the like, with preference given to tetrabutylammonium ion.

In the compound (I), a pharmacologically acceptable basic salt can be formed between an acidic group in a molecule and an inorganic base or an organic base etc, and a pharmacologically acceptable acid addition salt can be formed between a basic group in a molecule and an inorganic acid or an organic acid etc.

Examples of the inorganic basic salt of compound (I) include salt with alkali metal (e.g., sodium, potassium and the like), alkaline earth metal (e.g., calcium and the like), ammonia etc., and the like, and examples of the organic basic salt of compound (I) include salt with dimethylamine, triethylamine, piperazine, pyrrolidine, piperidine, 2-phenylethylamine, benzylamine, ethanolamine, diethanolamine, pyridine, collidine etc., and the like.

Examples of the acid addition salt of compound (I) include inorganic acid salt (e.g., hydrochloride, sulfate, hydrobromide, phosphate and the like), organic acid salt (e.g., acetate, trifluoroacetate, succinate, maleate, fumarate, propionate, citrate, tartrate, lactate, oxalate, methanesulfonate, p-toluenesulfonate and the like) and the like.

The compound (I) of the present invention encompasses hydrates. Examples of the "hydrate" include 0.5 hydrate-5.0 hydrate. Of these, 0.5 hydrate, 1.0 hydrate, 1.5 hydrate and 2.0 hydrate are preferable.

The compound (I) of the present invention encompasses racemates and optically active compounds. As the optically active compound, such compound wherein one enantiomer is in enantiomer excess (e.e.) of not less than 90% is preferable, more preferably in enantiomer excess of not less than 99%. As an optically active form, an (R)-form represented by the formula wherein each symbol is as defined above, is preferable.

As the preferable compounds encompassed in compound (I), for example, the following specific compounds can be mentioned.

That is,

2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl trimethylacetate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl cyclohexanecarboxylate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl benzoate, 2-[methyl[[2-[[[3-methyl-4-(2,2,2-trifluoroethoxy)-2-pyridyl]methyl]sulfinyl]-1H-benzimidazol-1-yl]carbonyl]amino]ethyl benzoate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-methoxybenzoate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3-chlorobenzoate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4-difluorobenzoate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-trifluoromethoxybenzoate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-fluorobenzoate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4,5-trimethoxybenzoate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 2-pyridinecarboxylate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl methoxyacetate, ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, isopropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, isopropyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate, benzyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate, 2-methoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 2-[ethyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate, 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate, ethyl 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 2-[cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate, 2-[cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl ethyl carbonate, 2-[[[(R)-2-[[[3-methyl-4-(2,2,2-trifluoroethoxy)-2-pyridyl]methyl]sulfinyl]-1H-benzimidazol-1-yl]carbonyl](phenyl)amino]ethyl acetate, 2-[[[2-[[[3-methyl-4-(2,2,2-trifluoroethoxy)-2-pyridyl]methyl]sulfinyl]-1H-benzimidazol-1-yl]carbonyl](phenyl)amino]ethyl acetate, tert-butyl[2-[methyl[[(R)-2-[[[3-methyl-4-(2,2,2-trifluoroethoxy)-2-pyridyl]methyl]sulfinyl]-1H-benzimidazol-1-yl]carbonyl]amino]-3-pyridyl]methyl carbonate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]benzyl acetate, 2-[[2-(acetyloxy)ethyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate,

[(2S)-1-[[(R)-2-[[[3-methyl-4-(2,2,2-trifluoroethoxy)-2-pyridyl]methyl]sulfinyl]-1H-benzimidazol-1-yl]carbonyl]-2-pyrrolidinyl]methyl acetate, ethyl[methyl[[(R)-2-[[[3-methyl-4-(2,2,2-trifluoroethoxy)-2-pyridyl]methyl]sulfinyl]-1H-benzimidazol-1-yl]carbonyl]amino]acetate, 2-[[[5-methoxy-2-[[(4-methoxy-3,5-dimethyl-2-pyridyl)methyl]sulfinyl]-1H-benzoimidazol-1-yl]carbonyl](methyl)amino]ethyl benzoate, 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl benzoate, 2-[methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate, ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate, ethyl 2-[methyl[[(S)-2-[[[3-methyl-4-(2,2,2-trifluoroethoxy)-2-pyridyl]methyl]sulfinyl]-1H-benzimidazol-1-yl]carbonyl]amino]ethyl carbonate, ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate, 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl acetate, 2-[[[5-methoxy-2-[[(4-methoxy-3,5-dimethyl-2-pyridyl)methyl]sulfinyl]-3H-imidazo[4,5-b]pyridin-3-yl]carbonyl](phenyl)amino]ethyl acetate, 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl acetate, ethyl 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl carbonate, ethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl carbonate, 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl acetate, 3-[methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl diacetate, diethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl biscarbonate, 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl 3-chlorobenzoate, 2-[methyl[[2-[[[3-methyl-4-(2,2,2-trifluoroethoxy)-2-pyridyl]methyl]sulfinyl]-1H-benzimidazol-1-yl]carbonyl]amino]ethyl acetate, 2-ethoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 3-methoxypropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl N,N-dimethylglycinate, S-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl]thioacetate, ethyl 2-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]ethyl carbonate, ethyl 2-[methyl[[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]carbonyl]amino]ethyl carbonate, ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate, 2-[[[5-methoxy-2-[[(4-methoxy-3,5-dimethyl-2-pyridyl)methyl]sulfinyl]-1H-benzimidazol-1-yl]carbonyl](phenyl)amino]ethyl acetate, ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate, ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate, 2-[[[2-[[[4-(3-methoxypropoxy)-3-methyl-2-pyridyl]methyl]sulfinyl]1-1H-benzimidazol-1-yl]carbonyl](phenyl)amino]ethyl acetate, 2-[[[5-(difluoromethoxy)-2-[[(3,4-dimethoxy-2-pyridyl)methyl]sulfinyl]-1H-benzimidazol-1-yl]carbonyl](methyl)amino]ethyl ethyl carbonate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methylpiperidine-4-carboxylate,
2-[[4-(aminocarbonyl)phenyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methyl-4-piperidinyl carbonate,
2-[[4-(aminocarbonyl)phenyl][[2-[[[3-methyl-4-(2,2,2-trifluoroethoxy)-2-pyridyl]methyl]sulfinyl]-1H-benzimidazol-1-yl]carbonyl]amino]ethyl acetate,
(−)-ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate and
(+)-ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate, a salt thereof and the like can be mentioned.

Of these, the following compounds and salts thereof are preferable.

2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
2-[methyl[[(R)-2-[[[3-methyl-4-(2,2,2-trifluoroethoxy)-2-pyridyl]methyl]sulfinyl]-1H-benzimidazol-1-yl]carbonyl]amino)ethyl tetrahydropyran-4-yl carbonate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate,
ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate,
ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate,
2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl acetate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl acetate,
ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate,
ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate,
ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate, and
2-[[[5-(difluoromethoxy)-2-[[(3,4-dimethoxy-2-pyridyl)methyl]sulfinyl]-1H-benzimidazol-1-yl]carbonyl](methyl)amino]ethyl ethyl carbonate.

The compound (I) can be produced by the following method A or B.

(Method A)

The compound (I) or a salt thereof can be obtained by condensation of compound (III) or a salt thereof with compound (IV) or a salt thereof in the presence or absence of a base. The salt of compound (III) and the salt of compound (IV) here are exemplified by the above-mentioned salts of compound (I). For example, acid addition salts such as inorganic acid salt (e.g., hydrochloride, sulfate, hydrobromide, phosphate and the like), organic acid salt (e.g., acetate, trifluoroacetate, succinate, maleate, fumarate, propionate, citrate, tartrate, lactate, oxalate, methanesulfonate, p-toluenesulfonate and the like), and the like can be mentioned.

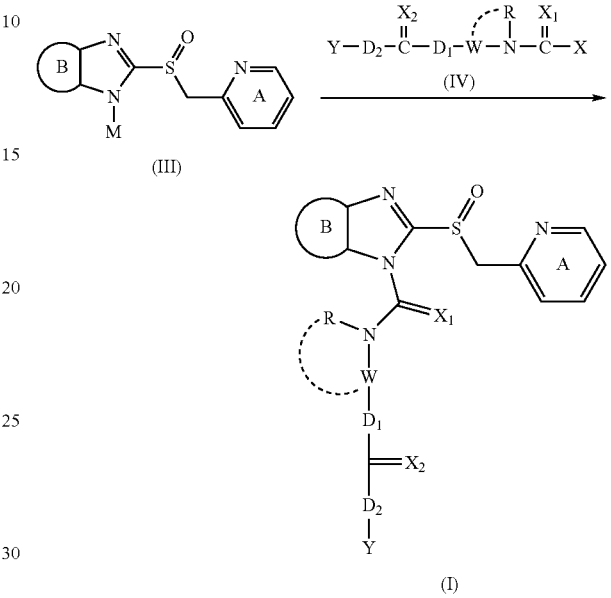

wherein each symbol is as defined above. The reaction of Method A is generally conducted in a solvent, and a solvent that does not inhibit the reaction of Method A is selected as appropriate. Examples of such solvent include ethers (e.g., dioxane, tetrahydrofuran, diethyl ether, tert-butyl methyl ether, diisopropyl ether, ethylene glycol dimethyl ether and the like), esters (e.g., ethyl formate, ethyl acetate, butyl acetate and the like), halogenated hydrocarbons (e.g., dichloromethane, chloroform, carbon tetrachloride, trichlene, 1,2-dichloroethane and the like), hydrocarbons (e.g., n-hexane, benzene, toluene and the like), amides (e.g., formamide, N,N-dimethylformamide, N,N-dimethylacetamide and the like), ketones (e.g., acetone, methyl ethyl ketone, methyl isobutyl ketone and the like), nitriles (e.g., acetonitrile, propionitrile and the like) and the like, as well as dimethyl sulfoxide, sulfolane, hexamethylphosphoramide, water and the like, which may be used alone or as a mixed solvent. The amount of the solvent to be used is not particularly limited as long as the reaction mixture can be stirred, which is generally 2- to 100-fold amount by weight, preferably 5- to 50-fold amount by weight, relative to 1 mole of compound (III) or a salt thereof.

The amount of compound (IV) or a salt thereof to be used is generally 1-10 mole, preferably 1-3 mole, relative to 1 mole of compound (III) or a salt thereof.

The reaction of Method A is carried out within a temperature range of from about 0° C. to 100° C., preferably 20° C. to 80° C.

The reaction time of Method A varies depending on the kind of compounds (III), (IV) or a salt thereof and solvent, reaction temperature and the like, but it is generally 1 min.-96 hrs., preferably 1 min.-72 hrs., more preferably 15 min.-24 hrs.

The base in Method A is, for example, an inorganic base (e.g., sodium carbonate, potassium carbonate, calcium carbonate, sodium hydrogen carbonate etc.), a tertiary amine (e.g., triethylamine, tripropylamine, tributylamine, cyclohexyldimethylamine, pyridine, lutidine, γ-collidine, N,N-dimethylaniline, N-methylpiperidine, N-methylpyrrolidine, N-methylmorpholine, 4-dimethylaminopyridine and the like); alkylene oxides (e.g., propylene oxide, epichlorohydrin etc.) and the like. The amount of the base to be used is generally 1 mole-10 mole, preferably 1 mole-3 mole, relative to 1 mole of compound (IV) or a salt thereof.

The compound (III) or a salt thereof can be produced according to the method described in JP-A-61-50978, U.S. Pat. No. 4,628,098 and the like or a method similar thereto.

The compound (IV) or a salt thereof can be produced according to a method known per se or a method analogous thereto. For example, when X is a chlorine atom, compound (IV) can be obtained by reacting a compound represented by the formula (VI):

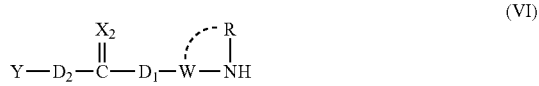

(VI)

wherein each symbol is as defined above, or a salt thereof with phosgene, trichloromethyl chloroformate, bis(trichloromethyl)carbonate, thiophosgene and the like in the presence of an acid scavenger in a solvent (e.g., tetrahydrofuran, acetonitrile, dichloromethane etc.). Alternatively, compound (IV) can be also obtained by treating ethylcarbamate, which is obtained by reacting compound (VI) or a salt thereof with ethyl chloroformate, with phosphorus oxychloride according to the method described in Synthetic Communications, vol. 17, p. 1887 (1987) or a method analogous thereto. As the salt of compound (VI), for example, acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.), and the like can be mentioned.

As the acid scavenger used here, for example, inorganic bases (e.g., sodium carbonate, potassium carbonate, calcium carbonate, sodium hydrogen carbonate etc.), tertiary amine (e.g., triethylamine, tripropylamine, tributylamine, cyclohexyldimethylamine, pyridine, lutidine, γ-collidine, N,N-dimethylaniline, N-methylpiperidine, N-methylpyrrolidine, N-methylmorpholine, 4-dimethylaminopyridine etc.) and the like can be mentioned.

The compound (VI) and a salt thereof can be produced according to a method known per se or a method analogous thereto. For example, when $D_1$ is other than a bond, compound (VI) can be obtained by condensing a compound represented by the formula (VII):

(VII)

wherein $R_4$ is a hydrogen atom or nitrogen-protecting group, and other symbols are as defined above, or a salt thereof with carboxylic acid or thionic acid represented by the formula (VIII):

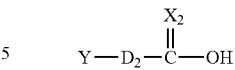

(VIII)

wherein each symbol is as defined above, or a reactive derivative thereof (e.g., anhydride, halide etc.), or a salt thereof in a suitable solvent (e.g., ethyl acetate, tetrahydrofuran, dichloromethane, N,N-dimethylformamide etc., followed by deprotection as necessary. As the salt of compound (VII), for example, acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.) etc., and the like can be mentioned.

Alternatively, when $D_1$ is a bond, compound (VI) can be obtained by condensing carboxylic acid or thionic acid represented by the formula (IX):

(IX)

wherein each symbol is as defined above, or a reactive derivative thereof (e.g., anhydride, halide etc.), or a salt thereof with a compound represented by Y-$D_2$-H in a suitable solvent (e.g., ethyl acetate, tetrahydrofuran, dichloromethane, N,N-dimethylformamide etc.), followed by deprotection, as necessary. As the salt of compound (IX), for example, acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.) and the like, salts with alkali metal (e.g., sodium, potassium etc.), alkaline earth metal (e.g., calcium etc.), ammonia etc., and the like, and for example, organic base such as dimethylamine, triethylamine, piperazine, pyrrolidine, piperidine, 2-phenylethylamine, benzylamine, ethanolamine, diethanolamine, pyridine, collidine etc., and the like can be mentioned.

As the protecting group represented by $R_4$ in the formula (VII) and the formula (IX), for example, a formyl group, a $C_{1-6}$ alkyl-carbonyl group (e.g., acetyl, ethylcarbonyl etc.), a benzyl group, a tert-butyloxycarbonyl group, a benzyloxycarbonyl group, an allyloxycarbonyl group, a $C_{7-10}$ aralkyl-carbonyl group (e.g., benzylcarbonyl etc.), a trityl group and the like are used. These groups may be substituted by 1 to 3 halogen atoms (e.g., fluorine, chlorine, bromine etc.), a nitro group and the like.

As a method for removing such protecting groups, a method known per se or a method analogous thereto is used, which is, for example, a method using an acid, a base, reduction, UV light, palladium acetate etc., and the like are used.

(Method B)

The compound (I) and a salt thereof can be obtained by subjecting compound (V) or a salt thereof to oxidization reaction.

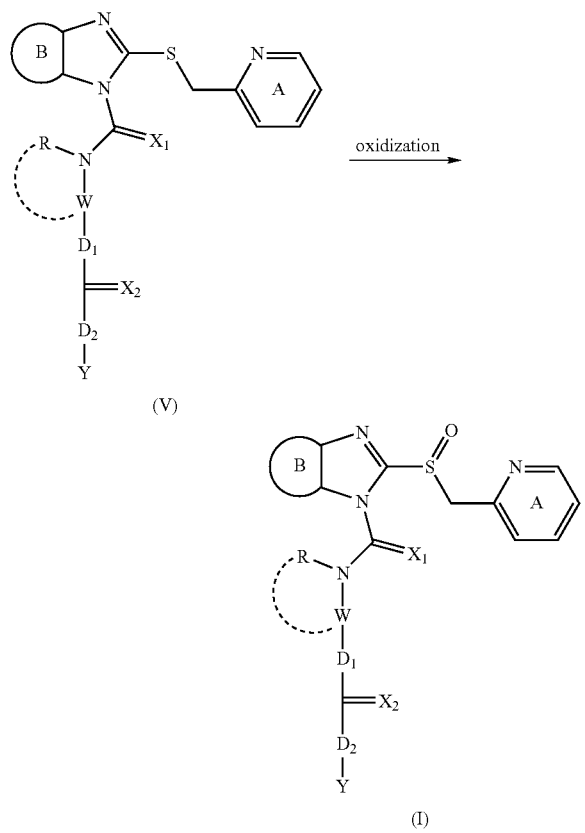

(V)

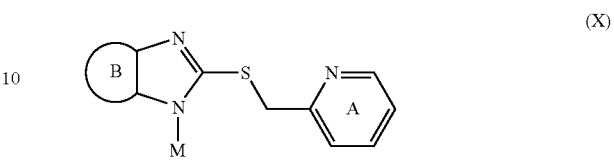

(X)

wherein each symbol is as defined above.

The reaction in Method B can be carried out using an oxidant such as nitric acid, hydrogen peroxide, peroxyacid, peroxyacid ester, ozone, dinitrogen tetraoxide, iodosobenzene, N-halosuccinimide, 1-chlorobenzotriazole, tert-butyl hypochlorite, diazabicyclo[2.2.2]octane-bromine complex, sodium metaperiodate, selenium dioxide, manganese dioxide, chromic acid, cerium ammonium nitrate, bromine, chlorine, sulfuryl chloride, magnesium monoperoxyphthalate and the like. The amount of the oxidant to be used is generally 0.5 mole-2 mole, preferably 0.8 mole-1.2 mole, per 1 mole of compound (I) or a salt thereof. The oxidization may be carried out using the above-mentioned oxidant such as hydrogen peroxide and peroxyacids in the presence of a catalyst such as vanadium acetate, vanadium oxide acetylacetonate, titanium tetraisopropoxide and the like.

The reaction of Method B is generally carried out in a solvent inert to the above-mentioned oxidation reaction. Examples of the "inert solvent" include water, alcohols (e.g., methanol, ethanol, 1-propanol, 2-propanol etc.), ketones (e.g., acetone, methyl ethyl ketone etc.), nitriles (e.g., acetonitrile, propionitrile etc.), amides (e.g., formamide, N,N-dimethylformamide etc.), ethers (e.g., diethyl ether, tert-butyl methyl ether, diisopropyl ether, dioxane, tetrahydrofuran etc.), sulfoxides (e.g., dimethyl sulfoxide etc.) and polar solvents (e.g., sulfolane, hexamethylphosphoramide etc.), which may be used alone or as a mixed solvent thereof. The "inert solvent" is used in generally 1- to 100-fold amount by weight of compound (V) or a salt thereof.

The reaction temperature is generally from −80° C. to 80° C., preferably from 0° C. to 30° C.

The reaction time is generally 1 min.-6 hrs., preferably 15 min.-1 hr.

The compound (V), which is a starting material in Method B, can be obtained by a reaction similar to that in Method A, by the use of, for example, a compound represented by the following formula (X):

wherein each symbol is as defined above, instead of compound (III).

The compound (X) can be synthesized according to the methods described in the following references or a method analogous thereto: JP-A-61-50978, JP-A-54-141783, JP-A-61-22079, JP-A-1-6270, JP-A-63-146882.

The salt of compound (V) is exemplified by the above-mentioned salts of the compound (I), which are acid addition salts such as inorganic acid salt (e.g., hydrochloride, sulfate, hydrobromide, phosphate and the like), organic acid salt (e.g., acetate, trifluoroacetate, succinate, maleate, fumarate, propionate, citrate, tartrate, lactate, oxalate, methanesulfonate, p-toluenesulfonate and the like) and the like.

The compound (I) or a salt thereof obtained by the above-mentioned methods A or B can be isolated and purified from the reaction mixture by a separation means known per se (e.g., concentration, concentration under reduced pressure, solvent extraction, crystallization, recrystallization, phase transfer, chromatography and the like). Since compound (I) and a salt thereof obtained by the above-mentioned methods A or B encompass any isomers thereof, optically pure compound (I) and a salt thereof can be obtained by, for example, subjecting compound (I) or a salt thereof to optical resolution, or asymmetric oxidation of compound (V) or a salt thereof.

The method of optical resolution includes methods known per se, such as a fractional recrystallization method, a chiral column method, a diastereomer method, and so forth. Asymmetric oxidation includes methods known per se, such as the method described in WO96/02535 and the like.

The "fractional recrystallization method" includes a method in which a salt is formed between a racemate and an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.)], which salt is separated by fractional recrystallization etc., and, if desired, subjected to a neutralization process to give a free optical isomer.

The "chiral column method" includes a method in which a racemate or a salt thereof is applied to a column for optical isomer separation (chiral column). In the case of liquid chromatography, for example, optical isomers are separated by adding a racemate to a chiral column such as ENANTIO-OVM (produced by Tosoh Corporation), the DAICEL CHIRAL series (produced by Daicel Corporation) and the like, and developing the racemate in water, a buffer (e.g., phosphate buffer), an organic solvent (e.g., hexane, ethanol, methanol, isopropanol, acetonitrile, trifluoroacetic acid, diethylamine, triethylamine, etc.), or a solvent mixture thereof. In the case of gas chromatography, for example, a chiral column such as CP-Chirasil-DeX CB (produced by GL Science) and the like is used to separate optical isomers.

The "diastereomer method" includes a method in which a racemate and an optically active reagent are reacted to give a diastereomeric mixture, which is then subjected to ordinary separation means (e.g., fractional recrystallization, chromatography, etc.) to obtain either diastereomer, which is subjected to a chemical reaction (e.g., acid hydrolysis, base hydrolysis, hydrogenolysis, etc.) to cut off the optically active reagent moiety, whereby the desired optical isomer is obtained. Said "optically active reagent" includes, for example, optically active organic acids such as MTPA [α-methoxy-α-(trifluoromethyl)phenylacetic acid], (−)-menthoxyacetic acid and the like, optically active alkoxymethyl halides such as (1R-endo)-2-(chloromethoxy)-1,3,3-trimethylbicyclo[2.2.1]heptane etc., and the like.

The compound (I) and a salt thereof of the present invention are useful as a pharmaceutical agent, because they show, after in vivo administration, a superior anti-ulcer activity, a gastric acid secretion-suppressive action, a mucosa-protecting action, an anti-*Helicobacter pylori* action and the like, as well as low toxicity. In addition, since they are stable to acid, they do not require formulation into an enteric-coated preparation for oral administration, which in turn eliminates the cost for formulating enteric-coated preparation. Moreover, the tablet can be made smaller, which is easily swallowed by patients having difficulty in swallowing, particularly the elderly and children. Furthermore, since absorption is faster than in enteric-coated preparations, expression of gastric acid secretion-suppressive action is rapid. The preparation is long-acting because it is gradually converted to the original compound in living organisms. Consequently, the compounds are useful as anti-ulcer agents and the like. In addition, compound (I) and a salt thereof of the present invention as prodrugs are expected to provide an effect of improvement of absorption, control of intensity of pharmacological action, reduction of side effects, improvement of uncomfortable taste, reduction of irritation, expansion of selectivity of formulation of preparations, improvement of administration route and the like as compared to the original compounds, though subject to change depending on the kind of the substituents. When enteric coating is not necessary as mentioned above, miniaturization of preparation, low cost of preparation and the like can be achieved, affording greater benefit in the industrial production. As described, compound (I) and a salt thereof have various superior effects as a prodrug. Among others, they are particularly useful as anti-ulcer agents and the like in that chemical stability can be improved and a sustained pharmacological action is attainable.

The compound (I) and a salt thereof of the present invention are useful for the prophylaxis or treatment of peptic ulcer (e.g., gastric ulcer, gastric ulcer due to post-operative stress, duodenal ulcer, anastomotic ulcer, ulcer caused by nonsteroidal anti-inflammatory agent etc.); gastritis; reflux esophagitis; symptomatic gastroesophageal reflux diseases (symptomatic GERD); NUD (Non Ulcer Dyspepsia); gastric cancer (including gastric cancer due to promoted production of interleukin-1β caused by genetic polymorphism of interleukin-1); gastric MALT lymphoma; Zollinger-Ellison syndrome; gastric hyperacidity (e.g. gastric hyperacidity due to post-operative stress); hemorrhage of upper gastrointestinal tract caused by acute stress ulcer, hemorrhagic gastritis or invasion stress (stress due to major surgery requiring intensive management after operation and cerebrovascular disorder, external injury in the head, multiple organ failure and extensive burn requiring intensive treatment), pre-anesthetic administration, eradication of *Helicobacter pylori* and the like in mammals (e.g., human, simian, sheep, cattle, horse, dog, cat, rabbit, rat, mouse etc.).

The compound (I) and a salt thereof of the present invention show low toxicity and can be safely administered orally or parenterally (e.g., topical, rectal, intravenous administrations and the like) as they are or as a preparation containing a pharmaceutical composition containing a pharmacologically acceptable carrier admixed according to a method known per se, such as tablets (including sugar-coated tablets and film-coated tablets), powder, granule, capsule (including soft capsule), orally disintegrating tablet, liquid, injection, suppository, sustained-release preparation, plaster and the like.

The content of compound (I) or a salt thereof of the present invention in the pharmaceutical composition of the present invention is about 0.01 to 100% by weight relative to the entire composition. Though subject to change depending on the administration target, administration route, disease and the like, its dose is about 0.5 to 1,500 mg/day, preferably about 5 to 150 mg/day, based on the active ingredient, when, for example, the compound is orally administered as an anti-ulcer agent to an adult human (60 kg). The compound (I) or a salt thereof of the present invention may be administered once daily or in 2 or 3 divided portions per day.

The pharmacologically acceptable carrier that may be used to produce the pharmaceutical composition of the present invention includes various organic or inorganic carrier substances in common use as pharmaceutical materials, including excipients, lubricants, binders, disintegrants, water-soluble polymers and basic inorganic salts for solid preparations; and solvents, dissolution aids, suspending agents, isotonizing agents, buffers and soothing agents for liquid preparations and the like. Other ordinary pharmaceutical additives such as preservatives, anti-oxidants, coloring agents, sweetening agents, souring agents, bubbling agents and flavorings may also be used as necessary.

Such "excipients" include, for example, lactose, sucrose, D-mannitol, starch, cornstarch, crystalline cellulose, light silicic anhydride, titanium oxide and the like.

Such "lubricants" include, for example, magnesium stearate, sucrose fatty acid esters, polyethylene glycol, talc, stearic acid and the like.

Such "binders" include, for example, hydroxypropyl cellulose, hydroxypropylmethyl cellulose, crystalline cellulose, starch, polyvinylpyrrolidone, powdered acacia, gelatin, pullulan, low-substituted hydroxypropyl cellulose and the like.

Such "disintegrants" include (1) crosslinked povidone, (2) what is called super-disintegrants such as crosslinked carmellose sodium (FMC-Asahi Chemical) and carmellose calcium (Gotoku Yakuhin) etc, (3) carboxymethyl starch sodium (e.g., product of Matsutani Chemical), (4) low-substituted hydroxypropyl cellulose (e.g., product of Shin-Etsu Chemical), (5) cornstarch, and so forth. Said "crosslinked povidone" may be any crosslinked polymer having the chemical name 1-ethenyl-2-pyrrolidinone homopolymer, including polyvinylpyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP), Polyplasdon INF-10 (produced by ISP) and the like.

Such "water-soluble polymers" include, for example, ethanol-soluble water-soluble polymers [e.g., cellulose derivatives such as hydroxypropyl cellulose (hereinafter also referred to as HPC) etc, polyvinylpyrrolidone and the like], ethanol-insoluble water-soluble polymers [e.g., cellulose derivatives such as hydroxypropylmethyl cellulose (hereinafter also referred to as HPMC) etc., methyl cellulose, carboxymethyl cellulose sodium and the like, sodium polyacrylate, polyvinyl alcohol, sodium alginate, guar gum and the like] and the like.

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogen carbonate, disodium hydrogen phosphate and the like. Such basic inorganic salts of potassium include, for example, potassium carbonate, potassium hydrogen carbonate and the like. Such basic inorganic salts of magnesium include, for example, heavy magnesium carbonate, magnesium carbonate, magnesium oxide, magnesium hydroxide, magnesium metasilicate aluminate, magnesium silicate, magnesium aluminate, synthetic hydrotalcite [$Mg_6Al_2(OH)_{16}CO_3 4H_2O$], and alumina hydroxide magnesium. Preferred are heavy magnesium carbonate, magnesium carbonate, magnesium oxide, magnesium hydroxide and the like. Such basic inorganic salts of calcium include, for example, precipitated calcium carbonate, calcium hydroxide, etc.

Such "solvents" include, for example, water for injection, alcohol, propylene glycol, macrogol, sesame oil, corn oil, olive oil and the like.

Such "dissolution aids" include, for example, polyethylene glycol, propylene glycol, D-mannitol, benzyl benzoate, ethanol, trisaminomethane, cholesterol, triethanolamine, sodium carbonate, sodium citrate and the like.

Such "suspending agents" include, for example, surfactants such as stearyltriethanolamine, sodium lauryl sulfate, laurylaminopropionic acid, lecithin, benzalkonium chloride, benzethonium chloride, monostearic glycerol etc; hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose etc., and the like.

Such "isotonizing agents" include, for example, glucose, D-sorbitol, sodium chloride, glycerol, D-mannitol and the like.

Such "buffers" include, for example, buffer solutions of phosphates, acetates, carbonates, citrates etc, and the like.

Such "soothing agents" include, for example, benzyl alcohol and the like.

Such "preservatives" include, for example, p-oxybenzoic acid esters, chlorobutanol, benzyl alcohol, phenethyl alcohol, dehydroacetic acid, sorbic acid and the like.

Such "antioxidants" include, for example, sulfites, ascorbic acid, α-tocopherol and the like.

Such "coloring agents" include, for example, food colors such as Food Color Yellow No. 5, Food Color Red No. 2, Food Color Blue No. 2 etc; food lake colors, red oxide and the like.

Such "sweetening agents" include, for example, saccharin sodium, dipotassium glycyrrhizinate, aspartame, stevia, thaumatin and the like.

Such "souring agents" include, for example, citric acid (citric anhydride), tartaric acid, malic acid and the like.

Such "bubbling agents" include, for example, sodium bicarbonate and the like.

Such "flavorings" may be synthetic substances or naturally occurring substances, and include, for example, lemon, lime, orange, menthol, strawberry and the like.

The compound of the present invention may be prepared as a preparation for oral administration in accordance with a method known per se, by, for example, compression-shaping in the presence of a carrier such as an excipient, a disintegrant, a binder, a lubricant, or the like, and subsequently coating the preparation as necessary by a method known per se for the purpose of taste masking, enteric dissolution or sustained release. For an enteric-coated preparation, an intermediate layer may be provided by a method known per se between the enteric layer and the drug-containing layer for the purpose of separation of the two layers.

For preparing the compound (I) or a salt thereof of the present invention as an orally disintegrating tablet, available methods include, for example, a method in which a core containing crystalline cellulose and lactose is coated with the compound (I) or a salt thereof of the present invention and, where necessary, a basic inorganic salt, and then further coated with a coating layer containing a water-soluble polymer to give a composition, which is coated with an enteric coating layer containing polyethylene glycol, further coated with an enteric coating layer containing triethyl citrate, still further coated with an enteric coating layer containing polyethylene glycol, and finally coated with mannitol to give fine granules, which are mixed with additives and shaped.

The above-mentioned "enteric coating layer" includes, for example, a layer consisting of a mixture of one or more kinds from aqueous enteric polymer substrates such as cellulose acetate phthalate (CAP), hydroxypropylmethyl cellulose phthalate, hydroxymethyl cellulose acetate succinate, methacrylic acid copolymers (e.g., Eudragit L30D-55 (trade name; produced by Rohm), Colicoat MAE30DP (trade name; produced by BASF), Polyquid PA30 (trade name; produced by Sanyo Chemical) etc), carboxymethylethyl cellulose, shellac and the like; sustained-release substrates such as methacrylic acid copolymers (e.g., Eudragit NE30D (trade name), Eudragit RL30D (trade name), Eudragit RS30D (trade name), etc.) and the like; water-soluble polymers; plasticizers such as triethyl citrate, polyethylene glycol, acetylated monoglycerides, triacetin, castor oil etc.; and the like; and the like.

The above-mentioned "additive" includes, for example, water-soluble sugar alcohols (e.g., sorbitol, mannitol, maltitol, reduced starch saccharides, xylitol, reduced palatinose, erythritol, etc.), crystalline cellulose (e.g., Ceolas KG 801, Avicel PH 101, Avicel PH 102, Avicel PH 301, Avicel PH 302, Avicel RC-591 (crystalline cellulose carmellose sodium) etc), low-substituted hydroxypropyl cellulose (e.g., LH-22, LH-32, LH-23, LH-33 (Shin-Etsu Chemical), mixtures thereof etc) and the like. Furthermore, binders, souring agents, bubbling agents, sweetening agents, flavorings, lubricants, coloring agents, stabilizers, excipients, disintegrants etc. are also used.

The compound of the present invention may be used in combination with 1 to 3 other active ingredients.

Such "other active ingredients" include, for example, an antibacterial agent (e.g., anti-*Helicobacter pylori* active substances, imidazole compounds, bismuth salts, quinolone compounds, etc.), acid suppressant, anti-cancer agent, anti-inflammatory agents such as nonsteroidal anti-inflammatory drug (NSAID) and the like. As the "other active ingredients", antibacterial agents are preferable, of which preferred are anti-*Helicobacter pylori* active substances, imidazole compounds and the like.

Such "anti-*Helicobacter pylori* active substances" include, for example, antibiotic penicillins (e.g., amoxicillin, benzylpenicillin, piperacillin, mecillinam, etc.), antibiotic cefems (e.g., cefixime, cefaclor, etc.), antibiotic macrolides (e.g., erythromycin, clarithromycin, etc.), antibiotic tetracyclines (e.g., tetracycline, minocycline, streptomycin, etc.), antibiotic aminoglycosides (e.g., gentamicin, amikacin, etc.), imipenem and so forth. Of these substances, preferred are antibiotic penicillins, antibiotic macrolides and the like. Particularly, a combined use of compound (I) or a salt thereof of the present invention with antibiotic penicillin (particularly amoxicillin) and antibiotic macrolides (particularly clarithromycin) is preferable.

Such "imidazole compounds" include, for example, metronidazole, miconazole and the like. Specifically, a combined use with metronidazole is preferable.

Such "bismuth salts" include, for example, bismuth acetate, bismuth citrate and the like.

Such "quinolone compounds" include, for example, ofloxacin, ciploxacin and the like.

Particularly, a combined use of the compound of the present invention with an antibacterial agent is preferable. More specifically, a combined use of the compound of the present invention with clarithromycin and/or metronidazole is preferable.

Such "other active ingredients" and the compound (I) or a salt thereof of the present invention may be mixed, prepared as a single pharmaceutical composition [e.g., tablets, powders, granules, capsules (including soft capsules), liquids, injectable preparations, suppositories, sustained-release preparations, etc.], in accordance with a commonly known method, and used in combination, and may also be prepared as separate preparations and administered to the same subject simultaneously or at a time interval.

EXAMPLES

The present invention is explained in detail in the following by referring to Reference Examples and Examples. The present invention is not limited by the Examples.

In the following Reference Examples and Examples, room temperature means about 15-30° C.

$^1$H-NMR spectra were determined with $CDCl_3$, $DMSO-d_6$ and $CD_3OD$ as the solvent using Varian Gemini-200 and Mercury-300; data are shown in chemical shift δ (ppm) from the internal standard tetramethylsilane.

Other symbols in the present specification mean the following.
s: singlet
d: doublet
t: triplet
q: quartet
m: multiplet
br: broad
bs: broad singlet
bm: broad multiplet
J: coupling constant Reference Example 1

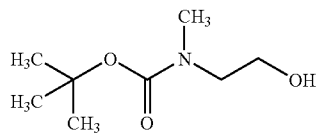

tert-Butyl 2-hydroxyethyl(methyl)carbamate

To a mixture of 2-(methylamino)ethanol (30.04 g) and ethyl acetate (90 mL) was dropwise added a mixture of di-tert-butyl dicarbonate (87.30 g) and ethyl acetate (10 mL) under ice-cooling. After stirring at room temperature for 2 hrs., the mixture was concentrated under reduced pressure. The residue was dissolved in ethyl acetate (150 mL), washed with water (100 mL) and dried over anhydrous magnesium sulfate. Concentration under reduced pressure gave the title compound (66.19 g) as a colorless oil.

$^1$H-NMR($CDCl_3$): 1.47(9H,s), 2.92(3H,s), 3.40(2H,t, J=5.1 Hz), 3.72-3.80(2H,m).

Reference Example 2

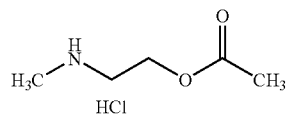

2-(Methylamino)ethyl acetate hydrochloride

To a mixture of 2-(methylamino)ethanol (1.50 g) and ethyl acetate (20 mL) was added di-tert-butyl dicarbonate (4.37 g) under ice-cooling. After stirring under ice-cooling for 1.5 hrs., acetic anhydride (2.08 mL), pyridine (1.78 mL) and 4-dimethylaminopyridine (0.12 g) were added. After stirring at room temperature for 2 hrs., ethyl acetate (50 mL) was added to the reaction mixture, and the mixture was washed with water (50 mL), a 5% aqueous citric acid solution (50 mL) and saturated brine (50 mL). After drying over anhydrous magnesium sulfate, the mixture was concentrated under reduced pressure. To the residue was added a 4N hydrogen chloride-ethyl acetate solution (20 mL), and the mixture was stirred at room temperature for 2 hrs. Diethyl ether (10 mL) was added, and the precipitated solid was collected by filtration. The solid was dried under reduced pressure to give the title compound (2.93 g) as a white solid.

$^1$H-NMR($DMSO-d_6$): 2.07(3H,s), 2.53(3H,s), 3.12-3.17 (2H,m), 4.24-4.30(2H,m), 9.29(2H,br).

Reference Example 3

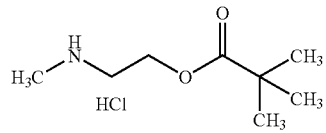

2-(Methylamino)ethyl trimethylacetate hydrochloride

To a mixture of tert-butyl 2-hydroxyethyl(methyl)carbamate (1.75 g) obtained in Reference Example 1 and ethyl acetate (15 mL) was added triethylamine (1.67 mL) and a mixture of trimethylacetyl chloride (1.35 mL), and ethyl acetate (5 mL) was dropwise added. After stirring at room temperature for 2 hrs., pyridine (1.62 mL) was added, and the mixture was stirred overnight at room temperature. Ethyl acetate (50 mL) was added to the reaction mixture, and the mixture was washed with water (50 mL), a 5% aqueous citric acid solution (50 mL) and saturated brine (50 mL), and dried over anhydrous magnesium sulfate. After concentration under reduced pressure, a 4N hydrogen chloride-ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.65 g) as a white solid.

¹H-NMR(DMSO-d₆): 1.18(9H,s), 2.56(3H,s), 3.17(2H,t, J=10.5 Hz), 4.22-4.28(2H,m), 9.19(2H,br).

Reference Example 4

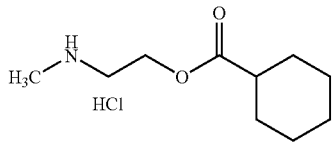

2-(Methylamino)ethyl cyclohexanecarboxylate hydrochloride

To a mixture of tert-butyl 2-hydroxyethyl (methyl)carbamate (1.75 g) obtained in Reference Example 1 and ethyl acetate (20 mL) were added pyridine (0.97 mL) and 4-dimethylaminopyridine (catalytic amount), and cyclohexanecarbonyl chloride (1.60 mL) was dropwise added. After stirring at room temperature for 2 hrs., pyridine (0.65 mL) and cyclohexanecarbonyl chloride (0.58 mL) were added, and the mixture was stirred overnight at room temperature. Ethyl acetate (50 mL) was added to the reaction mixture, and the mixture was washed with water (50 mL), a 5% aqueous citric acid solution (50 mL) and saturated brine (50 mL), and dried over anhydrous magnesium sulfate. After concentration under reduced pressure, a 4N hydrogen chloride-ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.88 g) as a white solid.

¹H-NMR(DMSO-d₆): 1.10-1.45(5H,m), 1.54-1.73(3H, m), 1.83-1.93(2H,m), 2.29-2.42(1H,m), 2.54(3H,s), 3.12-3.18(2H,m), 4.23-4.29(2H,m), 9.23(2H,br).

Reference Example 5

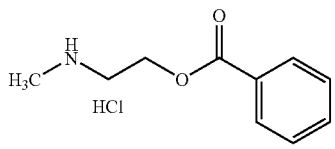

2-(Methylamino)ethyl benzoate hydrochloride

To a mixture of 2-(methylamino)ethanol (30.04 g) and ethyl acetate (90 mL) was dropwise added a mixture of di-tert-butyl dicarbonate (87.30 g) and ethyl acetate (10 mL) under ice-cooling. After stirring at room temperature for 1 hr., benzoyl chloride (61.8 g) and pyridine (38.8 mL) were added under ice-cooling. After stirring at room temperature for 1 hr., a solid was filtered off. The solid was washed with ethyl acetate (100 mL) and the filtrate and the washing were combined, which was washed with water (100 mL) and saturated brine (100 mL). After drying over anhydrous magnesium sulfate, the mixture was concentrated under reduced pressure. The residue was dissolved in ethyl acetate (100 mL), a 4N hydrogen chloride-ethyl acetate solution (200 mL) was added, and the mixture was stirred at room temperature for 30 min. Diethyl ether (100 mL) was added and a solid was collected by filtration. The solid was washed twice with ethyl acetate (100 mL) and dried under reduced pressure at 60° C. to give the title compound (57.4 g) as a white solid.

¹H-NMR(DMSO-d₆): 2.62(3H,s), 3.32(2H,m), 4.53(2H,t, J=9.9 Hz), 7.51-7.57(2H,m), 7.68(1H,m), 8.11(2H,d,J=7.8 Hz), 9.26(2H,bs).

Reference Example 6

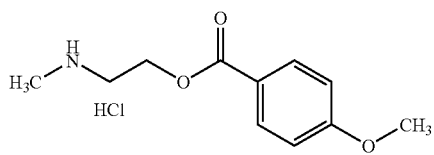

2-(Methylamino)ethyl 4-methoxybenzoate hydrochloride

To a mixture of tert-butyl 2-hydroxyethyl (methyl)carbamate (1.75 g) obtained in Reference Example 1 and ethyl acetate (10 mL) were added 4-methoxybenzoyl chloride (1.88 g) and pyridine (0.97 mL). After stirring at room temperature for 14 hrs., 4-methoxybenzoyl chloride (0.70 g) and pyridine (0.97 mL) were added and the mixture was stirred 15 at room temperature for 1 hr. Ethyl acetate (80 mL) was added to the reaction mixture, and the mixture was washed with water (20 mL), a saturated aqueous sodium hydrogen carbonate solution (20 mL) and water (20 mL), and dried over anhydrous magnesium sulfate. After concentration under reduced pressure, the residue was dissolved in ethyl acetate (10 mL), and a 4N hydrogen chloride-ethyl acetate solution (10 mL) was added. After stirring at room temperature for 1 hr., diethyl ether (20 mL) was added, and the precipitated solid was collected by filtration. The solid was washed twice with ethyl acetate (15 mL) and dried under reduced pressure at 60° C. to give the title compound (1.99 g) as a white solid.

¹H-NMR(DMSO-d₆): 2.62(3H,s), 3.32(2H,m), 4.48(2H,t, J=5.0 Hz), 7.07(2H,d,J=8.7 Hz), 8.06(2H,d,J=8.7 Hz), 9.04 (2H,bs).

Reference Example 7

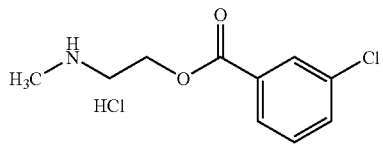

2-(Methylamino)ethyl 3-chlorobenzoate hydrochloride

To a mixture of tert-butyl 2-hydroxyethyl (methyl)carbamate (1.75 g) obtained in Reference Example 1 and ethyl acetate (10 mL) were added 3-chlorobenzoyl chloride (1.92 g) and pyridine (0.97 mL). After stirring at room temperature for 1 hr., the mixture was stirred at 60° C. for 6 hrs. Ethyl acetate (80 mL) was added to the reaction mixture, and the mixture was washed with water (20 mL), a saturated aqueous sodium hydrogen carbonate solution (20 mL) and water (20 mL), and dried over anhydrous magnesium sulfate. After concentration under reduced pressure, a 4N hydrogen chloride-ethyl acetate solution (10 mL) was added to the residue.

After stirring at room temperature for 22 hrs., diethyl ether (15 mL) was added, and the precipitated solid was collected by filtration. The solid was washed twice with ethyl acetate (15 ml) and dried under reduced pressure at 60° C. to give the title compound (2.01 g) as a white solid.

$^1$H-NMR(DMSO-d$_6$): 2.63(3H,s), 3.32(2H,m), 4.53(2H,t, J=4.9 Hz), 7.60(1H,t,J=8.0 Hz), 7.78(1H,d,J=8.0 Hz), 8.05 (1H,d,J=8.0 Hz), 8.15(1H,s), 9.07(2H,bs).

Reference Example 8

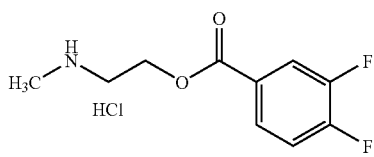

2-(Methylamino)ethyl 3,4-difluorobenzoate hydrochloride

To a mixture of tert-butyl 2-hydroxyethyl(methyl)carbamate (1.75 g) obtained in Reference Example 1 and ethyl acetate (10 mL) were added 3,4-difluorobenzoyl chloride (1.77 g) and pyridine (0.97 mL). After stirring at room temperature for 3 days, ethyl acetate (80 mL) was added to the reaction mixture. The mixture was washed with water (20 mL), a saturated aqueous sodium hydrogen carbonate solution (20 mL) and water (20 mL), and dried over anhydrous magnesium sulfate. After concentration under reduced pressure, a 4N hydrogen chloride-ethyl acetate solution (10 mL) was added to the residue. After stirring at room temperature for 4 hrs, the mixture was concentrated under reduced pressure. The residue was washed with ethyl acetate (15 mL), and dried under reduced pressure at 60° C. to give the title compound (2.05 g) as a white solid.

$^1$H-NMR(DMSO-d$_6$): 2.62(3H,s), 3.32(2H,m), 4.53(2H,t, J=5.0 Hz), 7.64(1H,m), 8.00(1H,m), 8.25(1H,m), 9.25(2H, bs).

Reference Example 9

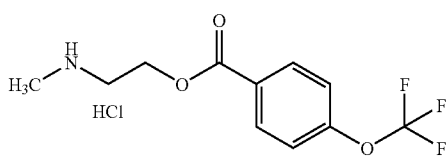

2-(Methylamino)ethyl 4-trifluoromethoxybenzoate hydrochloride

To a mixture of tert-butyl 2-hydroxyethyl (methyl)carbamate (1.30 g) obtained in Reference Example 1 and ethyl acetate (10 mL) were added 4-trifluoromethoxybenzoyl chloride (1.83 g) and pyridine (0.72 mL). The mixture was stirred at 60° C. for 25 hrs. Ethyl acetate (60 mL) was added to the reaction mixture, and the mixture was washed with water (30 mL), a saturated aqueous sodium hydrogen carbonate solution (20 mL) and water (20 mL), and dried over anhydrous magnesium sulfate. After concentration under reduced pressure, a 4N hydrogen chloride-ethyl acetate solution (10 mL) was added to the residue. After stirring at room temperature for 14.5 hrs., the mixture was concentrated under reduced pressure. The residue was washed twice with ethyl acetate (15 mL), and dried under reduced pressure at 60° C. to give the title compound (1.83 g) as a white solid.

$^1$H-NMR(DMSO-d$_6$): 2.63(3H,s), 3.31(2H,m), 4.54(2H,t, J=4.9 Hz), 7.55(2H,d,J=8.5 Hz), 8.24(2H,d,J=8.5 Hz), 9.02 (2H,bs).

Reference Example 10

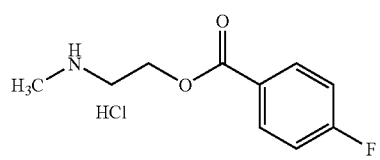

2-(Methylamino)ethyl 4-fluorobenzoate hydrochloride

To a mixture of tert-butyl 2-hydroxyethyl (methyl)carbamate (1.75 g) obtained in Reference Example 1 and ethyl acetate (10 mL) were added 4-fluorobenzoyl chloride (1.74 g) and pyridine (0.97 mL). The mixture was stirred at room temperature for 6.5 hrs. Ethyl acetate (80 mL) was added to the reaction mixture, and the mixture was washed with water (30 mL), a saturated aqueous sodium hydrogen carbonate solution (30 mL), water (30 mL) and saturated brine (30 mL), and dried over anhydrous magnesium sulfate. After concentration under reduced pressure, a 4N hydrogen chloride-ethyl acetate solution (10 mL) was added to the residue. After stirring at room temperature for 1 hr., the precipitated solid was collected by filtration. The solid was washed twice with ethyl acetate (15 mL) and dried under reduced pressure at 60° C. to give the title compound (1.89 g) as a white solid.

$^1$H-NMR(DMSO-d$_6$): 2.62(3H,s), 3.32(2H,m), 4.52(2H,t, J=4.9 Hz), 7.34-7.44(2H,m), 8.16-8.24(2H,m), 9.18(2H,bs).

Reference Example 11

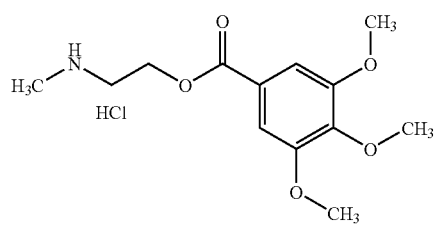

2-(Methylamino)ethyl 3,4,5-trimethoxybenzoate hydrochloride

To a mixture of tert-butyl 2-hydroxyethyl (methyl)carbamate (1.75 g) obtained in Reference Example 1 and ethyl acetate (10 mL) were added 3,4,5-trimethoxybenzoyl chloride (2.54 g) and pyridine (0.97 mL). After stirring at 60° C. for 14 hrs., 3,4,5-trimethoxybenzoyl chloride (1.30 g), pyridine (0.97 mL) and ethyl acetate (10 mL) were added, and the mixture was stirred at 60° C. for 24 hrs. The reaction mixture was filtered and ethyl acetate (50 mL) and water (30 mL) were added to the filtrate. After partitioning, ethyl acetate layer was washed with 1N hydrochloric acid (30 mL), water (30 mL), an aqueous copper (II) sulfate solution (30 mL), water (30 mL) and saturated brine (30 mL), and dried over anhydrous magnesium sulfate. After concentration under reduced pressure, the residue was purified by silica gel column chromatography (eluted with ethyl acetate:hexane=1:1). A 4N hydrogen chloride-ethyl acetate solution (10 mL) was added to the purified product. After stirring at room temperature for 4 hrs, the mixture was concentrated under reduced pressure. Toluene (10 mL) was added, and the mixture was concentrated under reduced pressure. The residue was suspended in ethyl acetate, and the solid was filtrated. After washing with ethyl acetate (15 mL), the solid was dried under reduced pressure to give the title compound (1.79 g) as a white solid.

$^1$H-NMR(DMSO-d$_6$): 2.61(3H,s), 3.28-3.35(2H,m), 3.74 (3H,s) 3.87(6H,s), 4.48-4.54(2H,m), 7.40(2H,s), 9.43(2H,br).

Reference Example 12

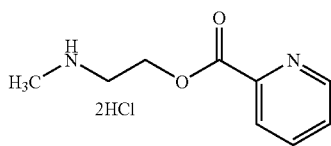

2-(Methylamino)ethyl 2-pyridinecarboxylate dihydrochloride

To a solution (100 mL) of tert-butyl 2-hydroxyethyl (methyl)carbamate (1.75 g) obtained in Reference Example 1, 2-pyridinecarbonyl chloride hydrochloride (2.67 g), pyridine (1.21 mL) and 4-dimethylaminopyridine (0.122 g) in tetrahydrofuran was dropwise added triethylamine (2.09 mL) under ice-cooling, and the mixture was stirred at room temperature for 6 hrs. Water (200 mL) was added to the reaction mixture and the mixture was extracted with ethyl acetate (150 mL). The organic layer was washed successively with a 5% aqueous copper (II) sulfate solution (100 mL), water (100 mL) and saturated brine (100 mL), dried over anhydrous sodium sulfate and evaporated under reduced pressure. The residue was dissolved in ethyl acetate (50 mL) and ethanol (100 mL), and a 4N hydrogen chloride-ethyl acetate solution (15 mL) was added. The mixture was stirred at room temperature for 1 hr. The precipitated solid was collected by filtration, washed twice with ethyl acetate (100 mL), and dried under reduced pressure at 60° C. to give the title compound (1.08 g) as a white solid.

$^1$H-NMR(DMSO-d$_6$): 2.62(3H,t,J=5.4 Hz), 3.35(2H,m), 4.63(2H,t,J=5.0 Hz), 5.26(1H,bs), 7.77-7.84(1H,m), 8.14-8.18(1H,m), 8.36-8.40(1H,m), 8.70-8.90(1H,m), 9.48(2H,br).

Reference Example 13

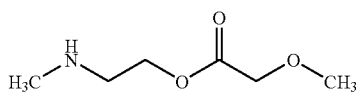

2-(Methylamino)ethyl methoxyacetate

To a mixture of tert-butyl 2-hydroxyethyl (methyl)carbamate (1.75 g) obtained in Reference Example 1 and ethyl acetate (10 mL) were added methoxyacetyl chloride (1.20 g) and pyridine (0.97 mL). After stirring for 2 hrs., ethyl acetate (70 mL) was added to the reaction mixture. The mixture was washed with water (20 mL), a saturated aqueous sodium hydrogen carbonate solution (20 mL) and water (20 mL), and dried over anhydrous magnesium sulfate. After concentration under reduced pressure, the residue was dissolved in ethyl acetate (5 mL), and a 4N hydrogen chloride-ethyl acetate solution (10 mL) was added. After stirring at room temperature for 1 hr., the mixture was concentrated under reduced pressure. Water (60 mL) and diethyl ether (30 mL) were added to the residue. After stirring, the aqueous layer was separated and taken. The aqueous layer was basified with sodium hydrogen carbonate and extracted twice with ethyl acetate (40 mL). The ethyl acetate layer was dried over anhydrous magnesium sulfate and concentrated under reduced pressure to give the title compound (1.00 g) as a colorless oil.

$^1$H-NMR(CDCl$_3$): 2.40(1H,bs), 3.06(3H,s), 3.44(3H,s), 3.57(2H,t,J=5.1 Hz), 3.75-3.82(2H,m), 4.13(2H,s).

Reference Example 14

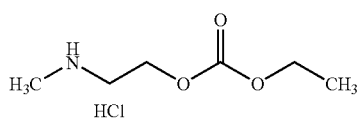

Ethyl 2-(methylamino)ethyl carbonate hydrochloride

To a mixture of tert-butyl 2-hydroxyethyl (methyl) carbamate (1.75 g) obtained in Reference Example 1 and ethyl acetate (20 mL) were added pyridine (0.97 mL) and 4-dimethylaminopyridine (catalytic amount), and ethyl chlorocarbonate (1.25 mL) was dropwise added. The mixture was stirred overnight at room temperature and ethyl acetate (50 mL) was added. The mixture was washed with water (50 mL), a 5% aqueous citric acid solution (50 mL) and saturated brine (50 mL), and dried over anhydrous magnesium sulfate. After concentration under reduced pressure, a 4N hydrogen chloride-ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.66 g) as a white solid.

$^1$H-NMR(DMSO-d$_6$): 1.23(3H,t,J=7.1 Hz), 2.54(3H,s), 3.16-3.22(2H,m), 4.15(2H,q,J=7.1 Hz), 4.32-4.37(2H,m), 9.25(2H,br).

Reference Example 15

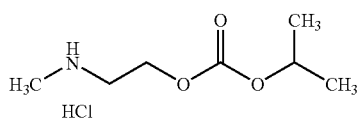

Isopropyl 2-(methylamino)ethyl carbonate hydrochloride

To a mixture of tert-butyl 2-hydroxyethyl (methyl)carbamate (3.50 g) obtained in Reference Example 1 and ethyl acetate (20 mL) were added isopropyl chlorocarbonate (1.35 g) and pyridine (1.94 mL) under ice-cooling. After stirring under ice-cooling for 3.5 hrs., isopropyl chlorocarbonate (1.84 g) was added, and the mixture was stirred at room temperature for 2.5 hrs. Ethyl acetate (120 mL) was added to the reaction mixture, and the mixture was washed with water (50 mL) and saturated brine (50 mL), and dried over anhydrous magnesium sulfate. After concentration under reduced pressure, a 4N hydrogen chloride-ethyl acetate solution (10 mL) was added to the residue. After stirring at room temperature for 2 hrs., the precipitated solid was collected by filtration. The solid was washed with ethyl acetate (15 mL), and dried under reduced pressure at 60° C. to give the title compound (1.38 g) as a white solid.

$^1$H-NMR(DMSO-$d_6$): 1.25(6H,d,J=6.2 Hz), 2.56(3H,s), 3.20(2H,t,J=5.1 Hz), 4.32(2H,t,J=5.1 Hz), 4.80(1H,m), 8.95 (2H,bs).

Reference Example 16

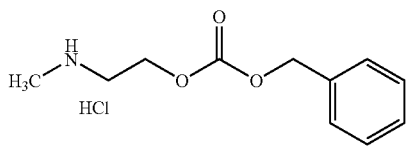

Benzyl 2-(methylamino)ethyl carbonate hydrochloride

To a mixture of tert-butyl 2-hydroxyethyl (methyl)carbamate (1.75 g) obtained in Reference Example 1 and ethyl acetate (20 mL) were added pyridine (0.97 mL) and 4-dimethylaminopyridine (catalytic amount), and benzyl chlorocarbonate (1.57 mL) was dropwise added. After stirring at room temperature for 2 hrs., pyridine (0.65 mL) and benzyl chlorocarbonate (1.28 mL) were added. After stirring at room temperature for 5 days, pyridine (0.81 mL) was added under ice-cooling and a solution (5 mL) of benzyl chlorocarbonate (1.43 mL) in ethyl acetate was dropwise added slowly. After stirring at room temperature for 2 hrs., ethyl acetate (50 mL) was added to the mixture, washed with water (50 mL), a 5% aqueous citric acid solution (50 mL) and saturated brine (50 mL), and dried over anhydrous magnesium sulfate. After concentration under reduced pressure, a 4N hydrogen chloride-ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.99 g) as a white solid.

$^1$H-NMR(DMSO-$d_6$): 2.55(3H,s), 3.21(2H,t,J=5.1 Hz), 4.37(2H,t,J=5.1 Hz), 5.18(2H,s), 7.30-7.50(5H,m), 9.07(2H, br).

Reference Example 17

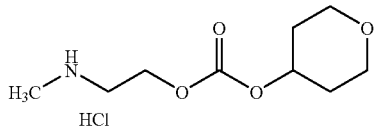

2-(Methylamino)ethyl tetrahydropyran-4-yl carbonate hydrochloride

To a solution (40 mL) of bis(trichloromethyl)carbonate (2.97 g) in tetrahydrofuran was dropwise added a solution (10 mL) of pyridine (2.43 mL) in tetrahydrofuran under ice-cooling. After stirring under ice-cooling for 10 min., a solution (20 mL) of tetrahydropyran-4-ol (1.91 g) in tetrahydrofuran was dropwise added slowly. After stirring at room temperature for 2 hrs., the mixture was concentrated under reduced pressure, and ethyl acetate (50 mL) and water (50 mL) were added to the residue. The ethyl acetate layer was separated and taken, washed with 0.2N hydrochloric acid (20 mL) and saturated brine (50 mL), and dried over anhydrous magnesium sulfate. Concentration under reduced pressure gave tetrahydropyran-4-yl chlorocarbonate (1.53 g). To a mixture of tert-butyl 2-hydroxyethyl(methyl)carbamate (1.40 g) obtained in Reference Example 1 and tetrahydrofuran (20 mL) was added pyridine (0.78 mL), and a solution (10 mL) of tetrahydropyran-4-yl chlorocarbonate (1.53 g) obtained above in tetrahydrofuran was dropwise added, and the mixture was stirred overnight at room temperature. After concentration of the reaction mixture under reduced pressure, water (50 mL) was added, the mixture was extracted with ethyl acetate (50 mL). The residue was washed with a 5% aqueous citric acid solution (50 mL) and saturated brine (50 mL), and dried over anhydrous magnesium sulfate. After concentration under reduced pressure, the residue was purified by silica gel column chromatography (eluted with ethyl acetate:hexane=4:1, then 3:2). The obtained colorless oil (2.03 g) was dissolved in diethyl ether (2 mL), and a 4N hydrogen chloride-ethyl acetate solution (5 mL) was added. After stirring at room temperature for 30 min., diethyl ether (10 mL) was added and the mixture was stirred overnight. The precipitated solid was collected by filtration and dried under reduced pressure to give the title compound (1.20 g) as a white solid.

$^1$H-NMR(DMSO-$d_6$): 1.50-1.65(2H,m), 1.87-1.98(2H, m), 2.54(3H,s), 3.20(2H,m), 3.40-3.50(2H,m), 3.74-3.83 (2H,m), 4.36(2H,t,J=5.1 Hz), 4.72-4.83(1H,m), 9.32(2H,br).

Reference Example 18

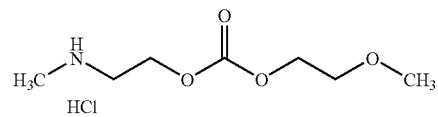

2-Methoxyethyl 2-(methylamino)ethyl carbonate hydrochloride

To a mixture of tert-butyl 2-hydroxyethyl (methyl)carbamate (1.75 g) obtained in Reference Example 1 and ethyl acetate (20 mL) was added pyridine (1.62 mL) and a solution (5 mL) of 2-methoxyethyl chlorocarbonate (2.77 g) in ethyl acetate was dropwise added slowly, and the mixture was stirred overnight at room temperature. After concentration of the reaction mixture under reduced pressure, water (50 mL) was added, the mixture was extracted with ethyl acetate (50 mL). The mixture was washed with 5% aqueous citric acid solution (50 mL) and saturated brine (50 mL), and dried over anhydrous magnesium sulfate. After concentration under reduced pressure, the residue was dissolved in diethyl ether (2 mL), and a 4N hydrogen chloride-ethyl acetate solution (5 mL) was added. After stirring at room temperature for 30 min., diethyl ether (10 mL) was added, and the mixture was stirred overnight. The precipitated solid was collected by filtration, and dried under reduced pressure to give the title compound (1.56 g) as a white solid.

$^1$H-NMR(DMSO-$d_6$): 2.54(3H,s), 3.19(2H,m), 3.26(3H, s), 3.52-3.57(2H,m), 4.20-4.25(2H,m), 4.33-4.39(2H,m), 9.26(2H,br).

Reference Example 19

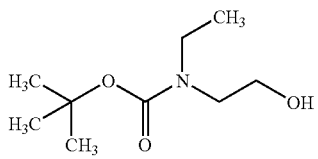

tert-Butyl ethyl(2-hydroxyethyl)carbamate

To a mixture of 2-(ethylamino)ethanol (8.91 g) and ethyl acetate (100 mL) was added di-tert-butyl dicarbonate (21.8 g) under ice-cooling. After stirring at room temperature for 3 days, the mixture was washed with saturated brine (100 mL), and dried over anhydrous magnesium sulfate. Concentration under reduced pressure gave the title compound (19.0 g) as a colorless oil.
$^1$H-NMR(CDCl$_3$): 1.11(3H,t,J=7.0 Hz), 1.47(9H,s), 3.27 (2H,q,J=7.0 Hz), 3.37(2H,t,J=5.2 Hz), 3.73(2H,q,J=5.2 Hz).

Reference Example 20

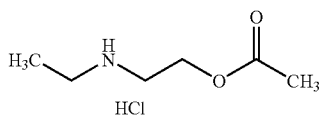

2-(Ethylamino)ethyl acetate hydrochloride

To a mixture of tert-butyl ethyl(2-hydroxyethyl)carbamate (1.89 g) obtained in Reference Example 19 and ethyl acetate (20 mL) were added acetic anhydride (1.04 mL), pyridine (0.89 mL) and 4-dimethylaminopyridine (0.061 g). After stirring at room temperature for 3 hrs., ethyl acetate (50 mL) was added, and the mixture was washed with water (50 mL), a 5% aqueous citric acid solution (50 mL) and saturated brine (50 mL). After drying over anhydrous magnesium sulfate, the mixture was concentrated under reduced pressure. A 4N hydrogen chloride-ethyl acetate solution (10 mL) was added to the residue, and the mixture was stirred at room temperature for 1 hr. Ethyl acetate (10 mL) and diethyl ether (20 mL) were added, and the precipitated solid was collected by filtration. The solid was dried under reduced pressure to give the title compound (1.54 g) as a white solid.
$^1$H-NMR(DMSO-d$_6$): 1.22(3H,t,J=7.3 Hz), 2.07(3H,s), 2.95(2H,q,J=7.3 Hz), 3.15(2H,t,J=5.3 Hz), 4.24-4.30(2H,m), 9.17(2H,br).

Reference Example 21

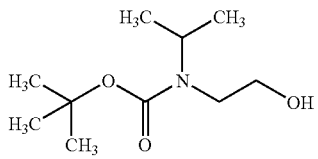

tert-Butyl 2-hydroxyethyl(isopropyl)carbamate

To a solution (30 mL) of 2-(isopropylamino)ethanol (10.0 g) in tetrahydrofuran was added di-tert-butyl dicarbonate (22.2 g), and the mixture was stirred at room temperature for 1 hr. The reaction mixture was concentrated under reduced pressure and water (100 mL) was added to the residue. The mixture was extracted with ethyl acetate (200 mL). The ethyl acetate layer was washed with saturated brine (100 mL), dried over anhydrous sodium sulfate and concentrated under reduced pressure to give the title compound (21.21 g) as a colorless oil.
$^1$H-NMR(CDCl$_3$): 1.12(6H,d,J=6.6 Hz), 3.30(2H,t,J=5.0 Hz) 3.71(2H,t,J=5.0 Hz), 3.80-4.30(1H,m).

Reference Example 22

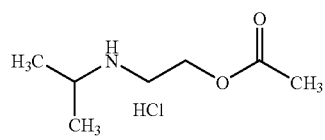

2-(Isopropylamino)ethyl acetate hydrochloride

To a solution (15 mL) of tert-butyl 2-hydroxyethyl (isopropyl)carbamate (5.0 g) obtained in Reference Example 21 in tetrahydrofuran were added pyridine (6.0 mL) and acetic anhydride (2.79 mL) and the mixture was stirred at room temperature for 18 hrs. The reaction mixture was concentrated under reduced pressure, water (50 mL) was added to the residue, and the mixture was extracted with ethyl acetate (100 mL). The ethyl acetate layer was washed with a 5% aqueous citric acid solution (50 mL) and saturated brine (50 mL), dried over anhydrous sodium sulfate and concentrated under reduced pressure. The obtained colorless oil was dissolved in a 4N hydrogen chloride-ethyl acetate solution (10 mL), and the mixture was stirred at room temperature for 1 hr. The precipitated solid was collected by filtration, and dried under reduced pressure to give the title compound (3.14 g) as a colorless solid.
$^1$H-NMR(DMSO-d$_6$): 1.25(6H,d,J=6.6 Hz), 2.08(3H,s), 3.10-3.40(3H,m), 4.29(2H,t,J=6.0 Hz), 9.11(2H,br).

Reference Example 23

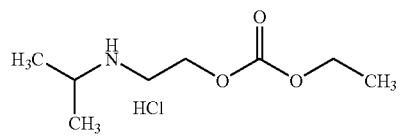

Ethyl 2-(isopropylamino)ethyl carbonate hydrochloride

To a solution (15 mL) of tert-butyl 2-hydroxyethyl (isopropyl)carbamate (5.0 g) obtained in Reference Example 21 in tetrahydrofuran were added pyridine (6.0 mL) and ethyl chlorocarbonate (2.81 mL) and the mixture was stirred at room temperature for 18 hrs. The reaction mixture was concentrated under reduced pressure, and water (50 mL) was added to the residue, and the mixture was extracted with ethyl acetate (100 mL). The ethyl acetate layer was washed with a 5% aqueous citric acid solution (50 mL) and saturated brine (50 mL), dried over anhydrous sodium sulfate and the mixture was concentrated under reduced pressure. The obtained colorless oil was dissolved in a 4N hydrogen chloride-ethyl acetate solution (10 mL), and the mixture was stirred at room temperature for 1 hr. The precipitated solid was collected by filtration and dried under reduced pressure to give the title compound (3.34 g) as a colorless solid.

$^1$H-NMR(DMSO-d$_6$): 1.20-1.30(9H,m), 3.10-3.40(3H, m), 4.17(2H,q,J=7.4 Hz), 4.37(2H,t,J=5.6 Hz), 9.13(2H,br).

Reference Example 24

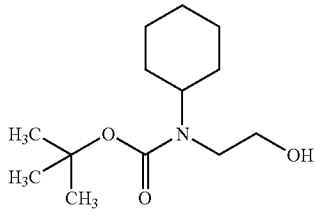

tert-Butyl cyclohexyl(2-hydroxyethyl)carbamate

To a solution (200 mL) of 2-(cyclohexylamino)ethanol (14.3 g) in ethanol was dropwise added di-tert-butyl dicarbonate (21.8 g). After stirring at room temperature for 2 days, the mixture was concentrated under reduced pressure. The residue was dissolved in ethyl acetate (200 mL), washed with water (100 mL) and saturated brine (100 mL), and dried over anhydrous sodium sulfate. Concentration under reduced pressure gave the title compound (24.2 g) as a colorless oil.

$^1$H-NMR(CDCl$_3$): 1.26-1.39(4H,m), 1.47(9H,s), 1.61-1.81(6H,m), 3.30-3.40(2H,m), 3.69(2H,t,J=5.4 Hz), 3.66-3.90(2H,br).

Reference Example 25

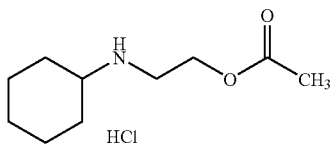

2-(Cyclohexylamino)ethyl acetate hydrochloride

To a solution (50 mL) of tert-butyl cyclohexyl(2-hydroxyethyl)carbamate (2.43 g) obtained in Reference Example 24 in tetrahydrofuran were added pyridine (1.05 mL), acetic anhydride (1.23 mL) and 4-dimethylaminopyridine (0.122 g) under ice-cooling, and the mixture was stirred at room temperature for 12 hrs. Ethyl acetate (100 mL) was added to the reaction mixture and the mixture was washed successively with a saturated aqueous sodium hydrogen carbonate solution (100 mL), a 5% aqueous copper (II) sulfate solution (100 mL) and saturated brine (100 mL), and dried over anhydrous sodium sulfate. The mixture was concentrated under reduced pressure. The residue was dissolved in ethyl acetate (15 mL), and a 4N hydrogen chloride-ethyl acetate solution (15 mL) was added. After stirring at room temperature for 3 hrs., diisopropyl ether (20 mL) was added, and the precipitated solid was collected by filtration to give the title compound (1.78 g) as a white solid.

$^1$H-NMR(DMSO-d$_6$): 1.05-2.03(10H,m), 2.07(3H,s), 2.90-3.10(1H,m), 3.17(2H,t,J=5.2 Hz), 4.29(2H,t,J=5.2 Hz), 9.19(2H,br).

Reference Example 26

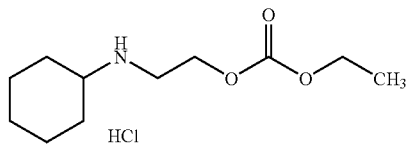

2-(Cyclohexylamino)ethyl ethyl carbonate hydrochloride

To a solution (50 mL) of tert-butyl cyclohexyl(2-hydroxyethyl)carbamate (2.43 g) obtained in Reference Example 24 in tetrahydrofuran were added pyridine (1.45 mL), ethyl chlorocarbonate (1.71 mL) and 4-dimethylaminopyridine (0.122 g) under ice-cooling, and the mixture was stirred at room temperature for 15 hrs. Ethyl acetate (100 mL) was added to the reaction mixture, and the mixture was washed successively with a saturated aqueous sodium hydrogen carbonate solution (100 mL), a 5% aqueous copper (II) sulfate solution (100 mL), water (100 mL) and saturated brine (100 mL), and dried over anhydrous sodium sulfate. The mixture was concentrated under reduced pressure and the residue was dissolved in ethyl acetate (15 mL). A 4N hydrogen chloride-ethyl acetate solution (15 mL) was added. After stirring at room temperature for 3 hrs., diisopropyl ether (20 mL) was added, and the precipitated solid was collected by filtration to give the title compound (2.12 g) as a white solid.

$^1$H-NMR(DMSO-d$_6$): 1.01-2.08(10H,m), 1.23(3H,t,J=7.0 Hz), 2.90-3.10(1H,m), 3.21(2H,t,J=5.2 Hz), 4.16(2H,q,J=7.0 Hz), 4.39(2H,t,J=5.2 Hz), 9.27(2H,br).

Reference Example 27

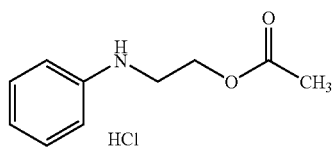

2-Anilinoethyl acetate hydrochloride

To a solution (700 mL) of 2-anilinoethanol (137 g) in tetrahydrofuran were added pyridine (97.1 mL), acetic anhydride (113.2 mL) and 4-dimethylaminopyridine (12.22 g) under ice-cooling, and the mixture was stirred at room temperature for 20 hrs. Ethyl acetate (1 L) was added to the reaction mixture and the mixture was washed successively with water (1 L), a saturated aqueous sodium hydrogen carbonate solution (1 L), a 5% aqueous copper (II) sulfate solution (1 L) and saturated brine (1 L), dried over anhydrous sodium sulfate, and evaporated under reduced pressure. To a solution of the obtained residue in ethyl acetate (700 mL) was added a 4N hydrogen chloride-ethyl acetate solution (250 mL) under ice-cooling, and the precipitated solid was collected by filtration to give the title compound (156 g) as a white solid.

$^1$H-NMR(CD$_3$OD): 2.11(3H,s), 3.71-3.76(2H,m), 4.32-4.37(2H,m), 7.49-7.64(5H,m).

Reference Example 28

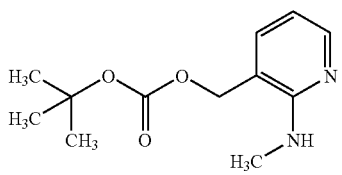

tert-Butyl[2-(methylamino)-3-pyridyl]methyl carbonate

To a solution (50 mL) of [2-(methylamino)-3-pyridyl]methanol (2 g: synthesized according to the method described in WO 01/32652) in tetrahydrofuran were added di-tert-butyl dicarbonate (3.48 g) and 4-dimethylaminopyridine (0.18 g) and the mixture was refluxed for 1 hr. Water (30 mL) was added to the reaction mixture and extracted with ethyl acetate (50 mL). The obtained organic layer was washed with saturated brine (50 mL), and dried over anhydrous sodium sulfate. The residue obtained by concentration under reduced pressure was purified by flash silica gel column chromatography (eluted with ethyl acetate:hexane=1:5) to give the title compound (1.51 g) as a white solid.

$^1$H-NMR(CDCl$_3$): 1.49(9H,s), 3.02(3H,d,J=4.8 Hz), 4.99 (2H,s), 5.00(1H,bs), 6.55(1H,dd,J=7.0, 5.0 Hz), 7.37(1H,dd, J=7.0, 1.8 Hz), 8.16(1H,dd,J=5.0, 1.8 Hz).

Reference Example 29

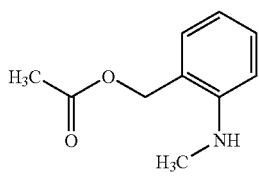

2-(Methylamino)benzyl acetate

To a solution (50 mL) of [2-(methylamino)phenyl]methanol (1.37 g: synthesized according to the method described in WO 01/32652) in tetrahydrofuran were added pyridine (1.05 mL), acetic anhydride (1.23 mL) and 4-dimethylaminopyridine (0.18 g), and the mixture was stirred at room temperature for 8 hrs. Water (100 mL) was added to the reaction mixture, and the mixture was extracted with ethyl acetate (100 mL). The organic layer was washed successively with a 5% aqueous copper (II) sulfate solution (50 mL), a saturated aqueous sodium hydrogen carbonate solution (50 mL) and saturated brine (50 mL), and dried over anhydrous sodium sulfate. The solvent was evaporated under reduced pressure and the obtained residue was purified by flash silica gel column chromatography (eluted with ethyl acetate:hexane=1:5, then 1:3) to give the title compound (0.38 g) as a white solid.

$^1$H-NMR(CDCl$_3$): 2.08(3H,s), 2.87(3H,s), 4.40(1H,br), 5.08(2H,s), 6.64-6.74(2H,m), 7.17-7.32(2H,m).

Reference Example 30

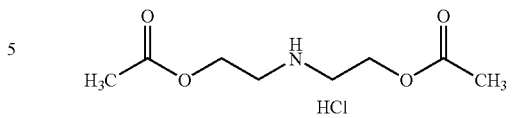

2-[(2-Acetyloxyethyl)amino]ethyl acetate hydrochloride

To a mixture of 2,2'-iminodiethanol (2.10 g) and ethyl acetate (20 mL) was added di-tert-butyl dicarbonate (4.37 g) under ice-cooling. After stirring for 1.5 hrs. under ice-cooling, acetic anhydride (2.08 mL), pyridine (1.78 ml) and 4-dimethylaminopyridine (0.12 g) were added. After stirring at room temperature for 2 hrs., ethyl acetate (50 mL) was added to the reaction mixture and the mixture was washed with water (50 mL), a 5% aqueous citric acid solution (50 ml) and saturated brine (50 mL). After drying over anhydrous magnesium sulfate, the mixture was concentrated under reduced pressure. A 4N hydrogen chloride-ethyl acetate solution (20 ml) was added to the residue, and the mixture was stirred at room temperature for 2 hrs. Diethyl ether (10 mL) was added, and the precipitated solid was collected by filtration. The solid was dried under reduced pressure to give the title compound (6.18 g) as a white solid.

$^1$H-NMR(DMSO-d$_6$): 2.07(6H,s), 3.23(4H,t,J=5.3 Hz), 4.27-4.33(4H,m), 9.40(2H,br).

Reference Example 31

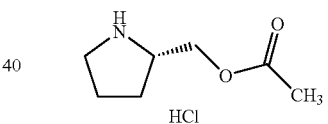

(S)-2-Pyrrolidinylmethyl acetate hydrochloride

To a mixture of (S)-2-pyrrolidinylmethanol (1.01 g) and ethyl acetate (0.10 mL) was added di-tert-butyl dicarbonate (2.18 g) under ice-cooling. After stirring for 1 hr. under ice-cooling, acetic anhydride (1.04 mL), pyridine (0.89 mL) and 4-dimethylaminopyridine (0.061 g) were added. After stirring at room temperature for 1 hr., ethyl acetate (50 mL) was added to the reaction mixture, and the mixture was washed with water (50 mL), a 5% aqueous citric acid solution (50 mL) and saturated brine (50 mL). After drying over anhydrous magnesium sulfate, the mixture was concentrated under reduced pressure. A 4N hydrogen chloride-ethyl acetate solution (10 mL) was added to the residue, and the mixture was stirred at room temperature for 1 hr. Diethyl ether (10 mL) was added and the precipitated solid was collected by filtration. The solid was dried under reduced pressure to give the title compound (1.68 g) as a pale-brown solid.

$^1$H-NMR(DMSO-d$_6$): 1.56-2.10(4H,m), 2.06(3H,s), 3.05-3.24(2H,m), 3.63-3.68(1H,m), 4.15(1H,dd,J=11.8, 8.1 Hz), 4.26(1H,dd,J=11.8, 4.1 Hz), 9.21(1H,br), 9.87(1H,br).

Reference Example 32

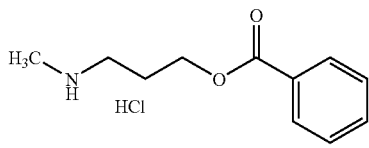

3-(Methylamino)propyl benzoate hydrochloride

To a mixture of 3-amino-1-propanol (0.75 g) and ethyl acetate (2.25 mL) was added a solution (0.25 mL) of di-tert-butyl dicarbonate (2.18 g) in ethyl acetate under ice-cooling. After stirring at room temperature for 21.5 hrs., benzoyl chloride (1.30 mL), pyridine (0.98 mL) and 4-dimethylaminopyridine (0.012 g) were added. After stirring at room temperature for 5 hrs., ethyl acetate (32.5 mL) was added to the reaction mixture, and the mixture was washed with water (12.5 mL) and saturated brine (12.5 mL). After drying over anhydrous magnesium sulfate, the mixture was concentrated under reduced pressure. The residue was dissolved in N,N-dimethylformamide (20 mL), and methyl iodide (5 mL) was added. 60% sodium hydride (0.4 g) was added under ice-cooling. After stirring at room temperature for 3 hrs., the reaction mixture was poured into an ice-cooled aqueous ammonium chloride solution (60 mL). The mixture was extracted with diethyl ether (80 mL) and washed with saturated brine (30 mL). After drying over anhydrous magnesium sulfate, the mixture was concentrated under reduced pressure. The residue was purified by silica gel column chromatography (ethyl acetate:hexane=2:1, then ethyl acetate, then acetone:ethyl acetate=1:9) to give 3-[(tert-butoxycarbonyl)(methyl)amino]propyl benzoate (2.52 g) as a colorless oil. A 4N hydrogen chloride-ethyl acetate solution (10 mL) was added, and the mixture was stirred at room temperature for 1 hr. After concentration under reduced pressure, ethyl acetate (10 mL) was added to the residue and the precipitated solid was collected by filtration. After washing with diethyl ether (10 mL), the solid was dried under reduced pressure to give the title compound (1.73 g) as a colorless solid.

$^1$H-NMR(DMSO-d$_6$): 2.02-2.16(2H,m), 2.56(3H,s), 3.05 (2H,t,J=7.3 Hz), 4.35(2H,t,J=6.1 Hz), 7.51(2H,m), 7.65-7.73 (1H,m), 8.01(2H,d,J=7.2 Hz), 8.95(2H,br).

Reference Example 33

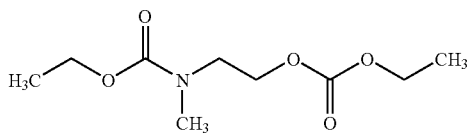

2-[(Ethoxycarbonyl)(methyl)amino]ethyl ethyl carbonate

To a solution (1000 mL) of 2-(methylamino)ethanol (100 g) in ethyl acetate was added pyridine (222 mL), ethyl chlorocarbonate (240 mL) was dropwise added over 2 hr. under ice-cooling. After the completion of the dropwise addition, the reaction mixture was stirred at room temperature for 18 hrs. Water (300 mL) was added, and the ethyl acetate layer was separated and washed with 1N hydrochloric acid (200 mL) and saturated brine (200 mL). After drying over anhydrous sodium sulfate, the mixture was concentrated under reduced pressure, and the residue was evaporated under reduced pressure to give the title compound (180 g) as a colorless fraction having a boiling point of 95-100° C. (pressure: 0.1-0.2 mmHg).

$^1$H-NMR(CDCl$_3$): 1.20-1.40(6H,m), 2.97(3H,s), 3.50-3.60(2H,m), 4.05-4.35(6H,m).

Reference Example 34

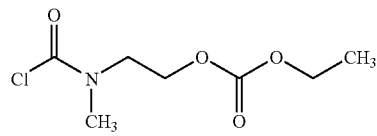

2-[(Chlorocarbonyl)(methyl)amino]ethyl ethyl carbonate

To a solution (1500 mL) of 2-[(ethoxycarbonyl)(methyl)amino]ethyl ethyl carbonate (150 g) obtained in Reference Example 33 in acetonitrile was added phosphorus oxychloride (200 mL), and the mixture was refluxed for 4 days. The reaction mixture was concentrated under reduced pressure and the residue was added to a mixture of water (500 mL)-ice (700 g)-ethyl acetate (300 mL) by portions with stirring. After stirring for 1 min., saturated brine (500 mL) was added, and the mixture was extracted with ethyl acetate (500 mL). The ethyl acetate layer was washed successively with saturated brine (300 mL), a saturated aqueous sodium hydrogen carbonate solution (300 mL) and saturated brine (300 mL), dried over anhydrous sodium sulfate and concentrated under reduced pressure. The residue was evaporated under reduced pressure to give the title compound (77 g) as a colorless fraction having a boiling point of 100-105° C. (pressure: 0.1-0.2 mmHg).

$^1$H-NMR(CDCl$_3$): 1.33(3H,t,J=7.2 Hz), 3.12(3H×0.4,s), 3.22(3H×0.6,s), 3.68(2H×0.6,t,J=4.8 Hz), 3.78(2H×0.4,t, J=4.8 Hz), 4.23(2H,q,J=7.2 Hz), 4.30-4.40(2H,m).

Reference Example 35

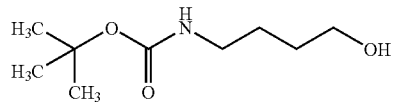

tert-Butyl 4-hydroxybutylcarbamate

To a mixture of 4-aminobutanol (3.57 g) and ethyl acetate (9 mL) was dropwise added a mixture of di-tert-butyl dicarbonate (8.73 g) and ethyl acetate (1 ml) under ice-cooling. After stirring at room temperature for 24 hrs., the mixture was concentrated under reduced pressure. The residue was dissolved in ethyl acetate (200 mL), and the mixture was washed with water (50 mL), 1N hydrochloric acid (40 mL), water (30 mL) and saturated brine (30 mL) and dried over anhydrous magnesium sulfate. Concentration under reduced pressure gave the title compound (7.54 g) as a colorless oil.

$^1$H-NMR (CDCl$_3$): 1.44(9H,s), 1.47-1.61(4H,m), 3.07-3.22(2H,m), 3.61-3.76(2H,m), 4.62(1H,bs).

Reference Example 36

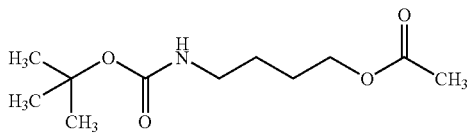

4-[(tert-Butoxycarbonyl)amino]butyl acetate

To a mixture of tert-butyl 4-hydroxybutylcarbamate (3.83 g) obtained in Reference Example 35 and ethyl acetate (20 mL) were added pyridine (1.80 mL) and acetic anhydride (2.27 g), and the mixture was stirred at room temperature for 0.19 hrs. Ethyl acetate (100 mL) was added to the reaction mixture, and the mixture was washed with water (50 mL), an aqueous copper sulfate solution (30 mL), water (30 mL) and saturated brine (30 mL) and dried over anhydrous magnesium sulfate. Concentration under reduced pressure gave the title compound (4.55 g) as a colorless oil.

$^1$H-NMR(CDCl$_3$): 1.44(9H,s), 1.51-1.69(4H,m), 2.05(3H, s), 3.15(2H,m), 4.07(2H,t,J=6.5 Hz), 4.55(1H,bs).

Reference Example 37

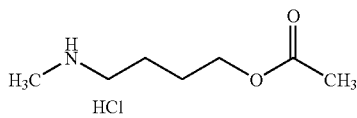

4-(Methylamino)butyl acetate hydrochloride

To a solution (20 mL) of 4-[(tert-butoxycarbonyl)amino) butyl acetate (4.50 g) obtained in Reference Example 36 and methyl iodide (4.85 mL) in N,N-dimethylformamide was added sodium hydride (60% in oil, 0.94 g) under ice-cooling. After stirring at room temperature for 4 hrs., the reaction mixture was poured into an ice-aqueous ammonium chloride solution. The mixture was extracted with diethyl ether (120 mL), and the diethyl ether layer was washed with saturated brine (30 mL) and dried over anhydrous magnesium sulfate. After concentration under reduced pressure, the residue was purified by silica gel column chromatography (eluted with ethyl acetate:hexane=1:9). To the purified product was added a 4N hydrogen chloride-ethyl acetate solution (20 mL), and the mixture was stirred at room temperature for 2 hrs. Diethyl ether (40 mL) was added, and the precipitated solid was collected by filtration. The solid was dried under reduced pressure to give the title compound (2.28 g) as a white solid.

$^1$H-NMR(DMSO-d$_6$) 1.58-1.70(4H,m), 2.01(3H,s), 2.50 (3H,s), 2.82-2.90(2H,m), 4.00(2H,t,J=6.0 Hz), 8.90(2H,br).

Reference Example 38

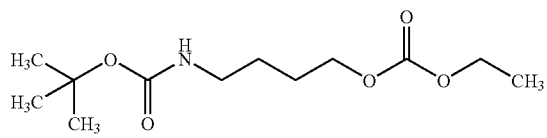

4-[(tert-Butoxycarbonyl)amino]butyl ethyl carbonate

To a mixture of tert-butyl 4-hydroxybutylcarbamate (3.71 g) obtained in Reference Example 35 and ethyl acetate (20 mL) were added pyridine (1.71 mL) and ethyl chlorocarbonate (2.55 g) under ice-cooling, and the mixture was stirred at room temperature for 24 hrs. Ethyl acetate (100 mL) was added to the reaction mixture, and the mixture was washed with water (50 mL), an aqueous copper sulfate solution (30 mL), water (30 mL) and saturated brine (30 mL) and dried over anhydrous magnesium sulfate. Concentration under reduced pressure gave the title compound (4.92 g) as a colorless oil.

$^1$H-NMR(CDCl$_3$): 1.31(3H,t,J=7.1 Hz), 1.44(9H,s), 1.46-1.80(4H,m), 3.15(2H,m), 4.11-4.25(4H,m), 4.54(1H,bs).

Reference Example 39

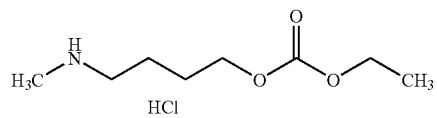

Ethyl 4-(methylamino)butyl carbonate hydrochloride

To a solution (20 mL) of 4-[(tert-butoxycarbonyl)amino] butyl ethyl carbonate (4.90 g) obtained in Reference Example 38 and methyl iodide (4.67 mL) in N,N-dimethylformamide was added sodium hydride (60% in oil, 0.90 g) under ice-cooling. After stirring at room temperature for 6 hrs., the reaction mixture was poured into an ice-aqueous ammonium chloride solution, and extracted with diethyl ether (120 mL). The diethyl ether layer was washed with saturated brine (30 mL) and dried over anhydrous magnesium sulfate. After concentration under reduced pressure, the residue was purified by silica gel column chromatography (eluted with ethyl acetate: hexane=1:9). To the purified product was added a 4N hydrogen chloride-ethyl acetate solution (20 mL), and the mixture was stirred at room temperature for 2 hrs. Diethyl ether (40 mL) was added, and the precipitated solid was collected by filtration. The solid was dried under reduced pressure to give the title compound (2.86 g) as a white solid.

$^1$H-NMR(DMSO-d$_6$): 1.21(3H,t,J=7.1 Hz), 1.51-1.73(4H, m), 2.50(3H,s), 2.82-2.94(2H,m), 4.05-4.15(4H,m), 8.88(2H,br).

Reference Example 40

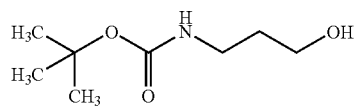

tert-Butyl 3-hydroxypropylcarbamate

To a mixture of 3-aminopropanol (7.51 g) and ethyl acetate (30 mL) was dropwise added a mixture of di-tert-butyl dicarbonate (21.8 g) and ethyl acetate (3 mL) under ice-cooling. After stirring at room temperature for 22 hrs., the mixture was concentrated under reduced pressure. The residue was dissolved in ethyl acetate (200 mL), washed with water (80 mL), 1N hydrochloric acid (60 mL), water (50 mL) and saturated brine (50 mL), and dried over anhydrous sodium sulfate. Concentration under reduced pressure gave the title compound (16.01 g) as a colorless oil.

$^1$H-NMR(CDCl$_3$): 1.45(9H,s), 1.62-1.70(2H,m), 3.24(2H, q,J=6.6 Hz), 3.66(2H,q,J=5.1 Hz), 4.73(1H,bs).

Reference Example 41

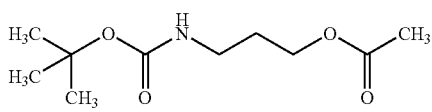

3-[(tert-Butoxycarbonyl)amino]propyl acetate

To a mixture of tert-butyl 3-hydroxypropylcarbamate (8.00 g) obtained in Reference Example 40 and ethyl acetate (50 mL) were added pyridine (4.06 mL) and acetic anhydride (5.13 g), and the mixture was stirred at room temperature for 21 hrs. Ethyl acetate (200 mL) was added to the reaction mixture, and the mixture was washed with water (100 mL), an aqueous copper sulfate solution (40 mL), water (60 mL) and saturated brine (60 mL), and dried over anhydrous sodium sulfate. Concentration under reduced pressure gave the title compound (8.34 g) as a colorless oil.
$^1$H-NMR(CDCl$_3$): 1.44(9H,s), 1.77-1.86(2H,m), 2.06(3H, s), 3.20(2H,q,J=6.3 Hz), 4.12(2H,t,J=6.3 Hz), 4.67(1H,bs).

Reference Example 42

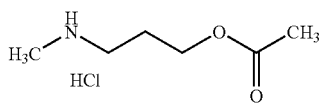

3-(Methylamino)propyl acetate hydrochloride

To a solution (80 mL) of 3-[(tert-butoxycarbonyl)amino]propyl acetate (17.28 g) obtained in Reference Example 41 and methyl iodide (19.8 mL) in N,N-dimethylformamide was added sodium hydride (60% in oil, 3.82 g) under ice-cooling. After stirring at room temperature for 15 hrs., the reaction mixture was poured into an ice-aqueous ammonium chloride solution and extracted with diethyl ether (300 mL). The diethyl ether layer was washed with saturated brine (100 mL), and dried over anhydrous sodium sulfate. After concentration under reduced pressure, the residue was purified by silica gel column chromatography (eluted with ethyl acetate:hexane=1:8). To the purified product was added a 4N hydrogen chloride-ethyl acetate solution (40 mL), and the mixture was stirred at room temperature for 2 hrs. Diethyl ether (100 mL) was added, and the precipitated solid was collected by filtration. The solid was dried under reduced pressure to give the title compound (2.93 g) as a white solid.
$^1$H-NMR(DMSO-d$_6$): 1.85-1.97(2H,m), 2.02(3H,s), 2.50 (3H,s), 2.87-2.96(2H,m), 4.06(2H,t,J=6.3 Hz), 8.87(2H,br).

Reference Example 43

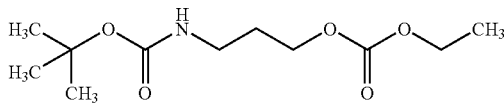

3-[(tert-Butoxycarbonyl)amino]propyl ethyl carbonate

To a mixture of tert-butyl 3-hydroxypropylcarbamate (8.00 g) obtained in Reference Example 40 and ethyl acetate (50 mL) were added pyridine (4.06 mL) and ethyl chlorocarbonate (5.95 g) under ice-cooling, and the mixture was stirred at room temperature for 24 hrs. Ethyl acetate (100 mL) was added to the reaction mixture, and the mixture was washed with water (50 mL), an aqueous copper sulfate solution (30 mL), water (30 mL) and saturated brine (30 mL), and dried over anhydrous sodium sulfate. Concentration under reduced pressure gave the title compound (9.31 g) as a colorless oil.
$^1$H-NMR(CDCl$_3$): 1.31(3H,t,J=7.1 Hz), 1.44(9H,s), 1.82-1.90(2H,m), 3.22(2H,t,J=6.3 Hz), 4.15-4.23(4H,m), 4.68(1H,bs).

Reference Example 44

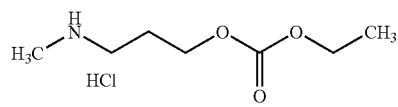

Ethyl 3-(methylamino)propyl carbonate hydrochloride

To a solution (40 mL) of 3-[(tert-butoxycarbonyl)amino]propyl ethyl carbonate (9.31 g) obtained in Reference Example 43 and methyl iodide (9.00 mL) in N,N-dimethylformamide was added sodium hydride (60% in oil, 1.82 g) under ice-cooling. After stirring at room temperature for 12 hrs., the reaction mixture was poured into an ice-aqueous ammonium chloride solution and the mixture was extracted with diethyl ether (200 mL). The diethyl ether layer was washed with saturated brine (100 mL), and dried over anhydrous sodium sulfate. After concentration under reduced pressure, the residue was purified by silica gel column chromatography (eluted with ethyl acetate:hexane=1:8). To the purified product was added a 4N hydrogen chloride-ethyl acetate solution (40 mL), and the mixture was stirred at room temperature for 2 hrs. Diethyl ether (200 mL) was added, and the precipitated solid was collected by filtration. The solid was dried under reduced pressure to give the title compound (4.98 g) as a white solid.
$^1$H-NMR(DMSO-d$_6$): 1.21(3H,t,J=7.1 Hz), 1.91-2.00(2H, m), 2.50(3H,s), 2.88-2.98(2H,m), 4.08-4.16(4H,m) 8.90(2H, br).

Reference Example 45

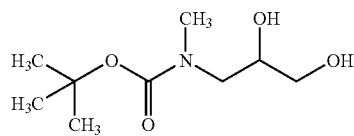

tert-Butyl(2,3-dihydroxypropyl)methylcarbamate

To a mixture of 3-(methylamino)-1,2-propanediol (24.5 g) and ethyl acetate (50 mL) was dropwise added a mixture of di-tert-butyl dicarbonate (51.4 g) and ethyl acetate (10 mL) under ice-cooling. After stirring at room temperature for 15 hrs., the mixture was concentrated under reduced pressure. The residue was dissolved in ethyl acetate (150 mL), and the solution was washed with water (80 mL), 1N hydrochloric acid (60 mL), water (50 mL) and saturated brine (50 mL), and dried over anhydrous sodium sulfate. Concentration under reduced pressure gave the title compound (26.9 g) as a colorless oil.

$^1$H-NMR(CDCl$_3$): 1.47(9H,s), 2.92(3H,s), 3.20-3.36(2H, m), 3.41(2H,bs), 3.50-3.62(2H,m), 3.73-3.88(1H,m).

Reference Example 46

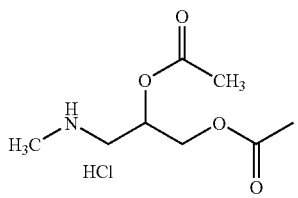

3-(Methylamino)propane-1,2-diyl diacetate hydrochloride

To a mixture of tert-butyl(2,3-dihydroxypropyl)methylcarbamate (10.26 g) obtained in Reference Example 45 and ethyl acetate (50 mL) were added pyridine (10.11 mL) and acetic anhydride (12.76 g), and the mixture was stirred at room temperature for 24 hrs. Ethyl acetate (300 mL) was added to the reaction mixture, and the mixture was washed with water (150 mL), an aqueous copper sulfate solution (100 mL), water (100 mL) and saturated brine (100 mL), and dried over anhydrous sodium sulfate. After concentration under reduced pressure, the residue was purified by silica gel column chromatography (eluted with ethyl acetate:hexane=1:8). To the purified product was added a 4N hydrogen chloride-ethyl acetate solution (40 mL), and the mixture was stirred at room temperature for 3 hrs. Diethyl ether (100 mL) was added, and the precipitated solid was collected by filtration. The solid was dried under reduced pressure to give the title compound (2.76 g) as a white solid.

$^1$H-NMR(DMSO-d$_6$): 2.03(3H,s), 2.07(3H,s), 2.55(3H,s), 3.18-3.22(2H,m), 4.09-4.28(2H,m), 5.20-5.27(1H,m), 9.01 (2H,br).

Reference Example 47

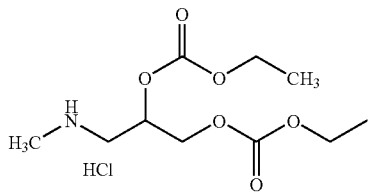

Diethyl 3-(methylamino)propane-1,2-diyl biscarbonate hydrochloride

To a mixture of tert-butyl(2,3-dihydroxypropyl)methylcarbamate (15.53 g) obtained in Reference Example 45 and ethyl acetate (100 mL) were added pyridine (18.35 mL) and ethyl chlorocarbonate (24.62 g) under ice-cooling, and the mixture was stirred at room temperature for 96 hrs. Ethyl acetate (300 mL) was added to the reaction 1 mixture, and the mixture was washed with water (150 mL), an aqueous copper sulfate solution (100 mL), water (100 mL) and saturated brine (100 mL), and dried over anhydrous sodium sulfate. After concentration under reduced pressure, the residue was purified by silica gel column chromatography (eluted with ethyl acetate:hexane=1:6). To the purified product was added a 4N hydrogen chloride-ethyl acetate solution (80 mL), and the mixture was stirred at room temperature for 3 hrs. Diethyl ether (200 mL) was added, and the precipitated solid was collected by filtration. The solid was dried under reduced pressure to give the title compound (5.93 g) as a white solid.

$^1$H-NMR(DMSO-d$_6$): 1.20-1.28(6H,m), 2.57(3H,s), 3.12-3.28(2H,m) 4.10-4.43(6H,m), 5.13-5.22(1H,m), 9.14(2H,br).

Reference Example 48

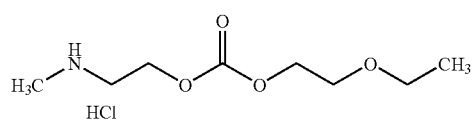

2-Ethoxyethyl 2-(methylamino)ethyl carbonate hydrochloride

To a solution (20 mL) of bis(trichloromethyl)carbonate (2.97 g) in tetrahydrofuran was dropwise added a solution (10 mL) of 2-ethoxyethanol (1.80 g) in tetrahydrofuran under ice-cooling. Then a solution (10 mL) of pyridine (2.43 mL) in tetrahydrofuran was added dropwise, and the mixture was stirred at room temperature for 2 hrs. The reaction mixture was concentrated under reduced pressure and water (50 mL) was added to the residue. The mixture was extracted with ethyl acetate (50 mL). The ethyl acetate layer was washed with 0.2N hydrochloric acid (20 mL) and saturated brine (50 mL), dried over anhydrous magnesium sulfate, and concentrated under reduced pressure to give 2-ethoxyethyl chlorocarbonate (1.29 g). A solution (15 mL) of tert-butyl 2-hydroxyethyl(methyl)carbamate (1.23 g) obtained in Reference Example 1 in tetrahydrofuran was added pyridine (0.68 mL), and a solution (5 mL) of 2-ethoxyethyl chlorocarbonate obtained above in tetrahydrofuran was dropwise added to the mixture, and the mixture was stirred at room temperature for 3 days. After concentration of the reaction mixture under reduced pressure, water (50 mL) was added thereto and the mixture was extracted with ethyl acetate (50 mL). The ethyl acetate layer was washed with a 5% aqueous citric acid solution (50 mL) and saturated brine (50 mL), dried over anhydrous magnesium sulfate. The mixture was concentrated under reduced pressure and the residue was purified by silica gel column chromatography (eluted with ethyl acetate:hexane=1:5, then 2:3). The purified product (1.60 g) was dissolved in diethyl ether (3 mL) and a 4N hydrogen chloride-ethyl acetate solution (3 mL) was added. The mixture was stirred overnight at room temperature, and the precipitated solid was collected by filtration and dried under reduced pressure to give the title compound (0.94 g) as a white solid.

$^1$H-NMR(DMSO-d$_6$): 1.10(3H,t,J=7.0 Hz), 2.57(3H,s), 3.18-3.25(2H,m), 3.44(2H,q,J=7.0 Hz), 3.56-3.60(2H,m), 4.19-4.24(2H,m), 4.30-4.37(2H,m), 8.79(2H,br).

Reference Example 49

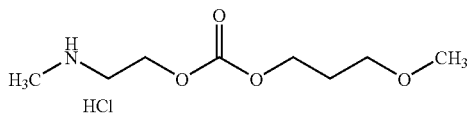

3-Methoxypropyl 2-(methylamino)ethyl carbonate hydrochloride

To a mixture of lithium aluminum hydride (2.85 g) and diethyl ether (100 mL) was dropwise added slowly a solution (50 mL) of methyl 3-methoxypropanoate (11.8 g) in tetrahydrofuran under ice-cooling. After stirring at room temperature for 1 hr., the mixture was again ice-cooled and water (3 mL) and a 10% aqueous sodium hydroxide solution (3 mL) were dropwise added. The mixture was allowed to reach room temperature, and water (9 mL) was dropwise added. The mixture was stirred for a while. The precipitate was filtered off and the filtrate was concentrated under reduced pressure to give 3-methoxypropanol (7.64 g) as a colorless oil.

$^1$H-NMR(CDCl$_3$): 1.83(2H,quintet,J=5.8 Hz), 2.43(1H,t,J=5.3 Hz) 3.36(3H,s), 3.57(2H,t,J=6.0 Hz), 3.77(2H,q,J=5.5 Hz).

To a solution (50 mL) of bis(trichloromethyl)carbonate (4.45 g) in tetrahydrofuran was dropwise added N-ethyldiisopropylamine (5.75 mL) under ice-cooling. After stirring for a while, a solution (15 mL) of 3-methoxypropanol (2.70 g) obtained above in tetrahydrofuran was dropwise added. The mixture was stirred for 30 min. under ice-cooling and at room temperature for 1 day. After concentration of the reaction mixture under reduced pressure, diluted hydrochloric acid (50 mL) was added to the residue, and the mixture was extracted with ethyl acetate (80 mL). The ethyl acetate layer was washed with 0.2N hydrochloric acid (30 mL) and saturated brine (30 mL), dried over anhydrous magnesium sulfate and concentrated under reduced pressure to give 3-methoxypropyl chlorocarbonate (4.39 g). To a solution (20 mL) of tert-butyl 2-hydroxyethyl(methyl)carbamate (1.75 g) obtained in Reference Example 1 in tetrahydrofuran was added pyridine (0.97 mL) and a solution (5 mL) of a 3-methoxypropyl chlorocarbonate (1.83 g) obtained above in tetrahydrofuran was dropwise added, and the mixture was stirred at room temperature for 2 hrs. A solution (5 mL) of pyridine (0.65 mL) and 3-methoxypropyl chlorocarbonate (1.22 g) in tetrahydrofuran was added and the mixture was further stirred for 1 hr. The reaction mixture was concentrated under reduced pressure and water (50 mL) was added to the residue. The mixture was extracted with ethyl acetate (80 mL), and the ethyl acetate layer was washed with a 5% aqueous citric acid solution (50 mL) and saturated brine (50 mL), dried over anhydrous magnesium sulfate and concentrated under reduced pressure. The residue was purified by silica gel column chromatography (eluted with ethyl acetate:hexane=1:9, then 3:7). The purified product (3.40 g) was dissolved in diethyl ether (5 mL) and a 4N hydrogen chloride-ethyl acetate solution (5 mL) was added. The mixture was stirred overnight at room temperature and the reaction mixture was concentrated under reduced pressure. Diethyl ether was added for crystallization to give the title compound (2.06 g) as a colorless solid.

$^1$H-NMR(DMSO-d$_6$): 1.78-1.90(2H,m), 2.54(3H,s), 3.15-3.25(2H,m), 3.23(3H,s), 3.33-3.42(2H,m), 4.16(2H,t,J=6.0 Hz), 0.36(2H,t,J=6.0 Hz), 9.27(2H,br).

Reference Example 50

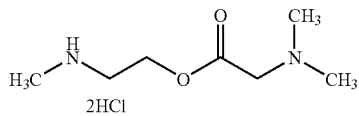

2-(Methylamino)ethyl N,N-dimethylglycinate dihydrochloride

A mixture of tert-butyl 2-hydroxyethyl(methyl)carbamate (3.50 g) obtained in Reference Example 1, N,N-dimethylglycine hydrochloride (5.29 g), 1-ethyl-3-[3-(dimethylamino)propyl]carbodiimide hydrochloride (7.67 g) triethylamine (5.58 mL), 4-dimethylaminopyridine (1.22 g) and N,N-dimethylformamide (50 mL) was stirred overnight at room temperature. The reaction mixture was concentrated under reduced pressure and a saturated aqueous sodium hydrogen carbonate solution (50 mL) was added to the residue. The mixture was extracted with ethyl acetate (100 mL). The ethyl acetate layer was washed with saturated brine (50 mL), dried over anhydrous magnesium sulfate and concentrated under reduced pressure. The residue was purified by silica gel column chromatography (eluted with methanol:ethyl acetate=5:95, then 20:80). 1N Hydrochloric acid (24 mL) was added to the purified product (2.46 g), and the mixture was stirred overnight at room temperature. The reaction mixture was concentrated under reduced pressure to give the title compound (2.14 g) as a colorless solid.

$^1$H-NMR(DMSO-d$_6$): 2.52(3H,s), 2.85(6H,s), 3.20(2H,m), 4.30(2H,s), 4.43-4.49(2H,m), 9.60(2H,br), 10.81(1H,br).

Reference Example 51

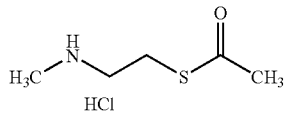

S-[2-(Methylamino)ethyl]thioacetate hydrochloride

To a solution (50 mL) of tert-butyl 2-hydroxyethyl(methyl)carbamate (3.50 g) obtained in Reference Example 1, thioacetic acid (1.72 mL) and triphenylphosphine (7.87 g) in tetrahydrofuran was dropwise added slowly a solution (10 mL) of diisopropyl azodicarboxylate (5.91 mL) in tetrahydrofuran under ice-cooling. The mixture was stirred under ice-cooling for 1 hr. and at room temperature for 2 hrs. The reaction mixture was again ice-cooled and a solution (10 mL) of triphenylphosphine (7.87 g) and diisopropyl azodicarboxylate (5.91 mL) in tetrahydrofuran was added. The mixture was stirred under ice-cooling for 30 min. Thioacetic acid (1.14 mL) was added and the mixture was stirred under ice-cooling for 30 min. and at room temperature overnight. The reaction mixture was concentrated under reduced pressure and hexane and diisopropyl ether were added to the residue. The precipitate was filtered off and the filtrate was concentrated under reduced pressure. This step was repeated and a saturated aqueous sodium hydrogen carbonate solution (50 mL) was added. The mixture was extracted with ethyl acetate (100 mL). The ethyl acetate layer was washed with saturated brine (50 mL), dried over anhydrous magnesium sulfate and concentrated under reduced pressure. The residue was purified by silica gel column chromatography (eluted with ethyl acetate:hexane=5:95, and then 15:85). A 4N hydrogen chloride-ethyl acetate solution (10 mL) was added to the purified product (4.47 g) and the mixture was stirred overnight at room temperature. The reaction mixture was concentrated under reduced pressure and ethyl acetate and diethyl ether were added to the residue for crystallization to give the title compound (1.79 g) as a pale-yellow solid.

$^1$H-NMR(DMSO-$d_6$): 2.38(3H,s), 2.52(3H,s), 2.96-3.08 (2H,m), 3.12-3.20(2H,m), 9.35(2H,br).

Reference Example 52

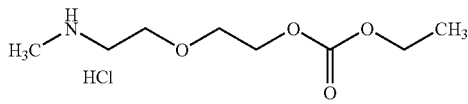

Ethyl 2-[2-(methylamino)ethoxy]ethyl carbonate hydrochloride

To a mixture of 2-(2-aminoethoxy)ethanol (99.52 g) and ethyl acetate (200 mL) was dropwise added a mixture of di-tert-butyl dicarbonate (208.57 g) and ethyl acetate (50 mL) under ice-cooling. After stirring at room temperature for 60 hrs., the mixture was concentrated under reduced pressure. The residue was dissolved in ethyl acetate (500 mL), washed with water (200 mL), 1N hydrochloric acid (200 mL), water (300 mL) and saturated brine (300 mL), and dried over anhydrous sodium sulfate. Concentration under reduced pressure gave tert-butyl [2-(2-hydroxyethoxy)ethyl]carbamate (169.2 g) as a colorless oil.

$^1$H-NMR(CDCl$_3$): 1.45(9H,s), 3.33(2H,q,J=5.1 Hz), 3.54-3.59(4H,m), 3.74(2H,q,J=5.1 Hz), 4.88(2H,bs).

To a mixture of tert-butyl[2-(2--hydroxyethoxy)ethyl]carbamate (53.93 g) obtained above and ethyl acetate (350 mL) were added pyridine (53.78 mL) and ethyl chlorocarbonate (70.57 g) under ice-cooling, and the mixture was stirred at room temperature for 96 hrs. Ethyl acetate (500 mL) was added to the reaction mixture, and the mixture was washed with water (500 mL), an aqueous copper sulfate solution (200 mL), water (300 mL) and saturated brine (300 mL) and dried over anhydrous sodium sulfate. Concentration under reduced pressure gave 2-[2-[(tert-butoxycarbonyl)amino]ethoxy] ethyl ethyl carbonate (93.19 g) as a colorless oil.

$^1$H-NMR(CDCl$_3$): 1.32(3H,t,J=7.2 Hz), 1.44(9H,s), 3.32 (2H,t, J=5.1 Hz), 3.54(2H,t, J=5.1 Hz), 3.67-3.74(2H,m), 4.21(2H,q, J=7.2 Hz), 4.26-4.31(2H,m), 4.91(1H,bs).

To a solution (350 mL) of 2-[2-[(tert-butoxycarbonyl) amino]ethoxy]ethyl ethyl carbonate (93.15 g) obtained above and methyl iodide (83.6 mL) in N,N-dimethylformamide was added sodium hydride (60% in oil, 16.12 g) under ice-cooling. After stirring at room temperature for 24 hrs., the reaction mixture was poured into an ice-aqueous ammonium chloride solution, and extracted with diethyl ether (800 mL). The diethyl ether layer was washed with saturated brine (300 mL), and dried over anhydrous magnesium sulfate. After concentration under reduced pressure, the residue was purified by silica gel column chromatography (eluted with ethyl acetate: hexane=1:8). To the purified product was added a 4N hydrogen chloride-ethyl acetate solution (300 mL) was added, and the mixture was stirred at room temperature for 2 hrs. Diethyl ether (300 mL) was added, and the precipitated solid was collected by filtration. The solid was dried under reduced pressure to give the title compound (33.21 g) as a white solid.

$^1$H-NMR(DMSO-$d_6$): 1.21(3H,t,J=7.2 Hz), 2.51(3H,s), 3.02-3.09(2H,m), 3.65-3.72(4H,m), 4.12(2H,q,J=7.2 Hz), 4.22(2H,t,J=4.5 Hz), 9.06(2H,br).

Reference Example 53

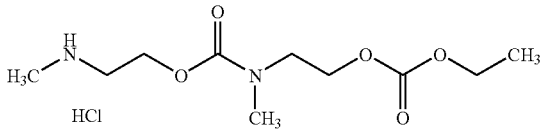

Ethyl 2-[methyl[[2-(methylamino)ethoxy]carbonyl] amino]ethyl carbonate hydrochloride To a solution (100 mL) of bis(trichloromethyl)carbonate (11.87 g) in tetrahydrofuran was dropwise added a solution (20 mL) of pyridine (9.71 mL) in tetrahydrofuran under ice-cooling. After stirring under ice-cooling for 30 min., a solution (20 mL) of tert-butyl 2-hydroxyethyl(methyl)carbamate (17.52 g) obtained in Reference Example 1 in tetrahydrofuran was dropwise added and the mixture was stirred at room temperature for 15 hrs. After concentration under reduced pressure, water (500 mL) and anhydrous sodium sulfate were added to the residue. After filtration, the filtrate was concentrated under reduced pressure. To the obtained residue were added a solution (50 mL) of 2-(methylamino)ethanol (5.00 g) in ethyl acetate and triethylamine (10.0 mL) under ice-cooling and the mixture was stirred at room temperature for 15 hrs. Ethyl acetate (300 mL) was added to the reaction mixture, washed with water (150 mL) and saturated brine (200 mL) and dried over anhydrous sodium sulfate. After concentration under reduced pressure, to a mixture of the residue and ethyl acetate (100 mL) were added pyridine (2.91 mL) and ethyl chlorocarbonate (3.44 g) under ice-cooling, and the mixture was stirred at room temperature for 48 hrs. Ethyl acetate (200 mL) was added to the reaction mixture, washed with water (100 ml), an aqueous copper sulfate solution (50 mL), water (50 mL) and saturated brine (50 mL), and dried over anhydrous sodium sulfate. The mixture was concentrated under reduced pressure and the residue was purified by silica gel column chromatography (eluted with ethyl acetate:hexane=1:3). To the purified product was added a 4N hydrogen chloride-ethyl acetate solution (30 mL), and the mixture was stirred at room temperature for 3 hrs. Diethyl ether (100 ml) was added, and the precipitated solid was collected by filtration. The solid was dried under reduced pressure to give the title compound (2.90 g) as a white solid.

$^1$H-NMR(DMSO-$d_6$): 1.21(3H,t,J=7.2 Hz), 2.57(3H,bs), 2.86(1.5H,s), 2.93(1.5H,s), 3.16(2H,bs), 3.34(1H,bs), 3.48 (1H,t,J=5.1 Hz), 3.58(1H,t,J=5.1 Hz), 4.12(2H,q,J=7.2 Hz), 4.16-4.24(4H,m), 8.94(1H,br).

Reference Example 54

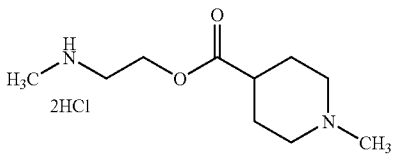

2-(Methylamino)ethyl
1-methylpiperidine-4-carboxylate dihydrochloride

A mixture of ethyl piperidine-4-carboxylate (4.72 g), methyl iodide (2.24 mL), potassium carbonate (8.29 g) and acetonitrile (50 mL) was stirred at room temperature for 2 hrs. The reaction mixture was concentrated under reduced pressure and water (150 mL) was added. The mixture was extracted with ethyl acetate (150 mL). The ethyl acetate layer was washed with saturated brine (100 mL), dried over anhydrous magnesium sulfate, and concentrated under reduced pressure. A 1N aqueous sodium hydroxide solution (20 mL) was added to the residue (2.64 g), and the mixture was stirred overnight at room temperature. The reaction mixture was neutralized by adding 1N hydrochloric acid (20 mL) and the mixture was concentrated under reduced pressure. Ethanol was added to the residue, and the precipitate was filtered off. The filtrate was concentrated under reduced pressure. This step was repeated and ethanol and ethyl acetate were added to the residue for crystallization to give 1-methylpiperidine-4-carboxylic acid (1.79 g) as a colorless solid.

$^1$H-NMR(CD$_3$OD): 1.80-1.98(2H,m), 2.00-2.14(2H,m), 2.28-2.42(1H,m), 2.78(3H,s), 2.88-3.04(2H,m), 3.32-3.44 (2H,m).

A mixture of 1-methylpiperidine-4-carboxylic acid (1.72 g) obtained above, tert-butyl 2-hydroxyethyl(methyl)carbamate (1.75 g) obtained in Reference Example 1, 1-ethyl-3-[3-(dimethylamino)propyl]carbodiimide hydrochloride (2.30 g), 4-dimethylaminopyridine (0.24 g) and acetonitrile (50 mL) was stirred at room temperature for 16 hrs. The reaction mixture was concentrated under reduced pressure and a saturated aqueous sodium hydrogen carbonate solution (50 mL) was added to the residue. The mixture was extracted with ethyl acetate (100 mL). The ethyl acetate layer was washed with saturated brine (50 mL), dried over anhydrous magnesium sulfate and concentrated under reduced pressure. The residue was purified by basic silica gel column chromatography (eluted with ethyl acetate:hexane=50:50, then 80:20). 1N Hydrochloric acid (25 mL) was added to the purified product (2.73 g), and the mixture was stirred overnight at room temperature. The reaction mixture was concentrated under reduced pressure and isopropanol was added. The mixture was again concentrated under reduced pressure and the precipitated solid was collected by filtration to give the title compound (1.72 g) as a colorless solid.

$^1$H-NMR(DMSO-d$_6$): 1.70-2.20(4H,m), 2.40-3.50(13H, m), 4.31(2H,m), 9.25(2H,br), 10.77(1H,br).

Reference Example 55

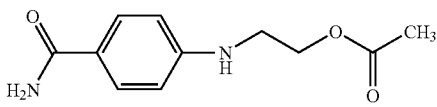

2-[[4-(Aminocarbonyl)phenyl]amino]ethyl acetate

A mixture of 4-fluorobenzonitrile (6.06 g), 2-aminoethanol (3.71 g), potassium carbonate (8.29 g) and dimethyl sulfoxide (50 mL) was stirred at 100° C. overnight. Water (200 mL) was added to the reaction mixture and the mixture was extracted with ethyl acetate (200 mL×4). The ethyl acetate layer was washed with saturated brine (100 mL), dried over anhydrous magnesium sulfate and concentrated under reduced pressure. The residue was purified by silica gel column chromatography (eluted with ethyl acetate:hexane=30:70, then 50:50, then 80:20, then ethyl acetate) to give 4-[(2-hydroxyethyl)amino]benzonitrile (5.89 g) as a yellow solid.

$^1$H-NMR(CDCl$_3$): 2.04(1H,t,J=4.8 Hz), 3.33(2H,m) 3.86 (2H,q,J=4.8 Hz), 4.66(1H,br), 6.58(2H,d,J=8.7 Hz), 7.39 (2H,d,J=8.7 Hz).

A mixture of 4-[(2-hydroxyethyl)amino]benzonitrile (0.81 g) obtained above, potassium hydroxide (1.12 g) and tert-butanol (20 mL) was stirred at 100° C. for 1 hr. Water (100 mL) was added to the reaction mixture, and extracted with ethyl acetate (100 mL). The ethyl acetate layer was washed with saturated brine (80 mL), dried over anhydrous magnesium sulfate and concentrated under reduced pressure. To a solution (10 mL) of the residue (0.83 g), pyridine (0.49 mL) and 4-dimethylaminopyridine (0.061 g) in tetrahydrofuran was dropwise added a solution (1 mL) of acetic anhydride (0.57 mL) 1 in tetrahydrofuran. The mixture was stirred at room temperature for 1 hr., water (80 mL) was added, and the mixture was extracted with ethyl acetate (100 mL). The ethyl acetate layer was washed with saturated brine (80 mL), dried over anhydrous magnesium sulfate and concentrated under reduced pressure. The residue was purified by silica gel column chromatography (eluted with ethyl acetate:hexane=30:70, then 60:40) to give the title compound (0.68 g) as a colorless solid.

$^1$H-NMR(CDCl$_3$): 2.08(3H,s), 3.44(2H,q,J=5.6 Hz) 4.29 (2H,t,J=5.4 Hz), 4.48(1H,br), 6.59(2H,d,J=8.9 Hz), 7.43(2H, d,J=8.9 Hz).

Reference Example 56

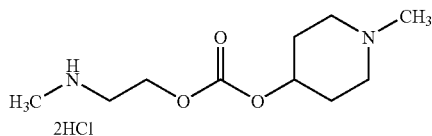

2-(Methylamino)ethyl 1-methyl-4-piperidinyl
carbonate dihydrochloride

To a solution (40 mL) of N,N'-carbonyldiimidazole (3.36 g) in tetrahydrofuran was dropwise added slowly a solution (10 mL) of tert-butyl 2-hydroxyethyl(methyl)carbamate (3.30 g) obtained in Reference Example 1 in tetrahydrofuran under ice-cooling. The mixture was stirred under ice-cooling for 40 min. and at room temperature for 2 hrs. N,N'-Carbonyldiimidazole (0.31 g) was added and the mixture was further stirred for 3 days. The reaction mixture was concentrated under reduced pressure and ethyl acetate (150 mL) was added to the residue. The mixture was washed with saturated brine (100 mL×2), water (50 mL×3) and saturated brine (50 mL), dried over anhydrous magnesium sulfate and concentrated under reduced pressure to give 2-[(tert-butoxycarbonyl)(methyl)amino]ethyl 1H-imidazole-1-carboxylate (5.24 g) as a colorless oil.

$^1$H-NMR(CDCl$_3$): 1.39(9H×0.5,s), 1.42(9H×0.5,s), 2.94 (3H,m), 3.63(2H,m), 4.51(2H,t,J=5.3 Hz), 7.06(1H,m), 7.42 (1H,m), 8.13(1H,s).

A mixture of 2-[(tert-butoxycarbonyl)(methyl)amino]ethyl 1H-imidazole-1-carboxylate (1.35 g) obtained above, 1-methyl-4-piperidinol (1.38 g) and acetonitrile (20 mL) was stirred overnight at room temperature. 1-Methyl-4-piperidinol (0.92 g) was added and the mixture was stirred overnight. The reaction mixture was concentrated under reduced pressure and a saturated aqueous sodium hydrogen carbonate solution (50 mL) was added to the residue. The mixture was extracted with ethyl acetate (100 mL). The ethyl acetate layer was washed with saturated brine (50 mL), dried over anhydrous magnesium sulfate and concentrated under reduced pressure. 1N Hydrochloric acid (12 mL) was added to the residue (1.60 g), and the mixture was stirred overnight at room temperature. The reaction mixture was concentrated under reduced pressure, water, isopropanol and ethyl acetate were added, and the precipitated solid was collected by filtration to give the title compound (1.09 g) as a colorless solid.

$^1$H-NMR(DMSO-$d_6$): 1.85-2.20(4H,m), 2.55(3H,s), 2.70 (3H×0.5,s), 2.73(3H×0.5,s), 2.90-3.50(6H,m), 4.38(2H,m), 4.65-5.00(1H,m), 9.21(2H,br), 11.10(1H,br).

Example 1

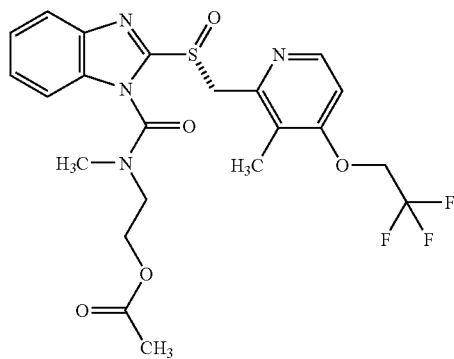

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 30 min., 2-(methylamino)ethyl acetate hydrochloride (0.77 g) obtained in Reference Example 2 was added. A solution (1 mL) of triethylamine (0.70 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The mixture was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (catalytic amount) were added, and the mixture was stirred at 60° C. overnight. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate), and further by silica gel column chromatography (eluted with ethyl acetate:hexane=2:1, then ethyl acetate, then acetone:ethyl acetate=1:4, then 1:1) to give the title compound (1.13 g) as a yellow amorphous solid.

$^1$H-NMR(CDCl$_3$): 2.10(3H,s), 2.24(3H,s), 3.09(3H,bs), 3.60-4.00(2H,br), 4.25-4.50(4H,m), 4.89(1H,d,J=13.3 Hz), 5.05(1H,d,J=13.3 Hz), 6.65(1H,d,J=5.5 Hz), 7.35-7.51(3H, m), 7.80-7.90(1H,m), 8.35(1H,d,J=5.5 Hz).

Example 2

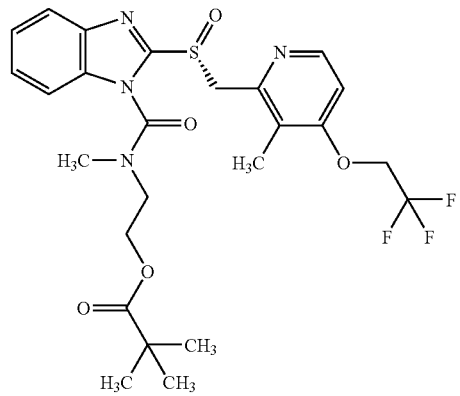

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl trimethylacetate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., 2-(methylamino)ethyl trimethylacetate hydrochloride (0.98 g) obtained in Reference Example 3 was added. A solution (1 mL) of triethylamine (0.70 mL) in tetrahydrofuran was dropwise added, and the mixture was stirred overnight at room temperature. After concentration under reduced pressure, water (50 mL) was added to the residue. The mixture was extracted with ethyl acetate (50 mL). The ethyl acetate layer was washed with saturated brine (50 mL), and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diisopropyl ether and recrystallization from acetone-diisopropyl ether gave the title compound (1.01 g) as a colorless solid.

$^1$H-NMR(CDCl$_3$): 1.23(9H,s), 2.23(3H,s), 3.08(3H,bs), 3.40-4.30(2H,br), 4.30-4.50(4H,m), 4.80-5.20(2H,br), 6.64 (1H,d,J=5.7 Hz), 7.35-7.50(3H,m), 7.78-7.88(1H,m), 8.35 (1H,d,J=5.7 Hz).

Example 3

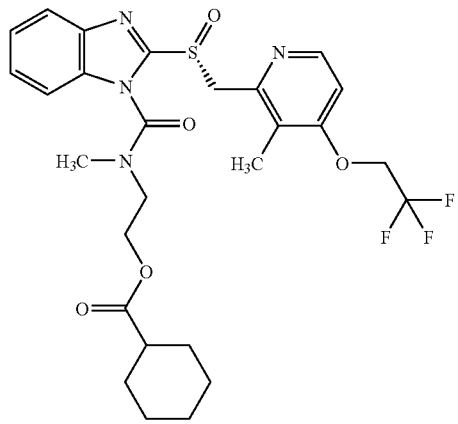

2-[Methyl[[(R)-2-[[[3-methyl-4-(2,2,2-trifluoroet-hoxy)-2-pyridyl]methyl]sulfinyl]-1H-benzimidazol-1-yl]carbonyl]amino]ethyl cyclohexanecarboxylate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 30 min., 2-(methylamino)ethyl cyclohexane. carboxylate hydrochloride (1.11 g) obtained in Reference Example 4 was added. A solution (1 mL) of triethylamine (0.70 mL) in tetrahydrofuran was dropwise added, and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diisopropyl ether and recrystallization from acetone-diisopropyl ether gave the title compound (1.11 g) as a colorless solid.

$^1$H-NMR(CDCl$_3$): 1.10-1.55(5H,m), 1.55-1.82(3H,m), 1.84-1.98(2H,m), 2.23(3H,s), 2.27-2.40(1H,m), 3.08(3H,bs), 3.40-4.30(2H,br), 4.30-4.50(4H,m), 4.80-5.15(2H,br), 6.64 (1H,d,J=5.4 Hz), 7.35-7.48(3H,m), 7.84(1H,d,J=6.9 Hz), 8.34(1H,d,J=5.4 Hz).

Example 4

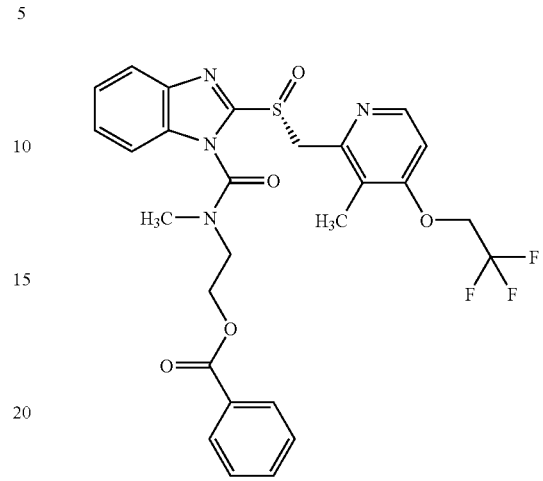

2-[Methyl[[(R)-2-[[[3-methyl-4-(2,2,2-trifluoroet-hoxy)-2-pyridyl]methyl]sulfinyl]-1H-benzimidazol-1-yl]carbonyl]amino]ethyl benzoate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., 2-(methylamino)ethyl benzoate hydrochloride (1.08 g) obtained in Reference Example 5 was added. A solution (1 mL) of triethylamine (0.70 mL) in tetrahydrofuran was dropwise added, and the mixture was stirred overnight at room temperature. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diethyl ether and recrystallization from acetone-diethyl ether gave the title compound (1.09 g) as a colorless solid.

$^1$H-NMR(CDCl$_3$): 2.22(3H,s), 3.12(3H,bs), 3.50-4.30 (2H,br), 4.37(2H,q,J=7.8 Hz), 4.68(2H,m), 4.80-5.20(2H, br), 6.63(1H,d,J=5.7 Hz), 7.26-7.48(5H,m), 7.53-7.61(1H, m), 7.82(1H,d,J=8.1 Hz), 8.04(2H,d,J=7.2 Hz), 8.33(1H,d, J=5.7 Hz).

Example 5

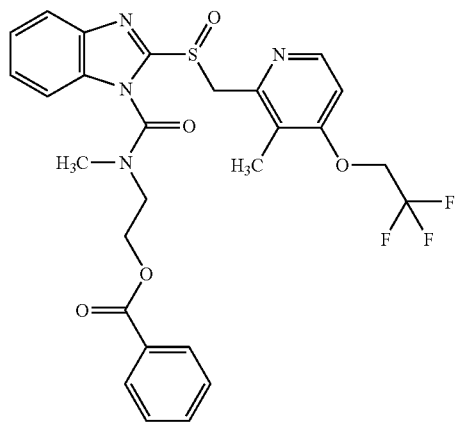

2-[Methyl[[2-[[[3-methyl-4-(2,2,2-trifluoroethoxy)-2-pyridyl]methyl]sulfinyl]-1H-benzimidazol-1-yl]carbonyl]amino]ethyl benzoate To a solution (30 mL) of bis(trichloromethyl)carbonate (0.99 g) in tetrahydrofuran was dropwise added a solution (2 mL) of pyridine (0.81 mL) in tetrahydrofuran under ice-cooling. After stirring under ice-cooling for 30 min., 2-(methylamino)ethyl benzoate hydrochloride (2.16 g) obtained in Reference Example 5 was added. After addition of a solution (2 mL) of triethylamine (1.39 mL) in tetrahydrofuran, the mixture was stirred at room temperature for 1 hr. After concentration under reduced pressure, ethyl acetate (100 mL) and water (100 mL) were added to the residue, and the mixture was stirred. The ethyl acetate layer was separated and taken, washed with saturated brine (50 mL) and dried over anhydrous magnesium sulfate. After concentration under reduced pressure, the residue was dissolved in tetrahydrofuran (40 mL). 2-[[[3-Methyl-4-(2,2,2-trifluoroethoxy)-2-pyridyl]methyl]sulfinyl]-1H-benzimidazole (2.90 g), triethylamine (2.20 mL) and 4-dimethylaminopyridine (0.096 g) were added, and the mixture was stirred at 60° C. for 2 hr. After concentration under reduced pressure, ethyl acetate (150 mL) and water (80 mL) were added to the residue, and the mixture was stirred. The ethyl acetate layer was separated and taken, washed with saturated brine (50 mL) and dried over anhydrous magnesium sulfate. After concentration under reduced pressure, the residue was purified by silica gel column chromatography (eluted with ethyl acetate:hexane=1:1, then ethyl acetate). Recrystallization from acetone gave the title compound (2.62 g) as a colorless solid.

$^1$H-NMR(CDCl$_3$): 2.22(3H,s), 3.13(3H,bs), 3.68-3.98 (2H,bm), 4.38(2H,q,J=7.8 Hz), 4.69(2H,m), 4.80-5.10(2H, bm), 6.64(1H,d,J=5.7 Hz), 7.27-7.48(5H,m), 7.59(1H,m), 7.83(1H,m), 8.06(2H,d,J=6.0 HZ), 8.35(1H,d,J=5.7 Hz).

Example 6

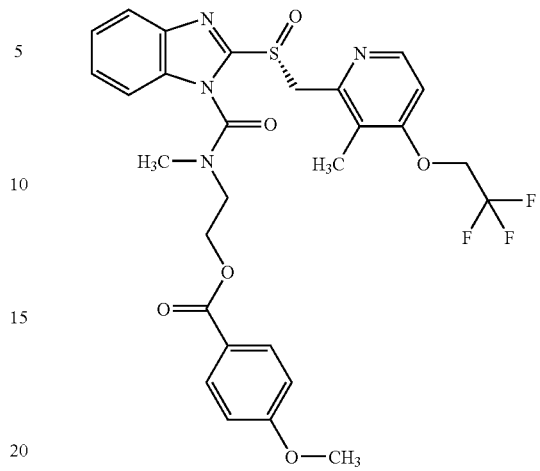

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-methoxybenzoate To a solution (18 mL) of bis(trichloromethyl)carbonate (0.584 g) in tetrahydrofuran was dropwise added a solution (1 mL) of pyridine (0.49 mL) in tetrahydrofuran under ice-cooling. After stirring under ice-cooling for 40 min., 2-(methylamino)ethyl 4-methoxybenzoate hydrochloride (1.48 g) obtained in Reference Example 6 was added. A solution (1 mL) of triethylamine (0.84 mL) in tetrahydrofuran was added and the mixture was stirred at room temperature for 80 min. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (25 mL). (R)-2-[[[3-Methyl-4-(2,2,2-trifluoroethoxy)-2-pyridyl]methyl]sulfinyl]-1H-benzimidazole (1.55 g), triethylamine (1.17 mL) and 4-dimethylaminopyridine (0.051 g) were added, and the mixture was stirred at 60° C. for 3 hrs. After concentration under reduced pressure, ethyl acetate (150 mL) and water (50 mL) were added to the residue, and the mixture was stirred. The ethyl acetate layer was separated and taken, washed with saturated brine (50 mL) and dried over anhydrous magnesium sulfate. After concentration under reduced pressure, the residue was purified by silica gel column chromatography (eluted with ethyl acetate:hexane=1:1, then ethyl acetate). Recrystallization from ethyl acetate-hexane gave the title compound (1.08 g) as a colorless solid.

$^1$H-NMR(CDCl$_3$): 2.22(3H,s), 3.11(3H,bs), 3.68-3.90 (2H,bm), 3.85(3H,s), 4.37(2H,q,J=7.9 Hz), 4.58-4.72(2H, m), 4.82-5.14(2H,bm), 6.63(1H,d,J=5.7 Hz), 6.91(2H,d, J=9.0 Hz), 7.27-7.40(3H,m), 7.82(1H,m), 7.99(2H,d,J=9.0 Hz), 8.33(1H,d,J=5.7 Hz).

Example 7

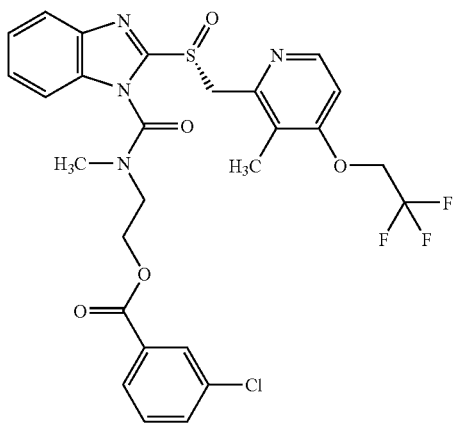

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3-chlorobenzoate To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 3-chlorobenzoate hydrochloride (1.50 g) obtained in Reference Example 7 was added. A solution (1 mL) of triethylamine (0.84 mL) in tetrahydrofuran was added and the mixture was stirred at room temperature for 2 hrs. After concentration under reduced pressure, ethyl acetate (80 mL) and water (40 mL) were added to the residue and the mixture was stirred. The ethyl acetate layer was separated and taken, washed with saturated-brine (25 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.44 g), triethylamine (1.09 mL) and 4-dimethylaminopyridine (0.048 g) were added, and the mixture was stirred at 60° C. for 3 hrs. After concentration under reduced pressure, ethyl acetate (80 mL) and water (40 mL) were added to the residue and the mixture was stirred. The ethyl acetate layer was separated and taken, washed with saturated brine (30 mL) and dried over anhydrous magnesium sulfate. After concentration under reduced pressure, the residue was purified by basic silica gel column chromatography (eluted with ethyl acetate: hexane=1:2, then 1:1) to give the title compound (0.84 g) as colorless syrup.

$^1$H-NMR(CDCl$_3$): 2.21(3H,s), 3.12(3H,bs), 3.78-4.08 (2H,bm), 4.38(2H,q,J=7.8 Hz), 4.64-5.08(4H,bm), 6.64(1H, d,J=5.2 Hz), 7.34-7.42(4H,m), 7.56(1H,m), 7.82(1H,m), 7.94(1H,d,J=7.6 Hz), 8.02(1H,s), 8.34(1H,d,J=5.2 Hz).

Example 8

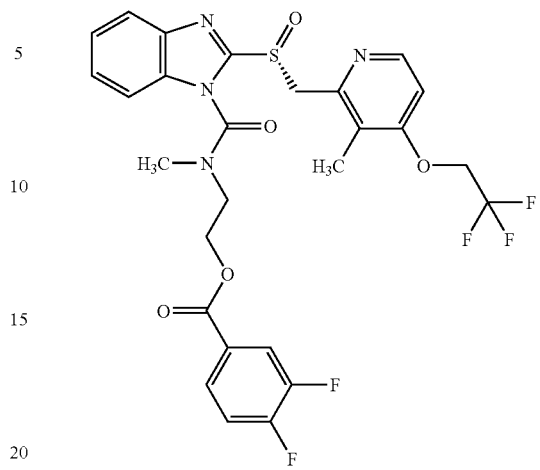

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4-difluorobenzoate To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 3,4-difluorobenzoate hydrochloride (1.51 g) obtained in Reference Example 8 was added. A solution (1 mL) of triethylamine (0.84 mL) in tetrahydrofuran was added and the mixture was stirred at room temperature for 3 hrs. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. The layer was concentrated under reduced pressure, and the residue was dissolved in tetrahydrofuran (25 mL). (R)-2-[[[3-Methyl-4-(2,2,2-trifluoroethoxy)-2-pyridyl]methyl]sulfinyl]-1H-benzimidazole (1.71 g), triethylamine (1.29 mL) and 4-dimethylaminopyridine (0.056 g) were added, and the mixture was stirred at 60° C. for 17 hrs. After concentration under reduced pressure, ethyl acetate (100 mL) and water (50 mL) were added to the residue, and the mixture was stirred. The ethyl acetate layer was separated and taken, and the aqueous layer was extracted with ethyl acetate (20 mL). Ethyl acetate layers were combined, washed with saturated brine (30 mL) and dried over anhydrous magnesium sulfate. After concentration under reduced pressure, the residue was purified by silica gel column chromatography (eluted with ethyl acetate:hexane=1:1, then 2:1), and by basic silica gel column chromatography (eluted with ethyl acetate:hexane=1:1). Crystallization from acetone-diisopropyl ether and recrystallization from ethyl acetate-hexane gave the title compound (1.37 g) as a colorless solid.

$^1$H-NMR(CDCl$_3$): 2.21(3H,s), 3.11(3H,bs), 3.82-4.08 (2H,bm), 4.38(2H,q,J=7.8 Hz), 4.60-5.14(4H,bm), 6.63(1H, d,J=5.7 Hz), 7.20(1H,m), 7.33-7.41(3H,m), 7.78-7.92(3H, m), 8.33(1H,d,J=5.7 Hz)

Example 9

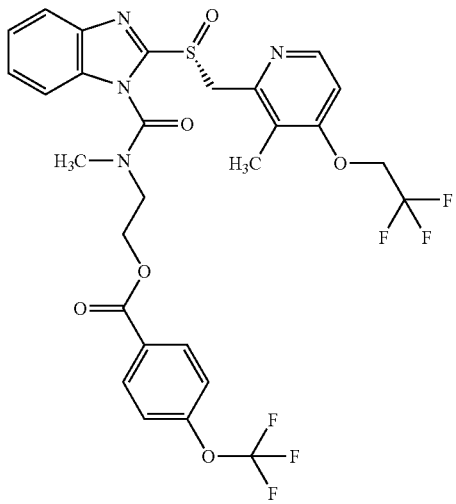

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-trifluoromethoxybenzoate To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 4-trifluoromethoxybenzoate hydrochloride (1.79 g) obtained in Reference Example 9 was added. A solution (1 mL) of triethylamine (0.84 mL) in tetrahydrofuran was added and the mixture was stirred at room temperature for 1.5 hrs. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (25 mL). (R)-2-[[[3-Methyl-4-(2,2,2-trifluoroethoxy)-2-pyridyl]methyl]sulfinyl]-1H-benzimidazole (1.57 g), triethylamine (1.18 mL) and 4-dimethylaminopyridine (0.052 g) were added, and the mixture was stirred at 60° C. for 4.5 hrs. After concentration under reduced pressure, ethyl acetate (100 mL) and water (50 mL) were added to the residue, and the mixture was stirred. The ethyl acetate layer was separated and taken, and the aqueous layer was extracted with ethyl acetate (30 mL). The ethyl acetate layers were combined, washed with saturated brine (30 mL) and dried over anhydrous magnesium sulfate. After concentration under reduced pressure, the residue was purified by silica gel column chromatography (eluted with ethyl acetate:hexane=1:1), and further by basic silica gel column chromatography (eluted with ethyl acetate:hexane=1:1) to give the title compound (1.44 g) as colorless syrup.

$^1$H-NMR(CDCl$_3$): 2.22(3H,s), 3.11(3H,bs), 3.85-4.05 (2H,bm), 4.38(2H,q,J=7.8 Hz), 4.60-5.12(4H,bm), 6.64(1H, d,J=5.7 Hz), 7.24(2H,d,J=8.7 Hz), 7.25-7.40(3H,m), 7.82 (1H,d,J=7.2 Hz), 8.09(2H,d,J=8.7 Hz), 8.33(1H,d,J=5.7 Hz).

Example 10

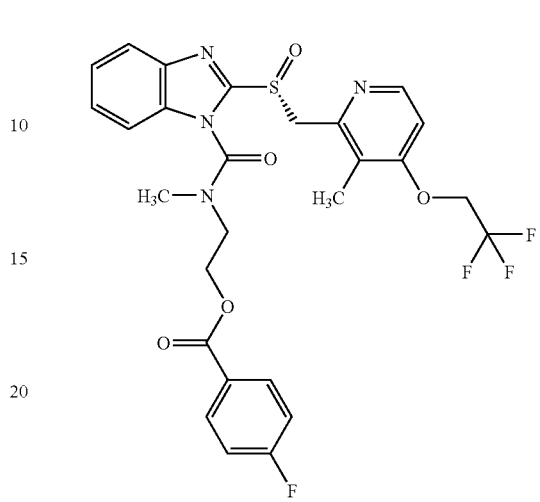

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-fluorobenzoate To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 4-fluorobenzoate hydrochloride (1.40 g) obtained in Reference Example 10 was added. A solution (1 mL) of triethylamine (0.84 mL) in tetrahydrofuran was added and the mixture was stirred at room temperature for 2 hrs. After concentration under reduced pressure, ethyl acetate (80 mL) and water (40 mL) were added to the residue and the mixture was stirred. The ethyl acetate layer was separated and taken, washed with saturated brine (30 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.32 g), triethylamine (1.00 mL) and 4-dimethylaminopyridine (0.049 g) were added, and the mixture was stirred at 60° C. for 14.5 hrs. After concentration under reduced pressure, ethyl acetate (150 mL) and water (50 mL) were added to the residue, and the mixture was stirred. The ethyl acetate layer was separated and taken, washed with saturated brine (30 mL) and dried over anhydrous magnesium sulfate. After concentration under reduced pressure, the residue was crystallized from ethyl acetate:hexane=1:1 and collected by filtration. Recrystallization from acetone gave the title compound (1.39 g) as a colorless solid.

$^1$H-NMR(CDCl$_3$): 2.22(3H,s), 3.12(3H,bs), 3.78-4.20 (2H,bm), 4.38(2H,q,J=7.8 Hz), 4.58-5.08(4H,bm), 6.65(1H, d,J=5.6 Hz), 7.11(2H,t,J=8.4 Hz), 7.28-7.44(3H,m), 7.81-7.86(1H,m), 8.03-8.11(2H,m), 8.35(1H,d,J=5.6 Hz).

Example 11

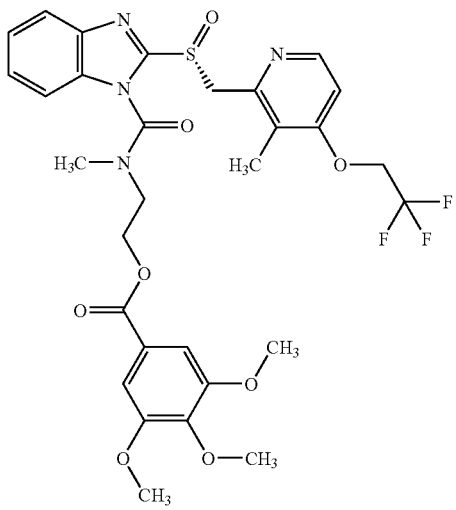

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4,5-trimethoxybenzoate To a solution (30 mL) of bis(trichloromethyl)carbonate (0.60 g) in tetrahydrofuran was dropwise added a solution (1 mL) of pyridine (0.49 mL) in tetrahydrofuran under ice-cooling. After stirring under ice-cooling for 10 min., 2-(methylamino)ethyl 3,4,5-teimethoxybenzoate hydrochloride (1.22 g) obtained in Reference Example 11 was added. A solution (1 mL) of triethylamine (0.84 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with dilute hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred at 60° C. for 3 hrs. and at room temperature for 2 days. After concentration under reduced pressure, water (50 ml) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2) to give the title compound (1.56 g) as a yellow amorphous solid.

$^1$H-NMR(CDCl$_3$), 2.21(3H,s), 3.12(3H,bs), 3.50-4.30(2H, br), 3.83(6H,s), 3.90(3H,s), 4.38(2H,q,J=7.8 Hz), 4.67(2H, m), 4.80-5.15(2H,br), 6.64(1H,d,J=5.7 Hz), 7.25-7.40(5H, m), 7.78-7.86(1H,m), 8.33(1H,d,J=5.7 Hz).

Example 12

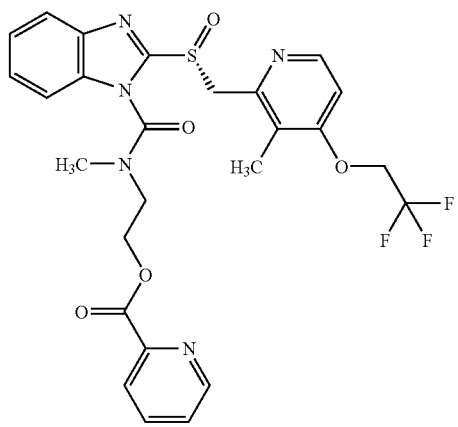

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 2-pyridinecarboxylate To a solution (30 mL) of bis(trichloromethyl)carbonate (0.422 g) in tetrahydrofuran was dropwise added pyridine (0.345 mL) under ice-cooling. After stirring under ice-cooling for 30 min., 2-(methylamino)ethyl 2-pyridinecarboxylate dihydrochloride (1.08 g) obtained in Reference Example 12 was added. After dropwise addition of triethylamine (1.19 mL), the mixture was stirred at room temperature for 2 hrs. The precipitated solid was filtered off and the filtrate was concentrated under reduced pressure. The residue was dissolved in tetrahydrofuran (10 mL), and (R)-2-[[[3-methyl-4-(2,2,2-trifluoroethoxy)-2-pyridyl]methyl]sulfinyl]-1H-benzimidazole (1.31 g), triethylamine (0.99 mL) and 4-dimethylaminopyridine (0.043 g) were added. The mixture was stirred at 60° C. for 24 hrs. Ethyl acetate (100 mL) was added to the reaction mixture, and the mixture was washed with water (100 mL) and saturated brine (100 mL), dried over anhydrous sodium sulfate, and concentrated under reduced pressure. The residue was purified by basic silica gel column chromatography (eluted with ethyl acetate:hexane=4:1). Crystallization from acetone-diethyl ether gave the title compound (0.9 g) as a white solid.

$^1$H-NMR(CDCl$_3$): 2.22(3H,s), 3.16(3H,s), 3.80-4.20(2H, m), 4.38(2H,q,J=7.8 Hz), 4.60-5.10(4H,m), 6.64(1H,d,J=5.8 Hz), 7.29-7.40(2H,m), 7.47-7.52(2H,m), 7.81-7.89(2H,m), 8.14(1H,d,J=7.8 Hz), 8.34(1H,d,J=5.8 Hz), 8.75-8.79(1H, m).

Example 13

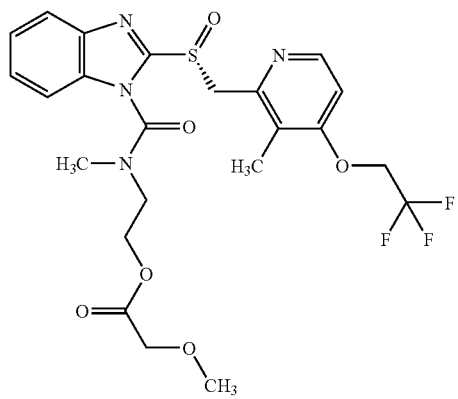

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl methoxyacetate To a solution (15 mL) of bis(trichloromethyl)carbonate (0.652 g) in tetrahydrofuran was dropwise added a solution (1 mL) of pyridine (0.55 mL) in tetrahydrofuran under ice-cooling. After stirring under ice-cooling for 30 min., 2-(methylamino)ethyl methoxyacetate (0.99 g) obtained in Reference Example 13 was added. The mixture was stirred at room temperature for 3 hrs. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (15 mL). (R)-2-[[[3-Methyl-4-(2,2,2-trifluoroethoxy)-2-pyridyl]methyl]sulfinyl]-1H-benzimidazole (1.13 g), triethylamine (0.86 mL) and 4-dimethylaminopyridine (0.037 g) were added, and the mixture was stirred at 60° C. for 4 days. After concentration under reduced pressure, ethyl acetate (80 mL) and water (30 mL) were added to the residue, and the mixture was stirred. The ethyl acetate layer was separated and taken, and the ethyl acetate layer was washed with a saturated aqueous sodium hydrogen carbonate solution (30 mL) and water (30 mL), and dried over anhydrous magnesium sulfate. After concentration under reduced pressure, the residue was purified by silica gel column chromatography (eluted with ethyl acetate, then acetone:ethyl acetate=1:3), and further by basic silica gel column chromatography (eluted with ethyl acetate:hexane=1:1, then 3:1) to give the title compound (0.588 g) as colorless syrup.

$^1$H-NMR(CDCl$_3$): 2.32(3H,s), 2.68(3H,s), 3.48(3H,s), 3.69-4.02(4H,m), 4.38(2H,q,J=7.8 Hz), 4.67(2H,t,J=6.6 Hz), 4.99(1H,d,J=13.9 Hz), 5.12(1H,d,J=13.9 Hz), 6.63(1H,d, J=5.7 Hz), 7.29-7.46(2H,m), 7.62(1H,m), 7.81(1H,m), 8.25 (1H,d,J=5.7 Hz).

Example 14

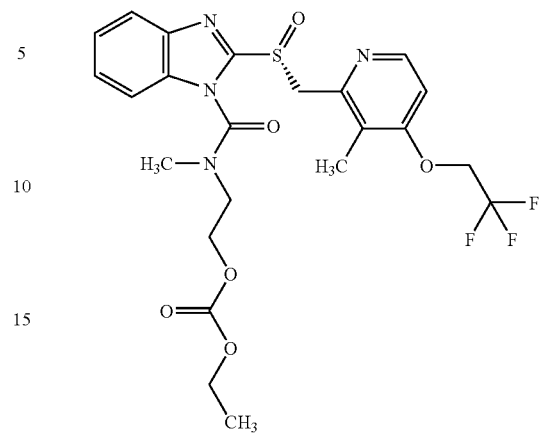

Ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (40 ml) of bis(trichloromethyl)carbonate (1.31 g) in tetrahydrofuran was dropwise added a solution (2 mL) of pyridine (1.07 mL) in tetrahydrofuran under ice-cooling. After stirring under ice-cooling for 10 min., ethyl 2-(methylamino)ethyl carbonate hydrochloride (2.02 g) obtained in Reference Example 14 was added. A solution (2 mL) of triethylamine (1.84 mL) in tetrahydrofuran was dropwise added and the mixture was stirred at room temperature for 1 hr. After concentration under reduced pressure, water (100 mL) was added to the residue, and the mixture was extracted with ethyl acetate (100 mL). The ethyl acetate layer was washed with 0.2N hydrochloric acid (50 mL) and saturated brine (100 mL) and dried over anhydrous magnesium sulfate. After concentration under reduced pressure, the residue was dissolved in tetrahydrofuran (50 mL). (R)-2-[[[3-Methyl-4-(2,2,2-trifluoroethoxy)-2-pyridyl]methyl]sulfinyl]-1H-benzimidazole (3.69 g), triethylamine (2.09 mL) and 4-dimethylaminopyridine (0.12 g) were added, and the mixture was stirred at 60° C. for 6 hrs. and at room temperature for 8 hrs. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was purified by basic silica gel column chromatography (eluted with ethyl acetate:hexane=3:7, then ethyl acetate). Crystallization from diethyl ether and recrystallization from diethyl ether gave the title compound (3.84 g) as a colorless solid.

$^1$H-NMR(CDCl$_3$): 1.32(3H,t,J=7.2 Hz), 2.23(3H,s), 3.10 (3H,bs) 3.50-4.20(2H,br), 4.22(2H,q,J=7.2 Hz), 4.39(2H,q, J=7.9 Hz), 4.45(2H,m), 4.80-5.15(2H,br), 6.65(1H,d,J=5.6 Hz), 7.36-7.50(3H,m), 7.84(1H,d,J=7.8 Hz), 8.35(1H,d, J=5.6 Hz).

Example 15

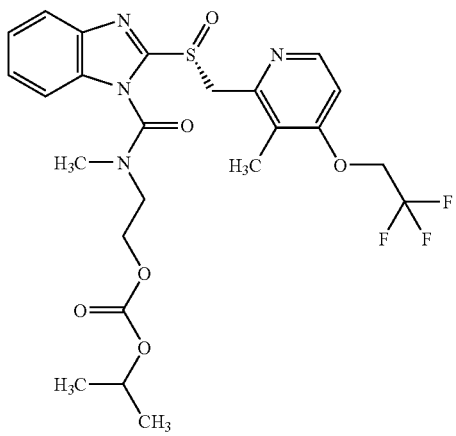

Isopropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., isopropyl 2-(methylamino)ethyl carbonate hydrochloride (0.99 g) obtained in Reference Example 15 was added. A solution (1 mL) of triethylamine (0.70 mL) in tetrahydrofuran was dropwise added and the mixture was stirred at room temperature for 1 hr. Bis(trichloromethyl)carbonate (0.50 g), a solution (1 mL) of pyridine (0.40 mL) in tetrahydrofuran and a solution (1 mL) of triethylamine (0.70 mL) in tetrahydrofuran were successively added and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred at 60° C. for 12 hrs. and at room temperature for 3 days. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2), and further by basic silica gel column chromatography (eluted with ethyl acetate:hexane=3:7, then ethyl acetate). Crystallization from diethyl ether and recrystallization from acetone-diisopropyl ether gave the title compound (0.58 g) as a colorless solid.

$^1$H-NMR(CDCl$_3$): 1.31(6H,d,J=6.3 Hz), 2.23(3H,s), 3.08 (3H,bs), 3.40-4.30(2H,br), 4.37(2H,q,J=7.9 Hz), 4.32-4.53 (2H,m), 4.80-5.20(3H,m), 6.63(1H,d,J=5.7 Hz), 7.35-7.50 (3H,m), 7.83(1H,d,J=7.2 Hz), 8.34(1H,d,J=5.7 Hz).

Example 16

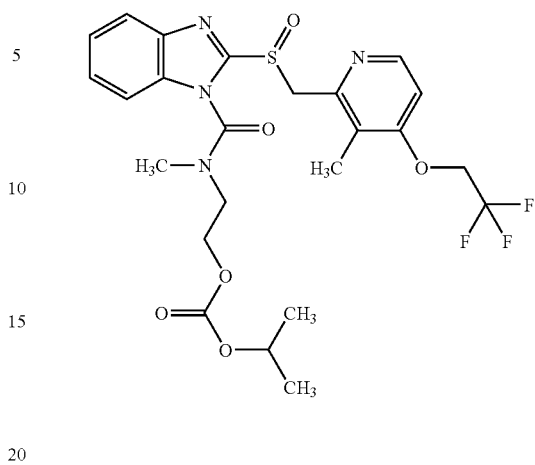

Isopropyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., isopropyl 2-(methylamino)ethyl carbonate hydrochloride (1.18 g) obtained in Reference Example 15 was added. A solution (1 mL) of triethylamine (0.84 mL) in tetrahydrofuran was added and the mixture was stirred at room temperature for 2 hrs. After concentration under reduced pressure, ethyl acetate (80 mL) and water (30 mL) were added to the residue, and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (25 mL). 2-[[[3-Methyl-4-(2,2,2-trifluoroethoxy)-2-pyridyl]methyl]sulfinyl]-1H-benzimidazole (1.73 g), triethylamine (1.31 mL) and 4-dimethylaminopyridine (0.057 g) were added, and the mixture was stirred at 60° C. for 5 hrs. After concentration under reduced pressure, ethyl acetate (100 mL) and water (50 mL) were added to the residue, and the mixture was stirred. The ethyl acetate layer was separated and taken, washed with saturated brine (50 mL) and dried over anhydrous magnesium sulfate. After concentration under reduced pressure, the residue was purified by basic silica gel column chromatography (eluted with ethyl acetate:hexane=1:1), and further by silica gel column chromatography (eluted with ethyl acetate:hexane=1:1, then 2:1). Crystallization from diisopropyl ether-hexane and recrystallization from diisopropyl ether gave the title compound (1.20 g) as a colorless solid.

$^1$H-NMR(CDCl$_3$): 1.31(6H,d,J=6.6 Hz), 2.23(3H,s), 3.08 (3H,bs), 3.50-3.90(2H,bm), 4.38(2H,q,J=7.8 Hz), 4.36-4.58 (2H,bm), 4.79-5.15(3H,m), 6.64(1H,d,J=5.7 Hz), 7.35-7.48 (3H,m), 7.83(1H,d,J=7.5 Hz), 8.34(1H,d,J=5.7 Hz).

Example 17

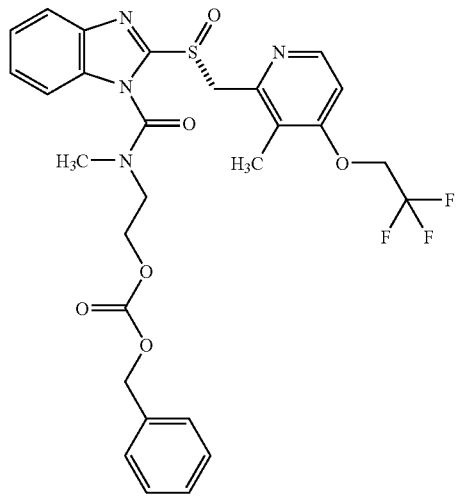

Benzyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., benzyl 2-(methylamino)ethyl carbonate hydrochloride (1.08 g) obtained in Reference Example 16 was added. A solution (1 mL) of triethylamine (0.70 mL) in tetrahydrofuran was dropwise added, and the mixture was stirred overnight at room temperature. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diethyl ether and recrystallization from acetone-diethyl ether gave the title compound (1.17 g) as a colorless solid.

$^1$H-NMR(CDCl$_3$): 2.22(3H,s), 3.05(3H,bs), 3.50-4.20 (2H,br), 4.37(2H,q,J=7.8 Hz), 4.46(2H,m), 4.80-5.10(2H, br), 5.17(2H,s), 6.62(1H,d,J=5.6 Hz), 7.26-7.48(8H,m), 7.77-7.88(1H,m), 8.33(1H,d,J=5.6 Hz).

Example 18

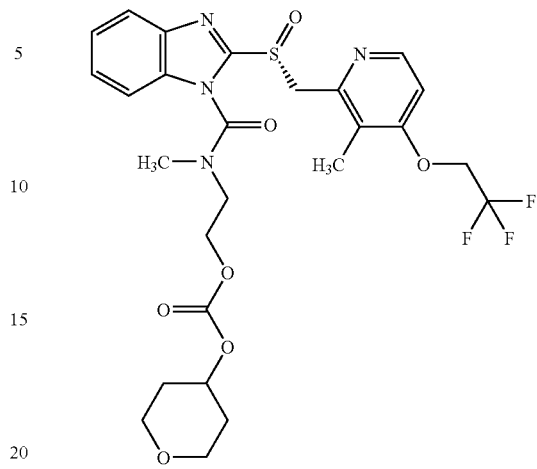

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate To a solution (20 mL) of bis(trichloromethyl)carbonate (0.48 g) in tetrahydrofuran was dropwise added a solution (1 mL) of pyridine (0.39 mL) in tetrahydrofuran under ice-cooling. After stirring under ice-cooling for 20 min., 2-(methylamino)ethyl tetrahydropyran-4-yl carbonate hydrochloride (0.96 g) obtained in Reference Example 17 was added. A solution (1 mL) of triethylamine (0.67 mL) in tetrahydrofuran was dropwise added, and the mixture was stirred at room temperature for 2 hrs. After concentration under reduced pressure, water (50 mL) was added to the residue. The mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.26 g), triethylamine (0.71 mL) and 4-dimethylaminopyridine (0.042 g) were added, and the mixture was stirred at 60° C. for 6 hrs. and at room temperature for 8 hrs. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate). Crystallization from diethyl ether and recrystallization from acetone-diisopropyl ether gave the title compound (1.45 g) as a colorless solid.

$^1$H-NMR(CDCl$_3$): 1.64-1.81(2H,m), 1.92-2.03(2H,m), 2.23(3H,s), 3.09(3H,bs), 3.40-4.30(2H,br), 3.45-3.57(2H, m), 3.87-3.97(2H,m), 4.38(2H,q,J=7.8 Hz), 4.45(2H,m), 4.77-5.15(3H,m), 6.64(1H,d,J=5.7 Hz), 7.35-7.50(3H,m), 7.83(1H,d,J=6.9 Hz), 8.35(1H,d,J=5.7 Hz).

Example 19

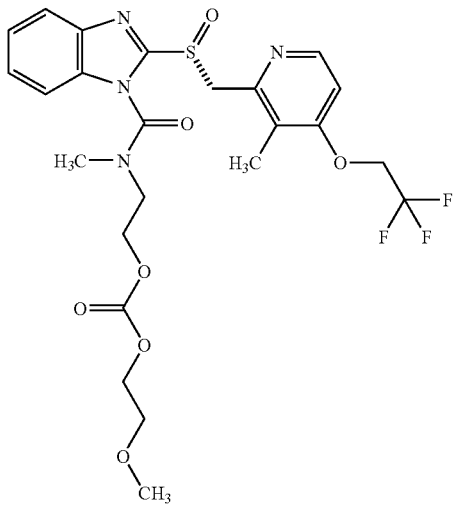

2-Methoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 10 min., 2-methoxyethyl 2-(methylamino)ethyl carbonate hydrochloride (1.07 g) obtained in Reference Example 18 was added. A solution (1 mL) of triethylamine (0.84 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.85 g), triethylamine (1.05 mL) and 4-dimethylaminopyridine (0.061 g) were added, and the mixture was stirred at 60° C. for 6 hrs. and at room temperature for 8 hrs. After concentration under reduced pressure, water (50 mL) was added to the residue. The mixture was extracted with ethyl acetate (50 mL). The ethyl acetate layer was washed with saturated brine (50 ml) and dried over anhydrous magnesium sulfate. After concentration under reduced pressure, the residue was purified by basic silica gel column chromatography (eluted with ethyl acetate:hexane=3:7, then ethyl acetate). Crystallization from ethyl acetate-diethyl ether and recrystallization from ethyl acetate-diisopropyl ether gave the title compound (1.39 g) as a colorless solid.

$^1$H-NMR(CDCl$_3$): 2.23(3H,s), 3.09(3H,bs), 3.37(3H,s), 3.50-4.20(2H,br), 3.59-3.65(-2H,m), 4.28-4.33(2H,m), 4.38(2H,q,J=7.8 Hz), 4.46(2H,m), 4.80-5.15(2H,br), 6.64(1H,d,J=5.7 Hz), 7.35-7.47(3H,m), 7.83(1H,d,J=7.8 Hz), 8.34(1H,d,J=5.7 Hz).

Example 20

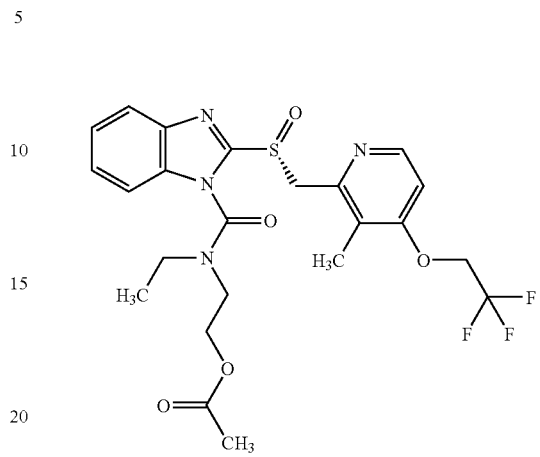

2-[Ethyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (30 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 10 min., 2-(ethylamino)ethyl acetate hydrochloride (0.67 g) obtained in Reference Example 20 was added. A solution (1 mL) of triethylamine (0.84 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate) to give the title compound (1.58 g) as a yellow amorphous solid.

$^1$H-NMR(CDCl$_3$): 1.25(3H,m), 2.08(3H,s), 2.23(3H,s), 3.30-4.10(4H,br), 4.23-4.45(2H,m), 4.38(2H,q,J=7.8 Hz), 4.75-5.20(2H,br), 6.64(1H,d,J=5.7 Hz), 7.35-7.46(3H,m), 7.84(1H,d,J=6.9 Hz), 8.36(1H,d,J=5.7 Hz).

Example 21

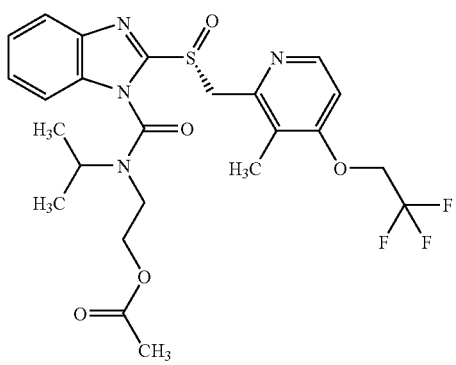

2-[Isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (10 mL) of bis(trichloromethyl)carbonate (0.543 g) in tetrahydrofuran was dropwise added a solution (5 mL) of pyridine (0.445 mL) in tetrahydrofuran under ice-cooling, and the mixture was stirred at 0° C. for 30 min. 2-(Isopropylamino)ethyl acetate hydrochloride (1.0 g) obtained in Reference Example 22 was added. A solution (5 mL) of triethylamine (0.805 mL) in tetrahydrofuran was dropwise added, and the mixture was stirred at room temperature for 30 min. The reaction mixture was concentrated under reduced pressure, water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The obtained oil was dissolved in tetrahydrofuran (5 mL), and added to a solution (20 mL) of (R)-2-[[[3-methyl-4-(2,2,2-trifluoroethoxy)-2-pyridyl]methyl]sulfinyl]-1H-benzimidazole (1.73 g), triethylamine (1.53 mL) and 4-dimethylaminopyridine (0.134 g) in tetrahydrofuran. The mixture was stirred at 40° C. for 12 hrs. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The residue was purified by silica gel column chromatography (eluted with ethyl acetate:hexane=2:1, then ethyl acetate) to give the title compound (1.50 g) as a pale-yellow amorphous solid.

$^1$H-NMR(CDCl$_3$): 1.20-1.40(6H,m), 2.05(3H×0.4,s), 2.11(3H×0.6,s), 2.18(3H×0.6,s), 2.27(3H×0.4,s), 3.40-3.60(1H,m), 3.70-4.60(6H,m), 4.70-5.25(2H,m), 6.65(1H,d,J=5.8 Hz), 7.30-7.50(3H,m), 7.75-7.90(1H,m), 8.37(1H,d,J=5.8 Hz).

Example 22

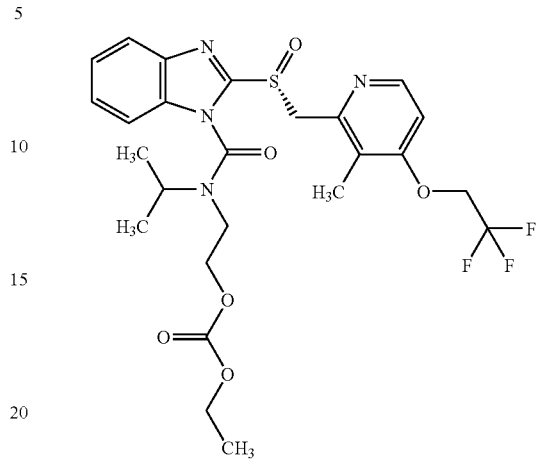

Ethyl 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (10 mL) of bis(trichloromethyl)carbonate (0.467 g) in tetrahydrofuran was dropwise added a solution (5 mL) of pyridine (0.381 mL) in tetrahydrofuran under ice-cooling, and the mixture was stirred at 0° C. for 30 min. Ethyl 2-(isopropylamino)ethyl carbonate hydrochloride (1.0 g) obtained in Reference Example 23 was added to the reaction mixture. A solution (5 mL) of triethylamine (0.69 ml) in tetrahydrofuran was dropwise added, and the mixture was stirred at 0° C. for 15 min. and at room temperature for 30 min. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The obtained oil was dissolved in tetrahydrofuran (5 mL), and added to a solution (20 mL) of (R)-2-[[[3-methyl-4-(2,2,2-trifluoroethoxy)-2-pyridyl]methyl]sulfinyl]-1H-benzimidazole (1.48 g), triethylamine (1.32 mL) and 4-dimethylaminopyridine (0.115 g) in tetrahydrofuran, and the mixture was stirred at 40° C. for 12 hrs. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The residue was purified by silica gel column chromatography (eluted with ethyl acetate:hexane=2:1, then ethyl acetate) to give the title compound (1.20 g) as a pale-yellow amorphous solid.

$^1$H-NMR(CDCl$_3$): 1.20-1.40(9H,m), 2.17(3H×0.6,s), 2.27(3H×0.4,s), 3.40-3.70(1H,m), 3.75-4.65(8H,m), 4.70-5.30(2H,m), 6.64(1H,d,J=5.8 Hz), 7.35-7.55(3H,m), 7.75-7.90(1H,m), 8.38(1H,d,J=5.8 Hz).

Example 23

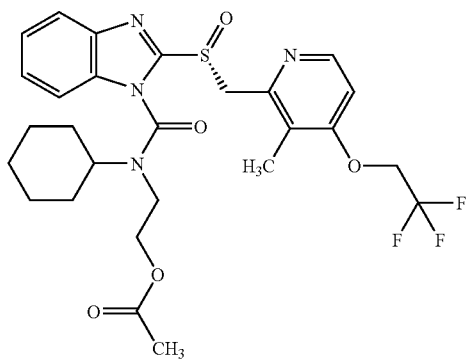

2-[Cyclohexyl[[(R)-2-[[[3-methyl-4-(2,2,2-trifluoro-ethoxy)-2-pyridyl]methyl]sulfinyl]-1H-benzimidazol-1-yl]carbonyl]amino]ethyl acetate To a solution (10 mL) of bis(trichloromethyl)carbonate (0.593 g) in tetrahydrofuran was dropwise added pyridine (0.485 mL) under ice-cooling. After stirring under ice-cooling for 30 min., 2-(cyclohexylamino)ethyl acetate hydrochloride (1.33 g) obtained in Reference Example 25 was added. Triethylamine (0.84 mL) was dropwise added, and the mixture was stirred at room temperature for 2 hrs. Ethyl acetate (50 mL) was added to the reaction mixture and the mixture was washed with water (50 mL) and saturated brine (50 mL), dried over anhydrous magnesium sulfate and concentrated under reduced pressure. The residue was dissolved in tetrahydrofuran (20 mL), and (R)-2-[[[3-methyl-4-(2,2,2-trifluoroethoxy)-2-pyridyl]methyl]sulfinyl]-1H-benzimidazole (1.61 g), triethylamine (1.21 mL) and 4-dimethylaminopyridine (0.053 g) were added. The mixture was stirred at 60° C. for 24 hrs. Ethyl acetate (50 mL) was added to the reaction mixture, and the mixture was washed with water (20 mL) and saturated brine (50 mL), dried over anhydrous sodium sulfate, and concentrated under reduced pressure. The residue was purified by flash silica gel column chromatography (eluted with ethyl acetate:hexane=1:4, then ethyl acetate) to give the title compound (2.12 g) as a pale-yellow amorphous solid.

$^1$H-NMR(CDCl$_3$): 1.00-2.42(16H,m), 3.30-3.70(2H,m), 3.80-4.00(1H,m), 4.27-4.42(2H,m), 4.40(2H,q,J=8.2 Hz), 4.78(1H×0.5,d,J=13.2 Hz), 4.97(2H×0.5,s), 5.20(1H×0.5,d, J=13.2 Hz), 6.67(1H,d,J=5.8 Hz), 7.36-7.46(3H,m), 7.81-7.91(1H,m), 8.39(1H,d,J=5.8 Hz).

Example 24

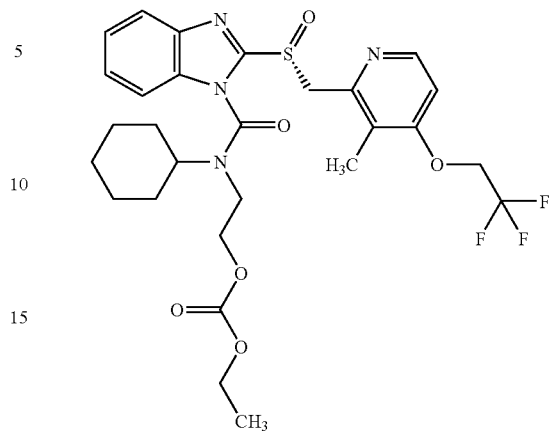

2-[Cyclohexyl[[(R)-2-[[[3-methyl-4-(2,2,2-trifluoro-ethoxy)-2-pyridyl]methyl]sulfinyl]-1H-benzimidazol-1-yl]carbonyl]amino]ethyl ethyl carbonate To a solution (10 mL) of bis(trichloromethyl)carbonate (0.238 g) in tetrahydrofuran was dropwise added pyridine (0.20 mL) under ice-cooling. After stirring under ice-cooling for 30 min., 2-(cyclohexylamino)ethyl ethyl carbonate hydrochloride (0.605 g) obtained in Reference Example 26 was added. Triethylamine (0.335 mL) was dropwise added, and the mixture was stirred at room temperature for 2 hrs. Ethyl acetate (50 mL) was added to the reaction mixture, and the mixture was washed with water (50 mL) and saturated brine (50 mL), dried over anhydrous magnesium sulfate and concentrated under reduced pressure. The residue was dissolved in tetrahydrofuran (10 mL), and (R)-2-[[[3-methyl-4-(2,2,2-trifluoroethoxy)-2-pyridyl]methyl]sulfinyl]-1H-benzimidazole (0.60 g), triethylamine-(0.45 mL) and 4-dimethylaminopyridine (0.02 g) were added. The mixture was stirred at 60° C. for 24 hrs. Ethyl acetate (50 mL) was added to the reaction mixture, and the mixture was washed with water (20 mL) and saturated brine (50 mL), dried over anhydrous sodium sulfate, and concentrated under reduced pressure. The residue was purified by flash silica gel column chromatography (eluted with ethyl acetate:hexane=1:4, then ethyl acetate) to give the title compound (0.92 g) as a pale-yellow amorphous solid.

$^1$H-NMR(CDCl$_3$): 1.02-2.27(16H,m), 3.40-4.60(9H,m) 4.78(1H×0.5,d,J=13.2 Hz), 4.97(2H×0.5,s), 5.44(1H×0.5,d, J=13.2 Hz), 6.69(1H,d,J=5.6 Hz), 7.32-7.54(3H,m), 7.80-7.91(1H,m), 8.38(1H,d,J=5.6 Hz).

Example 25

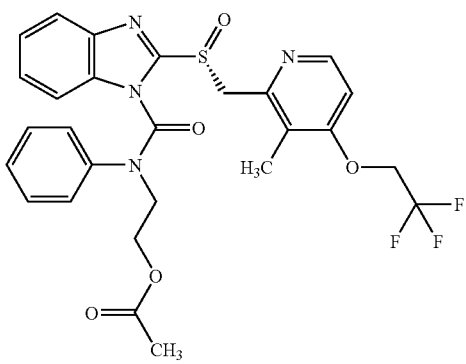

2-[[[(R)-2-[[[3-Methyl-4-(2,2,2-trifluoroethoxy)-2-pyridyl]methyl]sulfinyl]-1H-benzimidazol-1-yl]carbonyl](phenyl)amino]ethyl acetate To a solution (350 mL) of bis(trichloromethyl)carbonate (13.4 g) in tetrahydrofuran was dropwise added pyridine (10.38 mL) under ice-cooling. After stirring under ice-cooling for 30 min., 2-anilinoethyl acetate hydrochloride (25.9 g) obtained in Reference Example 27 was added. Triethylamine (18.4 mL) was dropwise added, and the mixture was stirred at room temperature for 2 hrs. After concentration under reduced pressure, ethyl acetate (500 mL) and water (500 mL) were added to the residue, and the mixture was stirred. The ethyl acetate layer was separated and taken, washed with saturated brine (500 mL), dried over anhydrous magnesium sulfate and concentrated under reduced pressure to give 2-[(chlorocarbonyl) (phenyl)amino]ethyl acetate. This was dissolved in tetrahydrofuran (300 mL), (R)-2-[[[3-methyl-4-(2,2,2-trifluoroethoxy)-2-pyridyl]methyl]sulfinyl]-1H-benzimidazole (41.2 g), triethylamine (15.6 mL) and 4-dimethylaminopyridine (1.363 g) were added, and the mixture was stirred at 60° C. for 3 hrs. Ethyl acetate (800 mL) was added to the reaction mixture, and the mixture was washed twice with water (800 mL) and with saturated brine (800 mL), dried over anhydrous sodium-sulfate, and concentrated under reduced pressure. The residue was purified by basic silica gel column chromatography (eluted with ethyl acetate:hexane=3:7, then 1:1). Crystallization from diethyl ether gave the title compound (54.1 g) as a white solid.

$^1$H-NMR(CDCl$_3$): 2.00(3H,s), 2.25(3H,s), 4.15-4.48(6H, m), 4.83(1H,d,J=13.6 Hz), 5.05(1H,d,J=13.6 Hz), 6.67(1H, d,J=5.4 Hz), 7.03-7.45(8H,m), 7.64-7.69(1H,m), 8.40(1H,d, J=5.4 Hz).

Example 26

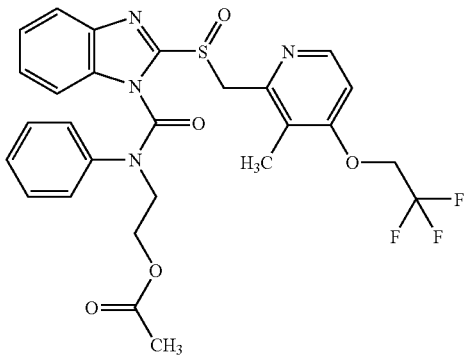

2-[[[2-[[[3-Methyl-4-(2,2,2-trifluoroethoxy)-2-pyridyl]methyl]sulfinyl]-1H-benzimidazol-1-yl]carbonyl](phenyl)amino]ethyl acetate To a solution (10 mL) of 2-[(chlorocarbonyl)(phenyl) amino]ethyl acetate (0.58 g) prepared in the same manner as in Example 25 in tetrahydrofuran were added 2-[[[3-methyl-4-(2,2,2-trifluoroethoxy)-2-pyridyl]methyl]sulfinyl]-1H-benzimidazole (0.739 g), triethylamine (0.558 mL) and 4-dimethylaminopyridine (0.024 g), and the mixture was stirred at 60° C. for 15 hrs. Ethyl acetate (30 mL) was added to the reaction mixture, and the mixture was washed with water (50 mL) and saturated brine (50 mL), dried over anhydrous sodium sulfate, and concentrated under reduced pressure. The residue was purified by flash silica gel column chromatography (eluted with acetone:hexane=1:4, then 3:2). Crystallization from diethyl ether gave the title compound (0.779 g) as a white solid.

$^1$H-NMR(CDCl$_3$): 1.99(3H,s), 2.25(3H,s), 4.20-4.48(6H, m) 4.83(1H,d,J=13.6 Hz), 5.05(1H,d,J=13.6 Hz), 6.67(1H,d, J=5.8 Hz), 7.03-7.45(8H,m), 7.64-7.69(1H,m), 8.40(1H,d, J=5.8 Hz).

Example 27

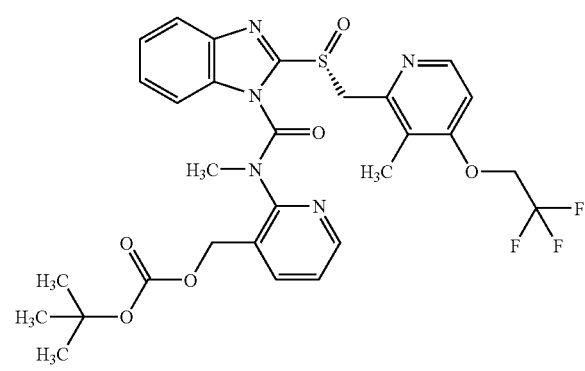

tert-Butyl[2-[methyl[[(R)-2-[[[3-methyl-4-(2,2,2-trifluoroethoxy)-2-pyridyl]methyl]sulfinyl]-1H-benzimidazol-1-yl]carbonyl]amino]-3-pyridyl]methyl carbonate To a solution (20 mL) of bis(trichloromethyl)carbonate (0.30 g) in tetrahydrofuran was dropwise added pyridine (0.24 mL) under ice-cooling. After stirring under ice-cooling for 30 min., tert-butyl[2-(methylamino)-3-pyridyl]methyl carbonate (0.71 g) obtained in Reference Example 28 was added, and the mixture was stirred at room temperature for 2 hrs. The precipitated solid was filtered off and the filtrate was concentrated under reduced pressure. The residue was dissolved in tetrahydrofuran (20 mL), (R)-2-[[[3-methyl-4-(2,2, 2-trifluoroethoxy)-2-pyridyl]methyl]sulfinyl]-1H-benzimidazole (0.92 g), triethylamine (0.70 mL) and 4-dimethylaminopyridine (0.031 g) were added, and the mixture was stirred at 60° C. for 1 hr. Water (50 mL) was added to the reaction mixture and the mixture was extracted twice with ethyl acetate (50 mL). The ethyl acetate layer was washed with saturated brine (50 mL), dried over anhydrous sodium sulfate, and concentrated under reduced pressure. The residue was purified by flash silica gel column chromatography (eluted with acetone:hexane=1:2), and further by basic silica gel column chromatography (eluted with ethyl acetate) to give the title compound (0.38 g) as a pale-yellow amorphous solid.

$^1$H-NMR(CDCl$_3$): 1.46(9H,s), 2.25(3H,s), 3.54(3H,s), 4.37(2H,q,J=8.0 Hz), 4.95(2H,s), 5.15(1H,d,J=14.0 Hz), 5.27(1H,d,J=14.0 Hz), 6.63(1H,d,J=5.4 Hz), 7.26-7.45(3H, m), 7.69-7.87(3H,m), 8.33(1H,d,J=5.4 Hz), 8.44-8.46(1H, m).

Example 28

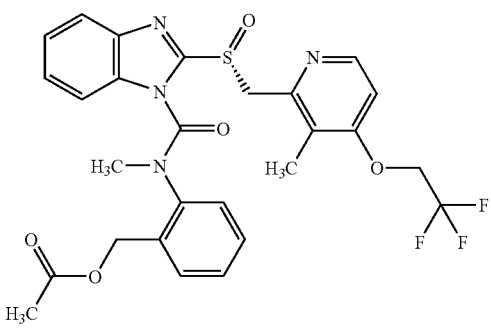

2-[Methyl[[(R)-2-[[[3-methyl-4-(2,2,2-trifluoroethoxy)-2-pyridyl]methyl]sulfinyl]-1H-benzimidazol-1-yl]carbonyl]amino]benzyl acetate To a solution (30 mL) of bis(trichloromethyl)carbonate (1.46 g) in tetrahydrofuran was dropwise added pyridine (1.16 mL) under ice-cooling. After stirring under ice-cooling for 30 min., 2-(methylamino)benzyl acetate (2.57 g) obtained in Reference Example 29 was added. The mixture was stirred at room temperature for 3 hrs. The precipitated solid was filtered off and the filtrate was concentrated under reduced pressure. The residue was dissolved in tetrahydrofuran (40 mL), (R)-2-[[[3-methyl-4-(2,2,2-trifluoroethoxy)-2-pyridyl]methyl]sulfinyl]-1H-benzimidazole (4.41 g), triethylamine (3.33 mL) and 4-dimethylaminopyridine (0.15 g) were added, and the mixture was stirred at 60° C. for 18 hrs. Water (100 mL) was added to the reaction mixture, and the mixture was extracted with ethyl acetate (100 mL). The ethyl acetate layer was washed with saturated brine (100 mL), dried over anhydrous sodium sulfate, and concentrated under reduced pressure. The residue was purified by flash silica gel column chromatography (eluted with acetone:hexane=1:4, then 1:2). Crystallization from ethyl acetate-diethyl ether-hexane gave the title compound (2.76 g) as a white solid.

$^1$H-NMR(CDCl$_3$): 2.10(3H,s), 2.00-2.30(3H,br), 3.20-3.50(3H,br), 4.38(2H,q,J=7.6 Hz), 4.70-5.20(2H,m), 5.20-5.50(2H,m), 6.65(1H,d,J=5.4 Hz), 7.10-7.82(8H,m), 8.38 (1H,d,J=5.4 Hz).

Example 29

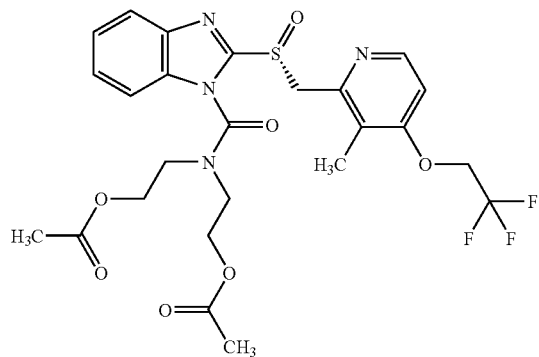

2-[[2-(Acetyloxy)ethyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 10 min., 2-[(2-acetyloxyethyl)amino]ethyl acetate hydrochloride (1.13 g) obtained in Reference Example 30 was added. A solution (1 mL) of triethylamine (0.70 mL) in tetrahydrofuran was dropwise added, and the mixture was stirred at room temperature for 2 hrs. The precipitated solid was filtered off and the filtrate was concentrated under reduced pressure. Ethyl acetate (20 mL) was added to the residue, the precipitated solid was filtered off and the filtrate was concentrated under reduced pressure. The residue was dissolved in tetrahydrofuran (30 mL). (R)-2-[[[3-Methyl-4-(2,2,2-trifluoroethoxy)-2-pyridyl]methyl]sulfinyl]-1H-benzimidazole (1.48 g), triethylamine (1.12 mL) and 4-dimethylaminopyridine (catalytic amount) were added, and the mixture was stirred at 60° C. overnight. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by silica gel column chromatography (eluted with ethyl acetate:hexane=1:1, then ethyl acetate), and further by basic silica gel column chromatography (eluted with ethyl acetate:hexane=1:1, then ethyl acetate). The resulting product was dissolved in ethyl acetate (20 mL), activated carbon was added and the mixture was stirred overnight. The activated carbon was filtered off and the filtrate was concentrated under reduced pressure to give the title compound (1.60 g) as a yellow amorphous solid.

$^1$H-NMR(CDCl$_3$): 2.06(3H,s), 2.08(3H,s), 2.24(3H,s), 3.40-4.45(8H,m), 4.39(2H,q,J=7.9 Hz), 4.88(1H,d,J=13.2 Hz), 5.05(1H,d,J=13.2 Hz), 6.66(1H,d,J=5.6 Hz), 7.38-7.50 (3H,m), 7.87(1H,d,J=6.9 Hz), 8.36(1H,d,J=5.6 Hz).

Example 30

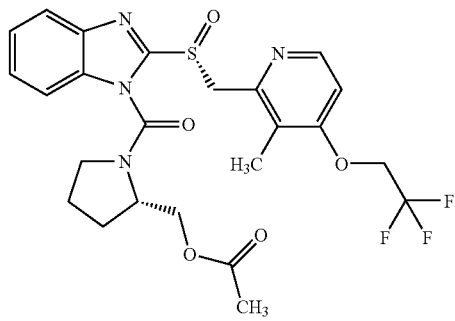

[(2S)-1-[[(R)-2-[[[3-Methyl-4-(2,2,2-trifluoroethoxy)-2-pyridyl]methyl]sulfinyl]-1H-benzimidazol-1-yl]carbonyl]-2-pyrrolidinyl]methyl acetate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., (S)-2-pyrrolidinylmethyl acetate hydrochloride (0.90 g) obtained in Reference Example 31 was added. A solution (1 mL) of triethylamine (0.70 mL) in tetrahydrofuran was dropwise added, and the mixture was stirred at room temperature for 2 hrs. After concentration under reduced pressure, water (50 mL) was added to the residue, and the mixture was extracted with ethyl acetate (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]

methyl]sulfinyl]-1H-benzimidazole (1.11 g), triethylamine (0.84 mL) and 4-dimethylaminopyridine (0.037 g) were added, and the mixture was stirred at 60° C. for 1 day and at room temperature for 2 days. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate) and further by silica gel column chromatography (eluted with ethyl acetate:hexane=3:1, then ethyl acetate, then acetone:ethyl acetate=1:4, then 2:3) to give the title compound (0.80 g) as a pale-yellow amorphous solid.

$^1$H-NMR(CDCl$_3$): 1.80-2.30(4H,m), 2.09(3H,s), 2.30(3H, s), 3.39(1H,m), 3.50-3.62(1H,m), 4.20-4.45(4H,m), 4.58(1H,m), 4.89(1H,d,J=13.5 Hz), 4.96(1H,d,J=13.5 Hz), 6.65(1H,d,J=5.9 Hz), 7.36-7.48(3H,m), 7.89(1H,d,J=8.7 Hz), 8.38(1H,d,J=5.9 Hz).

Example 31

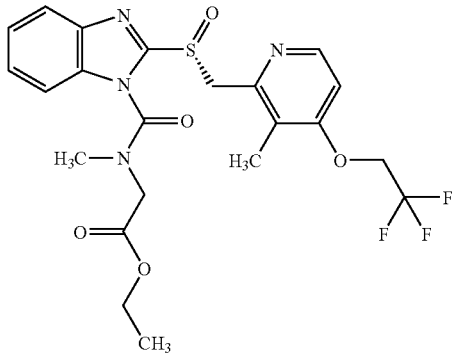

Ethyl[[methyl[[(R)-2-[[[3-methyl-4-(2,2,2-trifluoro-ethoxy)-2-pyridyl]methyl]sulfinyl]-1H-benzimida-zol-1-yl]carbonyl]amino]acetate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 30 min., sarcosine ethyl ester hydrochloride (0.77 g) was added. A solution (1 ml) of triethylamine (0.70 mL) in tetrahydrofuran was dropwise added and the mixture was stirred at room temperature for 1 hr. The precipitated solid was filtered off and the filtrate was concentrated under reduced pressure. Water (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was dissolved in tetrahydrofuran (33 mL). (R)-2-[[[3-Methyl-4-(2,2,2-trifluoroethoxy)-2-pyridyl]methyl]sulfinyl]-1H-benzimidazole sodium (1.37 g) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate) to give the title compound (0.40 g) as a yellow amorphous solid.

$^1$H-NMR(CDCl$_3$): 1.33(3H,t,J=7.1 Hz), 2.24(3H,s), 3.10 (3H,bs), 3.70-4.30(2H,br), 4.28(2H,q,J=7.1 Hz), 4.38(2H,q, J=7.8 Hz), 4.82-5.10(2H,br), 6.63(1H,d,J=5.5 Hz), 7.34-7.52 (2H,m), 7.70-7.90(2H,m), 8.32(1H,d,J=5.5H).

Example 32

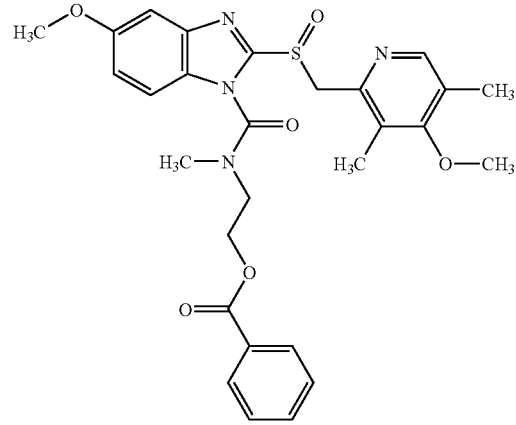

2-[[[5-Methoxy-2-[[(4-methoxy-3,5-dimethyl-2-pyridyl)methyl]sulfinyl]-1H-benzoimidazol-1-yl] carbonyl](methyl)amino]ethyl benzoate To a solution (10 mL) of bis(trichloromethyl)carbonate (0.344 g) in tetrahydrofuran was dropwise added a solution (5 mL) of pyridine (0.281 mL) in tetrahydrofuran under ice-cooling, and the mixture was stirred at 0° C. for 30 min. 2-(Methylamino)ethyl benzoate hydrochloride (0.750 g) obtained in Reference Example 5 was added. A solution (5 mL) of triethylamine (0.485 mL) in tetrahydrofuran was added, and the mixture was stirred at 0° C. for 1 hr. and at room temperature for 30 min. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The obtained oil was dissolved in tetrahydrofuran (5 mL), added to a solution (10 mL) of 5-methoxy-2-[[(4-methoxy-3,5-dimethyl-2-pyridyl)methyl]sulfinyl]-1H-benzoimidazole (1.0 g), triethylamine (0.808 mL) and 4-dimethylaminopyridine (0.071 g) in tetrahydrofuran, and the mixture was stirred at 40° C. for 18 hrs. The reaction mixture was concentrated under reduced pressure and water (30 mL) was added to the residue. The mixture was extracted with ethyl acetate (50 ml). The ethyl acetate layer was washed with saturated brine (30 mL), dried over anhydrous sodium sulfate, and concentrated under reduced pressure. The residue was purified by silica gel column chromatography (eluted with ethyl acetate:hexane=1:1, then ethyl acetate) to give a 1:1 mixture (1.50 g) of the title compound and 2-[[[6-methoxy-2-[[(4-methoxy-3,5-dimethyl-2-pyridyl)methyl]sulfinyl]-1H-benzoimidazol-1-yl] carbonyl](methyl)amino]ethyl benzoate as a pale-yellow amorphous solid.

$^1$H-NMR(CDCl$_3$): 2.05-2.35(6H,m), 3.00-3.30(3H,br), 3.60-4.40(8H,m), 4.60-5.10(4H,m), 6.80-7.00(2H,m), 7.20-7.70(4H,m), 7.95-8.25(3H,m).

Example 33

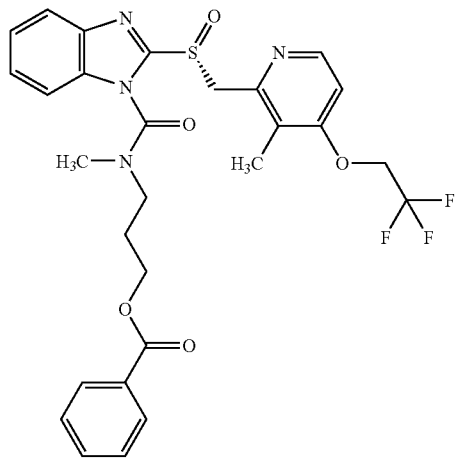

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propyl benzoate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 1 hr., 3-(methylamino)propyl benzoate hydrochloride (1.38 g) obtained in Reference Example 32 was added. A solution (1 mL) of triethylamine (0.84 mL) in tetrahydrofuran was dropwise added, and the mixture was stirred at room temperature for 2 hrs. After concentration under reduced pressure, water (40 mL) was added to the residue, and the mixture was extracted with ethyl acetate (80 mL). The ethyl acetate layer was washed with saturated brine (25 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.63 g), triethylamine (1.23 mL) and 4-dimethylaminopyridine (0.054 g) were added, and the mixture was stirred at 60° C. for 4 hrs. After concentration under reduced pressure, water (40 mL) was added to the residue, and the mixture was extracted with ethyl acetate (80 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1) to give the title compound (1.26 g) as a yellow amorphous solid.

$^1$H-NMR(CDCl$_3$): 2.21(3H,s), 2.20-2.30(2H,bm), 3.06(3H,bs), 3.60-3.75(2H,bm), 4.36(2H,q,J=7.8 Hz), 4.30-4.50(2H,bm), 4.80-5.15(2H,bm), 6.62(1H,d,J=5.7 Hz), 7.26-7.44(5H,m), 7.54(1H,m), 7.81(1H,m), 7.93-8.03(2H,bm), 8.35(1H,d,J=5.7 Hz).

Example 34

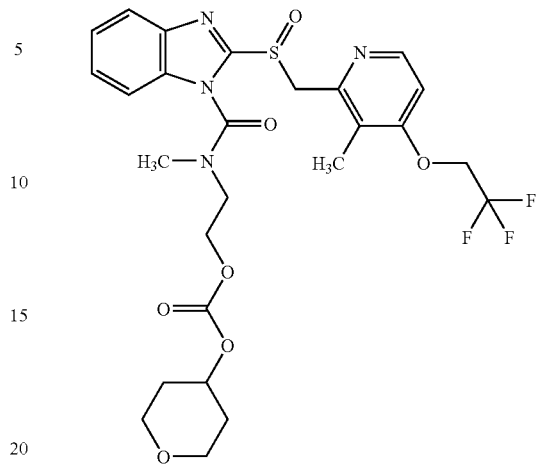

2-[Methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 20 min., 2-(methylamino)ethyl tetrahydropyran-4-yl carbonate hydrochloride (1.43 g) obtained in Reference Example 17 was added. A solution (1 mL) of triethylamine (0.84 mL) in tetrahydrofuran was dropwise added, and the mixture was stirred at room temperature for 3 hrs. After concentration under reduced pressure, water (30 mL) was added to the residue, and the mixture was extracted with ethyl acetate (80 mL). The ethyl acetate layer was washed with saturated brine (20 mL), dried over anhydrous magnesium sulfate and concentrated under reduced pressure. The residue was dissolved in tetrahydrofuran (20 mL). 2-[[[3-Methyl-4-(2,2,2-trifluoroethoxy)-2-pyridyl]methyl]sulfinyl]-1H-benzimidazole (1.63 g), triethylamine (1.23 mL) and 4-dimethylaminopyridine (0.027 g) were added, and the mixture was stirred at 60° C. for 17.5 hrs. After concentration under reduced pressure, water (50 mL) was added to the residue, and the mixture was extracted with ethyl acetate (120 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1), then by silica gel column chromatography (eluted with ethyl acetate:hexane=1:1, then 2:1). Crystallization from diethyl ether gave the title compound (1.23 g) as a colorless solid.

$^1$H-NMR(CDCl$_3$): 1.64-1.81(2H,m), 1.92-2.03(2H,m), 2.23(3H,s), 3.10(3H,bs), 3.40-4.30(2H,br), 3.46-3.59(2H,m), 3.87-3.99(2H,m), 4.39(2H,q,J=7.9 Hz), 4.45(2H,m), 4.77-5.15(3H,m), 6.65(1H,d,J=5.4 Hz), 7.35-7.50(3H,m), 7.85(1H,m), 8.36(1H,d,J=5.4 Hz).

Example 35

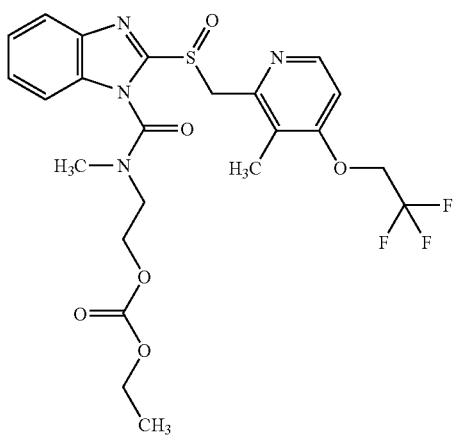

Ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 30 min., ethyl 2-(methylamino)ethyl carbonate hydrochloride (1.10 g) obtained in Reference Example 14 was added. A solution (1 mL) of triethylamine (0.84 mL) in tetrahydrofuran was dropwise added, and the mixture was stirred at room temperature for 3 hrs. After concentration under reduced pressure, water (30 mL) was added to the residue, and the mixture was extracted with ethyl acetate (80 mL). The ethyl acetate layer was washed with saturated brine (30 mL) and dried over anhydrous magnesium sulfate. The layer was concentrated under reduced pressure, and the residue was dissolved in tetrahydrofuran (20 mL). 2-[[[3-Methyl-4-(2,2,2-trifluoroethoxy)-2-pyridyl]methyl]sulfinyl]-1H-benzimidazole (1.63 g), triethylamine (1.23 mL), 4-dimethylaminopyridine (0.054 g) was added, and the mixture was stirred at 60° C. for 14 hrs. After concentration under reduced pressure, water (40 mL) was added to the residue, and the mixture was extracted with ethyl acetate (100 mL). The ethyl acetate layer was washed with saturated brine (30 mL), and dried over anhydrous magnesium sulfate. After concentration under reduced pressure, the residue was purified by basic silica gel column chromatography (eluted with ethyl acetate:hexane=1:2, then 1:1), and then by silica gel column chromatography (eluted with ethyl acetate:hexane=1:1, then 2:1) to give the title compound (1.27 g) as a yellow amorphous solid.

$^1$H-NMR(CDCl$_3$): 1.32(3H,t,J=7.1 Hz), 2.23(3H,s), 3.09 (3H,bs), 3.50-4.76(4H,br), 4.21(2H,q,J=7.1 Hz), 4.38(2H,q, J=7.9 Hz), 4.84-5.14(2H,m), 6.64(1H,d,J=5.6 Hz), 7.36-7.46 (3H,m), 7.83(1H,d,J=7.2 Hz), 8.34(1H,d,J=5.6 Hz).

Example 36

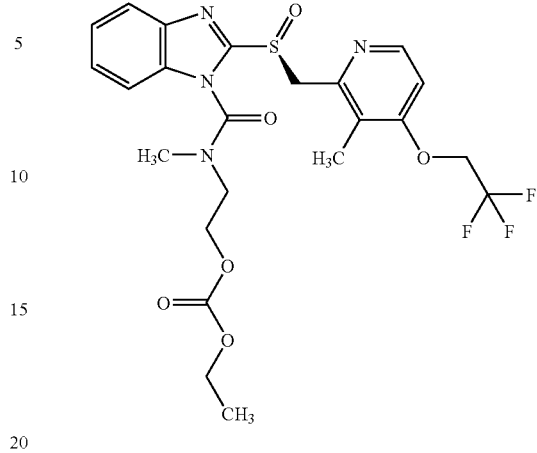

Ethyl 2-[methyl[[(S)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 1 hr., ethyl 2-(methylamino)ethyl carbonate hydrochloride (1.10 g) obtained in Reference Example 14 was added. A solution (1 mL) of triethylamine (0.84 mL) in tetrahydrofuran was dropwise added, and the mixture was stirred at room temperature for 2 hrs. After concentration under reduced pressure, water (30 mL) was added to the residue, and the mixture was extracted with ethyl acetate (80 mL). The ethyl acetate layer was washed with saturated brine (30 mL), and dried over anhydrous magnesium sulfate. The layer was concentrated under reduced pressure, and the residue was dissolved in tetrahydrofuran (20 mL). (S)-2-[[[3-Methyl-4-(2,2,2-trifluoroethoxy)-2-pyridyl]methyl]sulfinyl]-1H-benzimidazole (1.15 g), triethylamine (0.87 mL) and 4-dimethylaminopyridine (0.035 g) were added, and the mixture was stirred at 60° C. for 12 hrs. After concentration under reduced pressure, water (30 mL) was added to the residue, and the mixture was extracted with ethyl acetate (100 mL). The ethyl acetate layer was washed with saturated brine (30 mL), and dried over anhydrous magnesium sulfate. After concentration under reduced pressure, the residue was purified by basic silica gel column chromatography (eluted with ethyl acetate:hexane=1:2, then 1:1). Crystallization from diethyl ether gave the title compound (0.40 g) as a colorless solid.

$^1$H-NMR(CDCl$_3$): 1.32(3H,t,J=7.2 Hz), 2.23(3H,s), 3.10 (3H,bs) 3.50-4.56(4H,br), 4.22(2H,q,J=7.2 Hz), 4.38(2H,q, J=7.9 Hz), 4.84-5.14(2H,m), 6.65(1H,d,J=5.6 Hz), 7.34-7.50 (3H,m), 7.85(1H,m), 8.36(1H,d,J=5.6 Hz).

Example 37

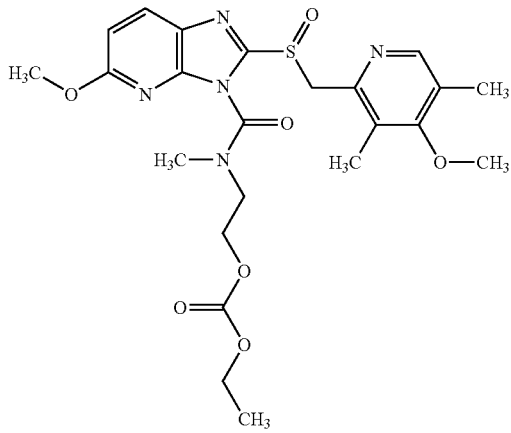

Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 30 min., ethyl 2-(methylamino)ethyl carbonate hydrochloride (1.10 g) obtained in Reference Example 14 was added. A solution (1 mL) of triethylamine (0.84 mL) in tetrahydrofuran was dropwise added, and the mixture was stirred at room temperature for 2.5 hrs. After concentration under reduced pressure, water (30 mL) was added to the residue, and the mixture was extracted with ethyl acetate (80 mL). The ethyl acetate layer was washed with saturated brine (30 mL) and dried over anhydrous magnesium sulfate. The layer was concentrated under reduced pressure, and the residue was dissolved in tetrahydrofuran (20 mL). 5-Methoxy-2-[[(4-methoxy-3,5-dimethyl-2-pyridyl)methyl]sulfinyl]-1H-imidazo[4,5-b]pyridine (1.44 g) synthesized by the method described in JP-A-63-146882, triethylamine (1.16 mL) and 4-dimethylaminopyridine (0.049 g) were added, and the mixture was stirred at 60° C. for 6 hrs. After concentration under reduced pressure, water (30 mL) was added to the residue, and the mixture was extracted with ethyl acetate (100 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 0.1:1). Crystallization from diethyl ether gave the title compound (0.721 g) as a colorless solid.

$^1$H-NMR(CDCl$_3$): 1.25-1.34(3H,m), 2.23(6H,s), 3.15, 3.32(total 3H,s), 3.72(3H,s), 3.90-4.53(9H,m), 4.86(1H,d,J=13.4 Hz), 4.95(1H,d,J=13.4 Hz), 6.79(1H,d,J=8.7 Hz), 7.95(1H,d,J=8.7 Hz), 8.22(1H,s).

Example 38

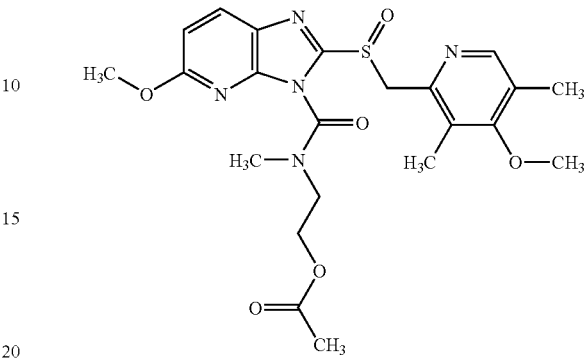

2-[[[5-Methoxy-2-[[(4-methoxy-3,5-dimethyl-2-pyridyl)methyl]sulfinyl]-3H-imidazo[4,5-b]pyridin-3-yl]carbonyl](methyl)amino]ethyl acetate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 30 min., 2-(methylamino)ethyl acetate hydrochloride (0.922 g) obtained in Reference Example 2 was added. A solution (1 mL) of triethylamine (0.84 mL) in tetrahydrofuran was dropwise added, and the mixture was stirred at room temperature for 2 hrs. After concentration under reduced pressure, water (30 mL) was added to the residue, and the mixture was extracted with ethyl acetate (80 mL). The ethyl acetate layer was washed with saturated brine (30 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-imidazo[4,5-b]pyridine (0.85 g) synthesized by the method described in JP-A-63-146882, triethylamine (0.70 mL) and 4-dimethylaminopyridine (0.025 g) were added, and the mixture was stirred at 60° C. for 5 hrs. After concentration under reduced pressure, water (30 mL) was added to the residue, and the mixture was extracted with ethyl acetate (90 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1). Crystallization from diethyl ether gave the title compound (0.173 g) as a colorless solid.

$^1$H-NMR(CDCl$_3$): 2.04,2.09(total 3H,s), 2.24(6H,s), 3.13, 3.30(total 3H,s), 3.45-3.97(2H,m), 3.72(3H,s), 3.97(3H,s), 4.15-4.50(2H,m), 4.85(1H,d,J=13.1 Hz), 4.96(1H,d,J=13.1 Hz), 6.80(1H,d,J=8.9 Hz), 7.96(1H,d,J=8.9 Hz), 8.22(1H,s).

Example 39

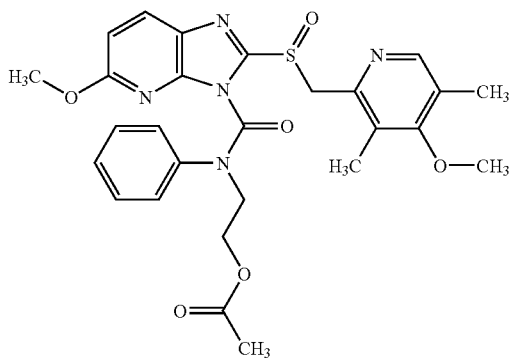

2-[[[5-Methoxy-2-[[(4-methoxy-3,5-dimethyl-2-pyridyl)methyl]sulfinyl]-3H-imidazo[4,5-b]pyridin-3-yl]carbonyl](phenyl)amino]ethyl acetate To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., 2-anilinoethyl acetate hydrochloride (0.647 g) obtained in Reference Example 27 was added. A solution (1 mL) of triethylamine (0.419 mL) in tetrahydrofuran was dropwise added, and the mixture was stirred at room temperature for 3 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-imidazo[4,5-b]pyridine (0.867 g) synthesized by the method described in JP-A-63-146882, triethylamine (0.697 mL) and 4-dimethylaminopyridine (0.020 g) was added, and the mixture was stirred at 60° C. for 10 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:1). Crystallization from diethyl ether gave the title compound (0.311 g) as a colorless solid.

$^1$H-NMR(CDCl$_3$): 1.96(3H,s), 2.23(3H,s), 2.25(3H,s), 3.72(3H,s), 4.01(3H,s), 4.12-4.52(4H,m), 4.78-5.22(2H,m), 6.62(1H,d,J=8.7 Hz), 7.02-7.18(3H,m), 7.32-7.48(2H,m), 7.73(1H,d,J=8.7 Hz), 8.26(1H,s).

Example 40

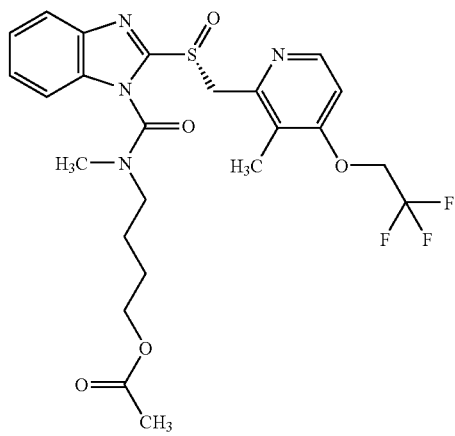

4-[Methyl[[(R)-2-[[[3-methyl-4-(2,2,2-trifluoroethoxy)-2-pyridyl]methyl]sulfinyl]-1H-benzimidazol-1-yl]carbonyl]amino]butyl acetate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., 4-(methylamino)butyl acetate hydrochloride (1.08 g) obtained in Reference Example 37 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.02 g), triethylamine (0.77 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (0.93 g) as a yellow amorphous solid.

$^1$H-NMR(CDCl$_3$): 1.65-1.85(4H,m), 2.03(3H,s), 2.23(3H,s), 3.02(3H,bs), 3.45-3.63(2H,m), 4.03-4.13(2H,m), 4.37 (2H,q,J=7.8 Hz), 4.85-5.13(2H,m), 6.64(1H,d,J=5.6 Hz), 7.36-7.46(3H,m), 7.84(1H,d,J=8.4 Hz), 8.35(1H,d,J=5.6 Hz).

101
Example 41

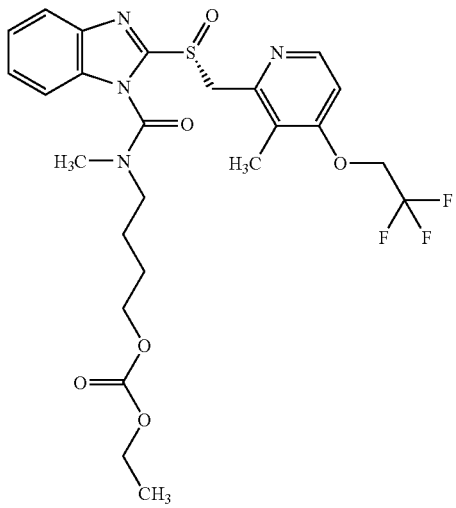

Ethyl 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl carbonate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., ethyl 4-(methylamino)butyl carbonate hydrochloride (1.27 g) obtained in Reference Example 39 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.26 g), triethylamine (0.95 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (1.08 g) as a yellow amorphous solid.

$^1$H-NMR(CDCl$_3$): 1.31(3H,t,J=7.2 Hz), 1.73-1.91(4H,m), 2.23(3H,s) 3.01(3H,bs), 3.50-3.62(2H,m), 4.15-4.22(4H,m), 4.38(2H,q,J=7.8 Hz), 4.87-5.13(2H,m), 6.64(1H,d,J=5.4 Hz), 7.35-7.46(3H,m), 7.83(1H,d,J=7.8 Hz), 8.35(1H,d, J=5.4 Hz).

102
Example 42

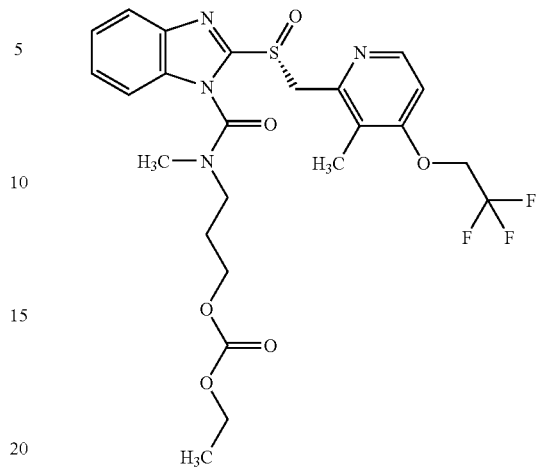

Ethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl carbonate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., ethyl 3-(methylamino)propyl carbonate hydrochloride (1.18 g) obtained in Reference Example 44 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.10 g), triethylamine (0.83 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (0.88 g) as a yellow amorphous solid.

$^1$H-NMR(CDCl$_3$): 1.29(3H,t,J=7.2 Hz), 2.10-2.20(2H,m), 2.22(3H,s), 3.02(3H,bs), 3.55-3.77(2H,m), 4.14-4.30(4H,m), 4.37(2H,q,J=7.8 Hz), 4.83-5.13(2H,m), 6.64(1H,d,J=5.6 Hz), 7.35-7.46(3H,m), 7.82(1H,d,J=8.1 Hz), 8.35(1H,d, J=5.6 Hz).

Example 43

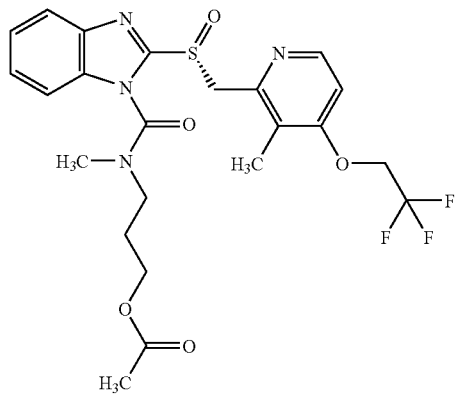

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propyl acetate To a solution (40 mL) of bis(trichloromethyl)carbonate (1.19 g) in tetrahydrofuran was dropwise added a solution (2 mL) of pyridine (0.95 mL) in tetrahydrofuran under ice-cooling. After stirring under ice-cooling for 30 min., 3-(methylamino)propyl acetate hydrochloride (1.90 g) obtained in Reference Example 42 was added. A solution (2 mL) of triethylamine (1.68 mL) in tetrahydrofuran was dropwise added, and the mixture was stirred at room temperature for 3 hrs. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was dissolved in tetrahydrofuran (40 mL). (R)-2-[[[3-Methyl-4-(2,2,2-trifluoroethoxy)-2-pyridyl]methyl]sulfinyl]-1H-benzimidazole (1.99 g), triethylamine (1.50 mL) and 4-dimethylaminopyridine (catalytic amount) were added, and the mixture was stirred at 60° C. overnight. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was purified by basic silica gel column chromatography (eluted with ethyl acetate:hexane-1:2, then 1:1) to give the title compound (1.22 g) as a yellow amorphous solid.

$^1$H-NMR(CDCl$_3$): 1.97(3H,s), 2.05-2.15(2H,m), 2.22(3H,s), 3.03(3H,bs), 3.42-3.72(2H,m), 4.10-4.22(2H,m), 4.37(2H,q,J=7.8 Hz), 4.85-5.13(2H,m), 6.64(1H,d,J=5.6 Hz), 7.24-7.44(3H,m), 7.83(1H,d,J=7.5 Hz), 8.35(1H,d,J=5.6 Hz).

Example 44

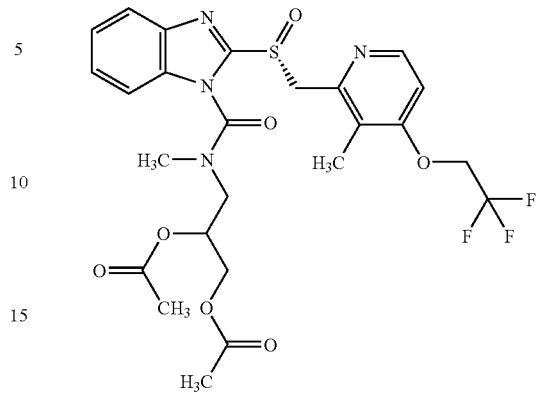

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl diacetate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., 3-(methylamino)propane-1,2-diyl diacetate hydrochloride (1.35 g) obtained in Reference Example 46 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.27 g), triethylamine (0.96 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (0.50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (0.64 g) as a yellow amorphous solid.

$^1$H-NMR(CDCl$_3$): 2.05(3H,s), 2.13(3H,s), 2.23(3H,s), 3.07(3H,bs), 3.42-3.95(2H,m), 4.06-4.43(2H,m), 4.38(2H,q, J=7.8 Hz), 4.85-5.05(2H,m), 5.42-5.50(1H,m), 6.63-6.66(1H,m), 7.38-7.51(3H,m), 7.78-7.85(1H,m), 8.33-8.36(1H, m).

Example 45

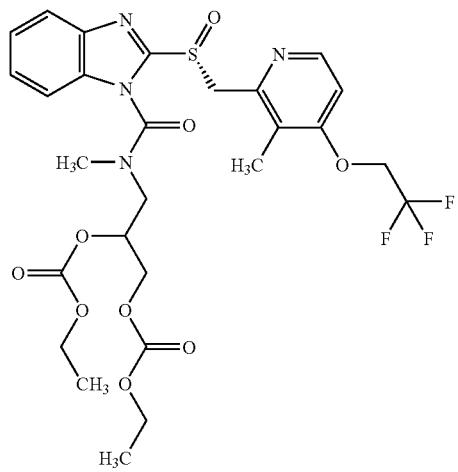

Diethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl biscarbonate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., diethyl 3-(methylamino)propane-1,2-diyl biscarbonate hydrochloride (1.71 g) obtained in Reference Example 47 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.53 g), triethylamine (1.16 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (1.42 g) as a yellow amorphous solid.

$^1$H-NMR(CDCl$_3$): 1.28-1.34(6H,m), 2.22(3H,s), 3.07(3H,bs), 3.42-4.60(10H,m), 4.85-5.08(2H,m), 5.30-5.42(1H,m), 6.62-6.64(1H,m) 7.37-7.42(3H,m), 7.80-7.83(1H,m), 8.32-8.35(1H,m).

Example 46

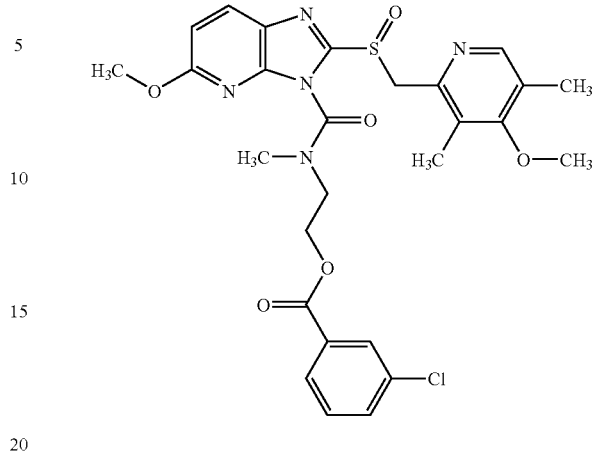

2-[[[5-Methoxy-2-[[(4-methoxy-3,5-dimethyl-2-pyridyl)methyl]sulfinyl]-3H-imidazo[4,5-b]pyridin-3-yl]carbonyl](methyl)amino]ethyl 3-chlorobenzoate To a solution (7 mL) of bis(trichloromethyl)carbonate (0.194 g) in tetrahydrofuran was dropwise added a solution (1 mL) of pyridine (0.162 mL) in tetrahydrofuran under ice-cooling. After stirring under ice-cooling for 30 min., 2-(methylamino)ethyl 3-chlorobenzoate hydrochloride (0.50 g) obtained in Reference Example 7 was added. A solution (1 mL) of triethylamine (0.279 mL) in tetrahydrofuran was dropwise added, and the mixture was stirred at room temperature for 2.5 hrs. After concentration under reduced pressure, water (15 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-imidazo[4,5-b]pyridine (0.445 g) synthesized by the method described in JP-A-63-146882, triethylamine (0.357 mL) and 4-dimethylaminopyridine (0.012 g) were added, and the mixture was stirred at 60° C. for 14 hrs. After concentration under reduced pressure, water (30 mL) was added to the residue, and the mixture was extracted with ethyl acetate (70 mL). The ethyl acetate layer was washed with saturated brine (20 mL) and dried over anhydrous magnesium sulfate. After concentration under reduced pressure, the residue was purified by basic silica gel column chromatography (eluted with ethyl acetate:hexane=1:2, then 1:1) to give the title compound (0.360 g) as a colorless amorphous solid.

$^1$H-NMR(CDCl$_3$): 2.21(3H,s), 2.23(3H,s), 3.32,3.38(total 3H,s), 3.72(3H,s), 3.81(3H,s), 3.92-4.09(2H,m), 4.50-4.73 (2H,m), 4.87(1H,d,J=13.4 Hz), 4.94(1H,d,J=13.4 Hz), 6.77 (1H,d,J=8.8 Hz), 7.36(1H,m), 7.52(1H,m), 7.80-8.03(3H,m), 8.20(1H,s).

Example 47

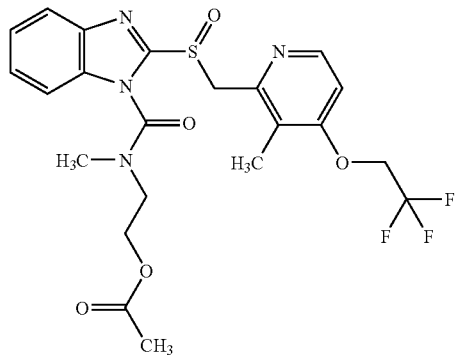

2-[Methyl[[2-[[[3-methyl-4-(2,2,2-trifluoroethoxy)-
2-pyridyl]methyl]sulfinyl]-1H-benzimidazol-1-yl]
carbonyl]amino]ethyl acetate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 1 hr., 2-(methylamino)ethyl acetate hydrochloride (0.922 g) obtained in Reference Example 2 was added. A solution (1 mL) of triethylamine (0.84 mL) in tetrahydrofuran was dropwise added, and the mixture was stirred at room temperature for 2.5 hrs. After concentration under reduced pressure, water (40 mL) was added to the residue, and the mixture was extracted with ethyl acetate (80 mL). The ethyl acetate layer was washed with saturated brine (25 mL) and dried over anhydrous magnesium sulfate. After concentration under reduced pressure, the residue was dissolved in tetrahydrofuran (15 mL). 2-[[[3-Methyl-4-(2,2,2-trifluoroethoxy)-2-pyridyl]methyl]sulfinyl]-1H-benzimidazole (1.10 g), triethylamine (0.84 mL) and 4-dimethylaminopyridine (0.036 g) were added, and the mixture was stirred at 60° C. for 4.5 hrs. After concentration under reduced pressure, water (40 mL) was added to the residue, and the mixture was extracted with ethyl acetate (80 mL). The ethyl acetate layer was washed with saturated brine (30 mL) and dried over anhydrous magnesium sulfate. After concentration under reduced pressure, the residue was purified by silica gel column chromatography (eluted with ethyl acetate:hexane=1:1, then 2:1) to give the title compound (1.18 g) as a colorless solid.

$^1$H-NMR(CDCl$_3$): 2.10(3H,s), 2.24(3H,s), 3.09(3H,bs), 3.60-4.00(2H,br), 4.25-4.50(2H,m), 4.38(2H, q,J=7.8 Hz), 4.84-5.18(2H,m), 6.64(1H,d,J=5.6 Hz), 7.36-7.48(3H,m), 7.85(1H,d,J=7.8 Hz), 8.35(1H,d,J=5.6 Hz).

Example 48

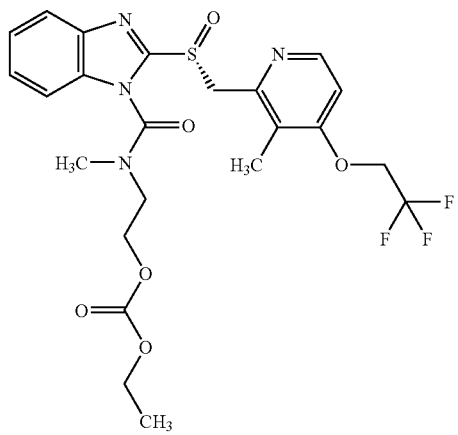

Ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate A solution of (R)-2-[[[3-methyl-4-[(2,2,2-trifluoroethoxy)-2-pyridyl]methyl]sulfinyl]-1H-benzimidazole (130 g), triethylamine (63.8 mL), 4-dimethylaminopyridine (0.86 g) and 2-[(chlorocarbonyl)(methyl)amino]ethyl ethyl carbonate (84.8 g) obtained in Reference Example 34 in tetrahydrofuran (813 mL) was stirred at 45-50° C. for 18 hrs. The reaction mixture was concentrated under reduced pressure and water (300 mL) was added to the residue, and the mixture was extracted with ethyl acetate (700 mL). The ethyl acetate layer was washed 3 times with saturated brine (300 mL), and anhydrous magnesium sulfate (130 g) and activated carbon (13 g) were added. The mixture was stirred at room temperature for 30 min. and filtrated. The filtrate was concentrated under reduced pressure and the residue was dissolved in diethyl ether (600 mL) containing triethylamine (0.49 mL), and the mixture was concentrated under reduced pressure. This step was further repeated twice. The obtained oily substance was dissolved in ethanol (200 mL) containing triethylamine (2.45 mL) and water (120 mL) was dropwise added under ice-cooling. The precipitated crystals were collected by filtration, washed 3 times with ice-cooled ethanol-water (volume ratio 1:1, 150 mL) and dried to give the title compound (172.2 g) as a colorless solid. LH-NMR(CDCl$_3$) showed the same chart as with the compound obtained in Example 14.

Example 49

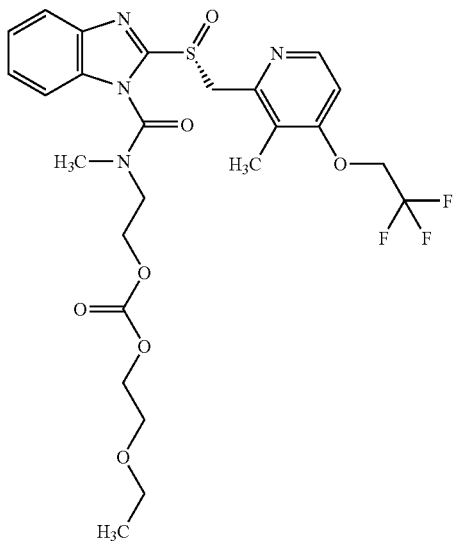

2-Ethoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.43 g) in tetrahydrofuran was dropwise added a solution (1 mL) of pyridine (0.35 mL) in tetrahydrofuran under ice-cooling. After stirring under ice-cooling for 10 min., 2-ethoxyethyl 2-(methylamino)ethyl carbonate hydrochloride (0.82 g) obtained in Reference Example 48 was added. A solution (1 mL) of triethylamine (0.60 mL) in tetrahydrofuran was dropwise added, and the mixture was stirred at room temperature for 3 days. After concentration under reduced pressure, water (50 mL) was added to the residue and the mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 6 hrs. and at room temperature for 11 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate:hexane=7:3) to give the title compound (1.39 g) as a yellow amorphous solid.

$^1$H-NMR(CDCl$_3$): 1.19(3H,t,J=6.9 Hz), 2.23(3H,s), 3.09 (3H,bs), 3.40-4.20(2H,br), 3.53(2H,q,J=6.9 Hz), 3.63-3.69 (2H,m), 4.27-4.34(2H,m), 4.39(2H,q,J=7.8 Hz), 4.47(2H,m), 4.80-5.20(2H,m), 6.65(1H,d,J=5.6 Hz), 7.30-7.52(3H,m), 7.84(1H,d,J=7.5 Hz), 8.35(1H,d,J=5.6 Hz).

Example 50

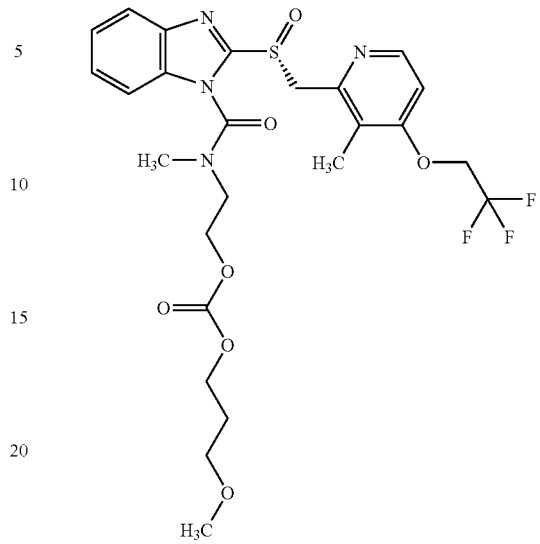

3-Methoxypropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.53 g) in tetrahydrofuran was dropwise added a solution (1 mL) of pyridine (0.44 mL) in tetrahydrofuran under ice-cooling. After stirring under ice-cooling for 5 min., 3-methoxypropyl 2-(methylamino)ethyl carbonate hydrochloride (0.82 g) obtained in Reference Example 49 was added. A solution (1 mL) of triethylamine (0.75 mL) in tetrahydrofuran was dropwise added and the mixture was stirred at room temperature for 1 hr. After concentration under reduced pressure, water (50 mL) was added to the residue and the mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 6 hrs. and at room temperature for 6 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate:hexane=7:3). Crystallization from diethyl ether gave the title compound (0.70 g) as a colorless solid.

$^1$H-NMR(CDCl$_3$): 1.94(2H,quintet,J=6.2 Hz), 2.23(3H,s), 3.09(3H,bs), 3.31(3H,s), 3.40-4.20(2H,br), 3.44(2H,t,J=6.2 Hz), 4.25(2H,t,J=6.5 Hz), 4.38(2H,q,J=7.8 Hz), 4.44(2H,m), 4.80-5.20(2H,m), 6.64(1H,d,J=5.6 Hz), 7.35-7.48(3H,m), 7.83(1H,d,J=7.8 Hz), 8.34(1H,d,J=5.6 Hz).

Example 51

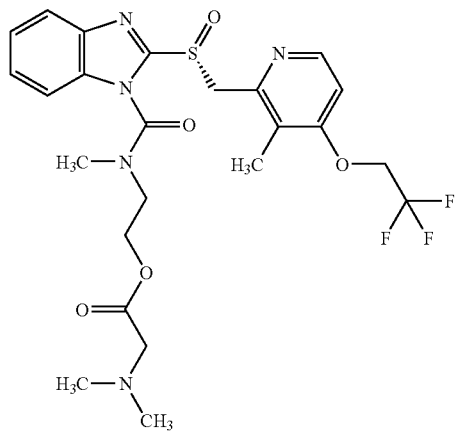

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl N,N-dimethylglycinate 2-(Methylamino)ethyl N,N-dimethylglycinate dihydrochloride (1.06 g) obtained in Reference Example 50 was added to tetrahydrofuran (40 mL) and the mixture was stirred for a while, to which bis(trichloromethyl)carbonate (0.77 g) was added. After ice-cooling, a solution (5 mL) of triethylamine (2.17 mL) in tetrahydrofuran was dropwise added and the mixture was stirred at room temperature for 3 hrs. The precipitated solid was filtered off and ethyl acetate (80 mL) was added. The mixture was washed with an ice-cooled aqueous sodium hydrogen carbonate solution (50 mL) and saturated brine (50 mL×2) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 6 hrs. and at room temperature for 3 days. 4-Dimethylaminopyridine (0.037 g) was added, and the mixture was further stirred at 60° C. for 6 hrs. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate, then methanol:ethyl acetate=1:19). Crystallization from diethyl ether gave the title compound (0.41 g) as a colorless solid.

$^1$H-NMR(CDCl$_3$): 2.23(3H,s), 2.35(6H,s), 3.08(3H,bs), 3.21(2H,s), 3.50-4.20(2H,br), 4.38(2H,q,J=7.8 Hz), 4.44(2H,m), 4.80-5.18(2H,m), 6.64(1H,d,J=5.6 Hz), 7.36-7.48(3H,m), 7.84(1H,d,J=6.9 Hz), 8.35(1H,d,J=5.6 Hz).

Example 52

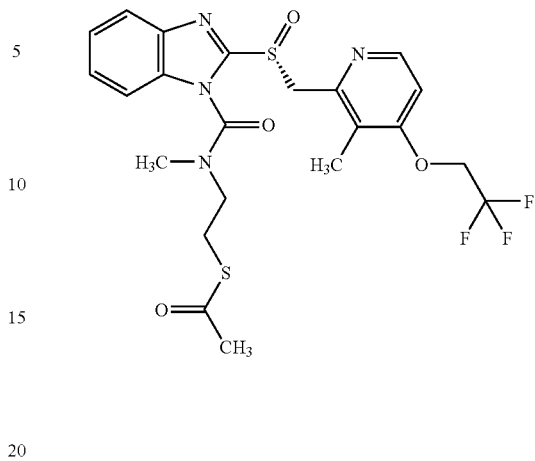

S-[2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl]thioacetate S-[2-(Methylamino)ethyl]thioacetate hydrochloride (0.75 g) obtained in Reference Example 51 was added to tetrahydrofuran (30 mL) and the mixture was stirred for a while, to which bis(trichloromethyl)carbonate (0.66 g) was added. After ice-cooling, a solution (10 mL) of triethylamine (1.85 mL) in tetrahydrofuran was dropwise added and the mixture was stirred under ice-cooling for 30 min. and at room temperature for 30 min. The precipitated solid was filtered off and ethyl acetate (50 mL) was added to the filtrate. The mixture was washed with ice-cooled 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (0.96 g), triethylamine (0.54 mL) and 4-dimethylaminopyridine (0.032 g) were added, and the mixture was stirred at 60° C. for 6 hrs. and at room temperature for 8 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by silica gel column chromatography (eluted with acetone:hexane=3:7, then acetone:hexane=7:3) to give the title compound (1.19 g) as a yellow amorphous solid.

$^1$H-NMR(CDCl$_3$): 2.23(3H,s), 2.34(3H,s), 3.10(3H,bs), 3.22(2H,t,J=6.6 Hz), 3.67(2H,m), 4.38(2H,q,J=7.8 Hz), 4.80-5.20(2H,m), 6.64(1H,d,J=5.7 Hz), 7.35-7.50(3H,m), 7.83(1H,d,J=6.9 Hz), 8.35(1H,d,J=5.7 Hz).

Example 53

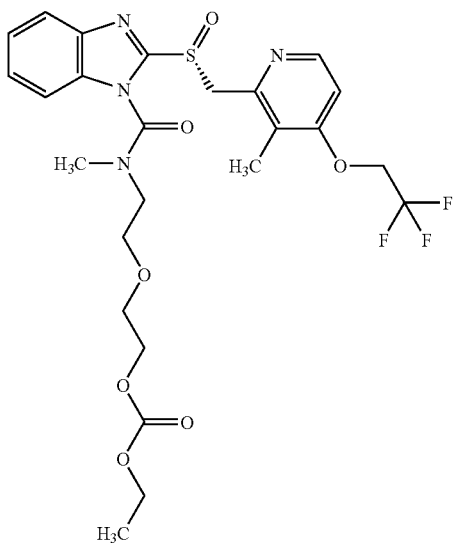

Ethyl 2-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]ethyl carbonate To a solution (40 mL) of bis(trichloromethyl)carbonate (1.19 g) in tetrahydrofuran was dropwise added a solution (2 mL) of pyridine (0.95 mL) in tetrahydrofuran under ice-cooling. After stirring under ice-cooling for 30 min., ethyl 2-[2-(methylamino)ethoxy]ethyl carbonate hydrochloride (2.73 g) obtained in Reference Example 52 was added. A solution (2 mL) of triethylamine (1.68 mL) in tetrahydrofuran was dropwise added, and the mixture was stirred at room temperature for 3 hrs. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was dissolved in tetrahydrofuran (40 mL). (R)-2-[[[3-Methyl-4-(2,2,2-trifluoroethoxy)-2-pyridyl]methyl]sulfinyl]-1H-benzimidazole (2.80 g), triethylamine (2.11 mL) and 4-dimethylaminopyridine (catalytic amount) were added, and the mixture was stirred at 60° C. overnight. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was purified by basic silica gel column chromatography (eluted with ethyl acetate:hexane=1:2, then 1:1) to give the title compound (2.19 g) as a yellow amorphous solid.

$^1$H-NMR(CDCl$_3$): 1.28(3H,t,J=7.2 Hz), 2.24(3H,s), 3.10 (3H,bs), 3.38-3.80(6H,m), 4.18(2H,q,J=7.2 Hz), 4.27-4.34 (2H,m), 4.38(2H,q,J=8.4 Hz), 4.83-5.30(2H,m), 6.65(1H,d, J=5.7 Hz), 7.35-7.50(3H,m), 7.84(1H,d,J=7.8 Hz), 8.36(1H, d,J=5.7 Hz).

Example 54

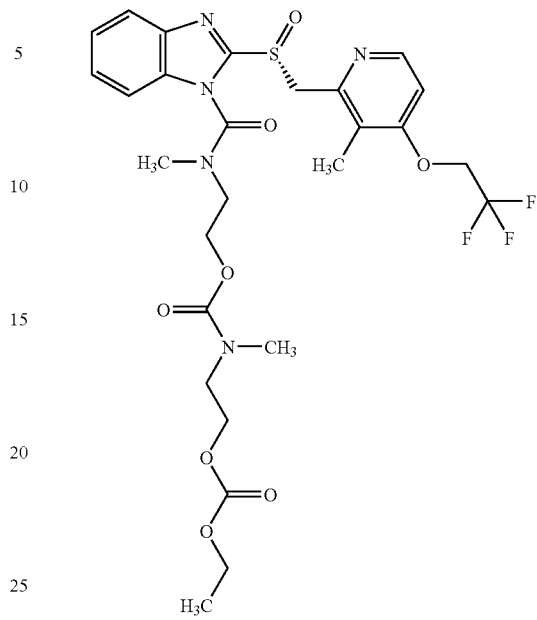

Ethyl 2-[methyl[[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]carbonyl]amino]ethyl carbonate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., ethyl 2-[methyl[[2-(methylamino)ethoxy]carbonyl]amino]ethyl carbonate hydrochloride (1.71 g) obtained in Reference Example 53 was added. A solution (1 mL) of triethylamine (0.84 mL) in tetrahydrofuran was dropwise added and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.59 g), triethylamine (1.20 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (1.62 g) as a yellow amorphous solid.

$^1$H-NMR(CDCl$_3$): 1.24-1.31(3H,m), 2.24(3H,bs), 2.97-2.99(3H,m), 3.10(3H,bs), 3.55-3.58(2H,m), 4.09-4.50(10H, m), 4.88-5.08(2H,m), 6.65(1H,t,J=5.7 Hz), 7.36-7.48(3H,m), 7.85(1H,d,J=6.9 Hz), 8.36(1H,d,J=5.7 Hz).

Example 55

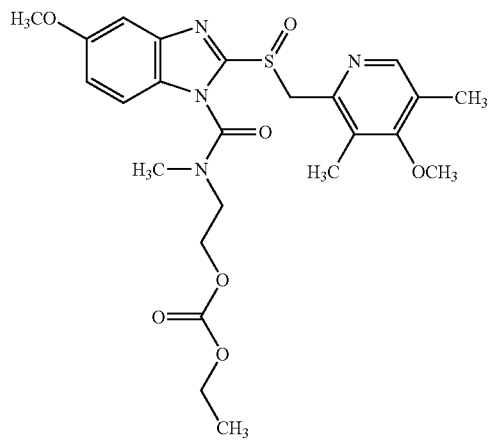

Ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 1 hr., ethyl 2-(methylamino)ethyl carbonate hydrochloride (0.551 g) obtained in Reference Example 14 was added. A solution (1 mL) of triethylamine (0.418 mL) in tetrahydrofuran was dropwise added, and the mixture was stirred at room temperature for 2 hrs. After concentration under reduced pressure, water (15 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-benzimidazole (0.817 g), triethylamine (0.661 mL) and 4-dimethylaminopyridine (0.012 g) were added, and the mixture was stirred at 60° C. for 12 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2, then 1:1) to give a 3:2 mixture (0.92 g) of the title compound and ethyl 2-[[[6-methoxy-2-[[(4-methoxy-3,5-dimethyl-2-pyridyl)methyl]sulfinyl]-1H-benzimidazol-1-yl]carbonyl](methyl)amino]ethyl carbonate as a pale-yellow amorphous solid.

$^1$H-NMR(CDCl$_3$): 1.27-1.34(3H,m), 2.10-2.30(3H,m), 2.23(3H,s), 2.99-3.23(3H,m), 3.40-3.85(2H,m), 3.69(6/5H, s), 3.71(9/5H,s), 3.86(6/5H,s), 3.88(9/5H,s), 4.14-4.25(2H, m), 4.38-4.60(2H,m), 4.82-5.06(2H,m), 6.92-7.08(7/5H,m), 7.33(3/5H,d,J=9.0 Hz), 7.66(1H,m), 8.21(1H,s).

Example 56

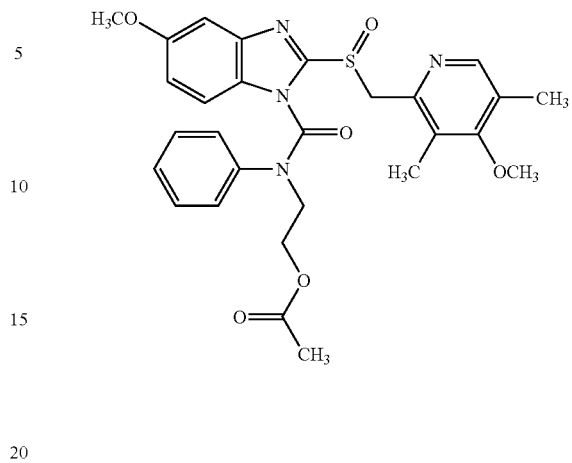

2-[[[5-Methoxy 2-[[(4-methoxy-3,5-dimethyl-2-pyridyl)methyl]sulfinyl]-1H-benzimidazol-1-yl]carbonyl](phenyl)amino]ethyl acetate To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., 2-anilinoethyl acetate hydrochloride (0.647 g) obtained in Reference Example 27 was added. A solution (1 mL) of triethylamine (0.419 mL) in tetrahydrofuran was dropwise added, and the mixture was stirred at room temperature for 3 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-benzimidazole (0.829 g), triethylamine (0.669 mL) and 4-dimethylaminopyridine (0.012 g) were added, and the mixture was stirred at 60° C. for 14 hrs. After concentration under reduced pressure, water (40 mL) was added to the residue, and the mixture was extracted with ethyl acetate (80 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2) to give a 1:1 mixture (1.10 g) of the title compound and 2-[[[6-methoxy-2-[[(4-methoxy-3,5-dimethyl-2-pyridyl)methyl]sulfinyl]-1H-benzimidazol-1-yl]carbonyl](phenyl)amino]ethyl acetate as a colorless amorphous solid.

$^1$H-NMR(CDCl$_3$): 1.99(3H,s), 2.19(1.5H.s), 2.21(1.5H,s), 2.25(3H,s), 3.70(1.5H,s), 3.71(3H,s), 3.78(1.5H,s), 3.84(1.5H,s), 4.15-4.56(4H,m), 4.74-4.80(1H,m), 4.91-4.98 (1H,m), 6.83-6.91(1.5H,m), 7.04-7.19(3.5H,m), 7.25-7.53 (2.5H,m), 7.51(0.5H,d,J=8.7 Hz), 8.25(1H,s).

Example 57

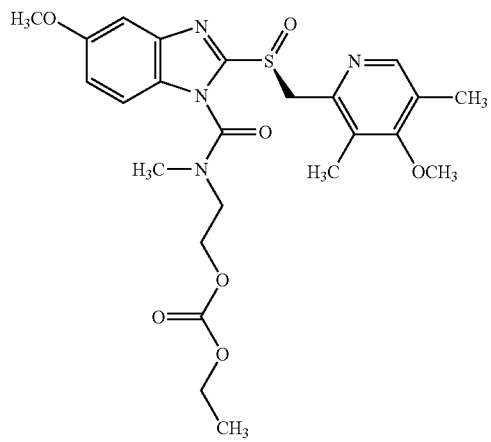

Ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate To a solution (10 mL) of (S)-5-methoxy-2-[[(4-methoxy-3,5-dimethyl-2-pyridyl)methyl]sulfinyl]-1H-benzimidazole (1.34 g) synthesized by the method described in Example 1 of Japanese Patent Application under PCT laid-open under kohyo No. 10-504290 in tetrahydrofuran were added 2-[(chlorocarbonyl)(methyl)amino]ethyl ethyl carbonate (0.9 mL) obtained in Reference Example 34, triethylamine (1.08 mL) and 4-dimethylaminopyridine (0.010 g), and the mixture was stirred at 60° C. for 6 hrs. After concentration under reduced pressure, water (30 mL) was added to the residue and the mixture was extracted with ethyl acetate (50 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2, then 1:1) to give a 3:2 mixture (0.92 g) of the title compound and ethyl 2-[[[(S)-6-methoxy-2-[[(4-methoxy-3,5-dimethyl-2-pyridyl)methyl]sulfinyl]-1H-benzimidazol-1-yl]carbonyl](methyl)amino]ethyl carbonate as a pale-yellow amorphous solid.

H-NMR(CDCl$_3$): 1.25-1.34(3H,m), 2.10-2.30(3H,m), 2.23(3H,s), 2.99-3.23(3H,m), 3.40-3.85(2H,m), 3.69(6/5H,s), 3.71(9/5H,s), 3.86(6/5H,s), 3.88(9/5H,s), 4.14-4.25(2H,m), 4.38-4.60(2H,m), 4.79-5.05(2H,m), 6.92-7.08(7/5H,m), 7.33(3/5H,d,J=9.3 Hz), 7.65(1H,m), 8.21(1H,s).

Example 58

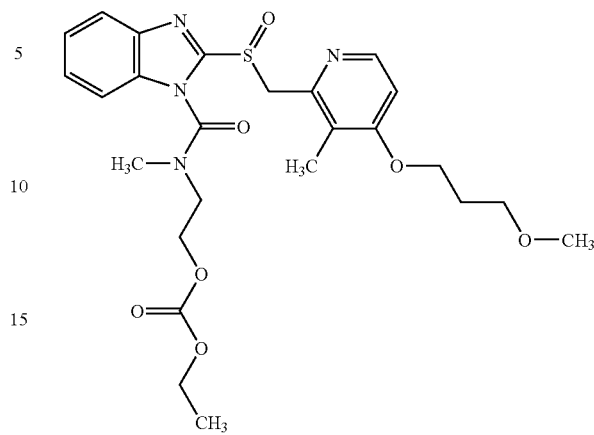

Ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., ethyl 2-(methylamino)ethyl carbonate-hydrochloride (0.551 g) obtained in Reference Example 14 was added. A solution (1 mL) of triethylamine (0.418 mL) in tetrahydrofuran was dropwise added, and the mixture was stirred at room temperature for 2.5 hrs. After concentration under reduced pressure, water (15 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 2-[[[4-(3-Methoxypropoxy)-3-methyl-2-pyridyl]methyl]sulfinyl]-1H-benzimidazole (0.723 g), triethylamine (0.528 mL) and 4-dimethylaminopyridine (0.012 g) were added, and the mixture was stirred at 60° C. for 17 hrs. After concentration under reduced pressure, water (40 mL) was added to the residue, and the mixture was extracted with ethyl acetate (80 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2), then by silica gel column chromatography (eluted with ethyl acetate:hexane=1:1, then ethyl acetate) to give the title compound (0.44 g) as a colorless amorphous solid.

$^1$H-NMR(CDCl$_3$): 1.31(3H,t,J=7.1 Hz), 2.05(2H,m), 2.18(3H,s), 3.08(3H,bs), 3.34(3H,s), 3.54(2H,t,J=6.1 Hz), 3.61-4.01(2H,m), 4.08(2H,t,J=6.3 Hz), 4.21(2H,t,J=7.1 Hz), 4.38-4.54(2H,m), 4.81-5.12(2H,m), 6.68(1H,d,J=5.6 Hz), 7.34-7.48(3H,m), 7.83(1H,d,J=7.8 Hz), 8.27(1H,d,J=5.6 Hz).

Example 59

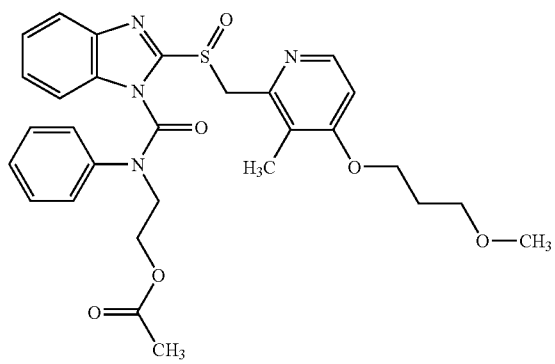

2-[[[2-[[[4-(3-Methoxypropoxy)-3-methyl-2-pyridyl]methyl]sulfinyl]-1H-benzimidazol-1-yl]carbonyl](phenyl)amino]ethyl acetate To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., 2-anilinoethyl acetate hydrochloride (0.647 g) obtained in Reference Example 27 was added. A solution (1 mL) of triethylamine (0.419 mL) in tetrahydrofuran was dropwise added, and the mixture was stirred at room temperature for 3 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 2-[[[4-(3-Methoxypropoxy)-3-methyl-2-pyridyl]methyl]sulfinyl]-1H-benzimidazole (0.877 g), triethylamine (0.641 mL) and 4-dimethylaminopyridine (0.012 g) were added, and the mixture was stirred at 60° C. for 16 hrs. After concentration under reduced pressure, water (40 mL) was added to the residue, and the mixture was extracted with ethyl acetate (80 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2), then by silica gel column chromatography (eluted with ethyl acetate) to give the title compound (0.93 g) as a colorless amorphous solid.

$^1$H-NMR(CDCl$_3$): 1.99(3H,s), 2.07(3H,s), 2.19(3H,s), 3.35(3H,s), 3.54(2H,t,J=6.2 Hz), 4.09(2H,t,J=6.2 Hz), 4.14-4.40(4H,m), 4.80(1H,d,J=13.7 Hz), 5.00(1H,d,J=13.7 Hz), 6.71(1H,d,J=5.7 Hz), 7.03-7.34(7H,m), 7.38(1H,m), 7.65(1H,m), 8.32(1H,d,J=5.7 Hz).

Example 60

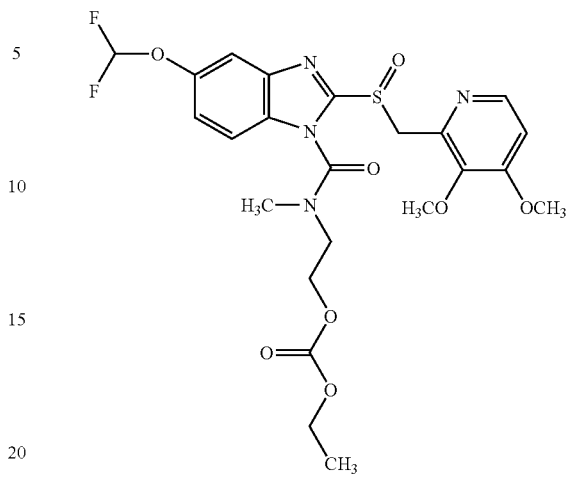

2-[[[5-(Difluoromethoxy)-2-[[(3,4-dimethoxy-2-pyridyl)methyl]sulfinyl]-1H-benzimidazol-1-yl]carbonyl](methyl)amino]ethyl ethyl carbonate To a solution (8 mL) of bis(trichloromethyl)carbonate (0.174 g) in tetrahydrofuran was dropwise added a solution (1 mL) of pyridine (0.146 mL) in tetrahydrofuran under ice-cooling. After stirring under ice-cooling for 1 hr., ethyl 2-(methylamino)ethyl carbonate hydrochloride (0.330 g) obtained in Reference Example 14 was added. A solution (1 mL) of triethylamine (0.250 mL) in tetrahydrofuran was dropwise added, and the mixture was stirred at room temperature for 3 hrs. After concentration under reduced pressure, water (10 mL) was added to the residue, and the mixture was extracted with ethyl acetate (30 mL). The ethyl acetate layer was washed with saturated brine (10 mL) and dried over anhydrous magnesium sulfate. After concentration under reduced pressure, the residue was dissolved in tetrahydrofuran (8 mL). 5-(Difluoromethoxy)-2-[[(3,4-dimethoxy-2-pyridyl)methyl]sulfinyl]-1H-benzimidazole (0.432 g), triethylamine (0.279 mL) and 4-dimethylaminopyridine (0.008 g) were added, and the mixture was stirred at 60° C. for 17.5 hrs. After concentration under reduced pressure, water (20 mL) was added to the residue, and the mixture was extracted with ethyl acetate (50 mL). The ethyl acetate layer was washed with saturated brine (10 mL) and dried over anhydrous magnesium sulfate. After concentration under reduced pressure, the residue was purified by basic silica gel column chromatography (eluted with ethyl acetate:hexane=1:2, then 1:1), then by silica gel column chromatography (eluted with ethyl acetate:hexane=2:1, then ethyl acetate) to give a 1:1 mixture (0.09 g) of the title compound and 2-[[[6-(difluoromethoxy)-2-[[(3,4-dimethoxy-2-pyridyl)methyl]sulfinyl]-1H-benzimidazol-1-yl]carbonyl]methylamino]ethyl ethyl carbonate as a pale-yellow amorphous solid.

$^1$H-NMR(CDCl$_3$): 1.31(3H,t,J=7.2 Hz), 3.06(3H,s), 3.42-3.98(2H,m), 3.87(3H,s), 3.90(3H,s), 4.21(2H,q,J=7.2 Hz), 4.36-4.54(2H,m), 4.90(1H,d,J=13.2 Hz), 4.98(1H,d,J=13.2 Hz), 6.54(0.5H,t,J=73.5 Hz), 6.61(0.5H,t,J=73.5 Hz), 6.78(1H,d,J=5.3 Hz), 7.15-7.25(1.5H,m), 7.44(0.5H,d,J=9.0 Hz), 7.59(0.5H,s), 7.80(0.5H,d,J=9.0 Hz), 8.17(1H,d,J=5.3 Hz).

Example 61

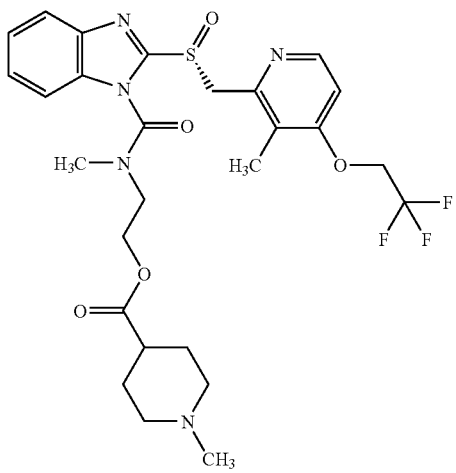

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methylpiperidine-4-carboxylate 2-(Methylamino)ethyl 1-methylpiperidine-4-carboxylate dihydrochloride (0.98 g) obtained in Reference Example 54 was added to tetrahydrofuran (50 mL) and the mixture was stirred for a while, to which bis(trichloromethyl)carbonate (0.53 g) was added. After ice-cooling, a solution (50 mL) of triethylamine (2.01 mL) in tetrahydrofuran was dropwise added and the mixture was stirred at room temperature for 3 hrs. Ethyl acetate (100 mL) was added and the mixture was washed with an aqueous sodium hydrogen carbonate solution (100 mL) and saturated brine (80 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (0.74 g), triethylamine (0.56 mL) and 4-dimethylaminopyridine (0.049 g) were added, and the mixture was stirred at 60° C. overnight. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=7:3, then ethyl acetate, then methanol:ethyl acetate=1:19) to give the title compound (0.78 g) as a yellow-green amorphous solid.

$^1$H-NMR(CDCl$_3$): 1.65-2.05(6H,m), 2.23(3H,s), 2.25(3H,s), 2.24-2.38(1H,m), 2.75-2.85(2H,m), 3.07(3H,bs), 3.40-4.10(2H,br), 4.38(2H,q,J=7.8 Hz), 4.40(2H,m), 4.80-5.10(2H,br), 6.64(1H,d,J=5.6 Hz), 7.36-7.47(3H,m), 7.84(1H,d, J=7.8 Hz), 8.35(1H,d,J=5.6 Hz).

Example 62

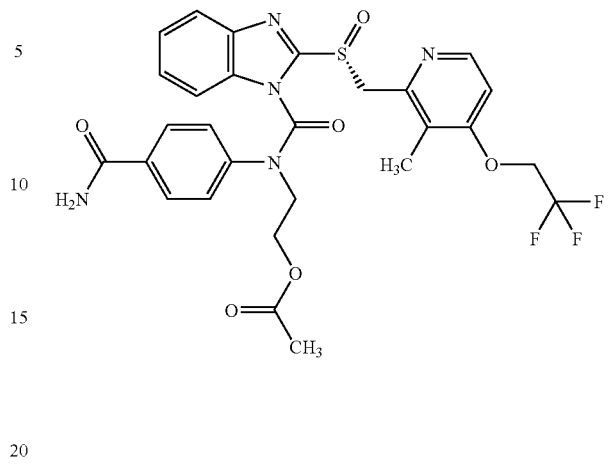

2-[[4-(Aminocarbonyl)phenyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (20 mL) of bis(trichloromethyl)carbonate 0.45 g) in tetrahydrofuran was dropwise added a solution (10 mL) of 2-[[4-(aminocarbonyl)phenyl]amino]ethyl acetate (0.67 g) obtained in Reference Example 55 and triethylamine (0.63 mL) in tetrahydrofuran under ice-cooling, and the mixture was stirred at room temperature for 1 hr. After concentration under reduced pressure, water (50 mL) was added to the residue and the mixture was extracted with ethyl acetate (50 mL). The ethyl acetate layer was washed with 0.2N hydrochloric acid (20 mL) and saturated brine (50 mL) and dried over anhydrous magnesium sulfate. After concentration under reduced pressure, the residue was dissolved in tetrahydrofuran (30 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 30 min. and at room temperature overnight. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=4:6, then 6:4, then 8:2) to give the title compound (1.26 g) as a yellow amorphous solid.

$^1$H-NMR(CDCl$_3$): 1.99 (3H,s), 2.26 (3H,s), 4.15-4.55 (4H, m), 4.41(2H,q,J=7.9 Hz), 4.80-5.20(2H,br), 6.69(1H,d,J=5.7 Hz), 7.26-7.38(3H,m), 7.48(2H,d,J=8.9 Hz), 7.54(2H,d, J=8.9 Hz), 7.66-7.73(1H,m), 8.39(1H,d,J=5.7 Hz).

Example 63

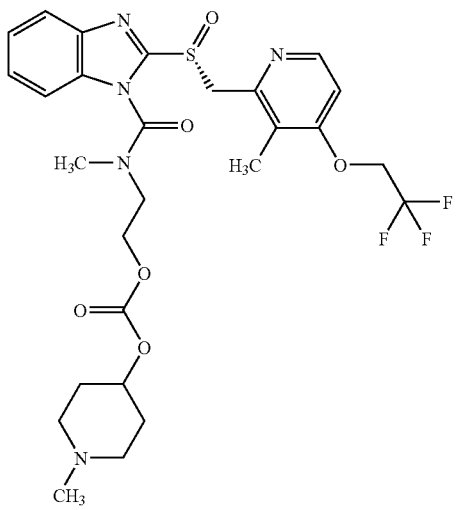

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methyl-4-piperidinyl carbonate 2-(Methylamino)ethyl 1-methyl-4-piperidinyl carbonate dihydrochloride (1.01 g) obtained in Reference Example 56 was added to tetrahydrofuran (30 mL) and, after stirring for a while, ice-cooled. Bis(trichloromethyl)carbonate (0.69 g) was added and a solution (10 mL) of triethylamine (1.95 mL) in tetrahydrofuran was dropwise added. After stirring under ice-cooling for 1 hr. and at room temperature for 1 hr., the precipitated solid was filtered off. After concentration under reduced pressure, ethyl acetate (50 mL) was added, and the mixture was washed with an ice-cooled aqueous sodium hydrogen carbonate solution (50 mL) and saturated brine (50 mL), and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. overnight. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate, then methanol:ethyl acetate=1:19) to give the title compound (0.70 g) as a yellow amorphous solid.

$^1$H-NMR(CDCl$_3$): 1.70-1.86(2H,m), 1.90-2.04(2H,m), 2.23(3H,s), 2.28(3H,s), 2.10-2.35(2H,m), 2.60-2.72(2H,m), 3.08(3H,bs), 3.40-4.20(2H,br), 4.39(2H,q,J=7.9 Hz), 4.44(2H,m), 4.60-4.74(1H,m), 4.80-5.15(2H,br), 6.65(1H,d,J=5.9 Hz), 7.35-7.52(3H,m), 7.84(1H,d,J=7.5 Hz), 8.35(1H,d,J=5.9 Hz).

Example 64

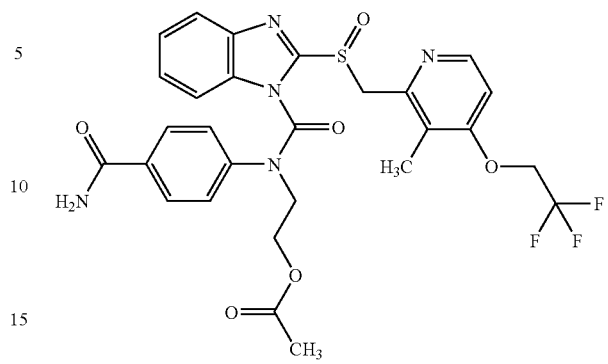

2-[[4-(Aminocarbonyl)phenyl][[2-[[[3-methyl-4-(2,2,2-trifluoroethoxy)-2-pyridyl]methyl]sulfinyl]-1H-benzimidazol-1-yl]carbonyl]amino]ethyl acetate To a solution (5 mL) of bis(trichloromethyl)carbonate (0.12 g) in tetrahydrofuran was dropwise added a solution (5 L) of 2-[[4-(aminocarbonyl)phenyl]amino]ethyl acetate (0.22 g) obtained in Reference Example 55 and triethylamine (0.17 mL) in tetrahydrofuran under ice-cooling, and the mixture was stirred at room temperature for 30 min. Water (20 mL) was added, and the mixture was extracted with ethyl acetate (30 mL). The ethyl acetate layer was washed with saturated brine (20 mL) and dried over anhydrous magnesium sulfate. After concentration under reduced pressure, the residue was dissolved in tetrahydrofuran (10 mL). 2-[[[3-Methyl-4-(2,2,2-trifluoroethoxy)-2-pyridyl]methyl]sulfinyl]-1H-benzimidazole (0.37 g), triethylamine (0.28 mL) and 4-dimethylaminopyridine (0.012 g) were added, and the mixture was stirred at 60° C. for 1 hr. After concentration under reduced pressure, an aqueous sodium hydrogen carbonate solution (20 mL) was added to the residue, and the mixture was extracted with ethyl acetate (30 mL). The ethyl acetate layer was washed with saturated brine (20 mL) and dried over anhydrous magnesium sulfate. After concentration under reduced pressure, the residue was purified by basic silica gel column chromatography (eluted with ethyl acetate:hexane=3:7, then 5:5, then 8:2) to give the title compound (0.34 g) as a pale-yellow amorphous solid.

$^1$H-NMR(CDCl$_3$): 1.99(3H,s), 2.26(3H,s), 4.15-4.55(4H, m), 4.41(2H,q,J=7.9 Hz), 4.80-5.20(2H,br), 6.69(1H,d,J=5.9 Hz), 7.26-7.40(3H,m), 7.47(2H,d,J=8.8 Hz), 7.54(2H,d,J=8.8 Hz), 7.65-7.74(1H,m), 8.38(1H,d,J=5.9 Hz).

Example 65

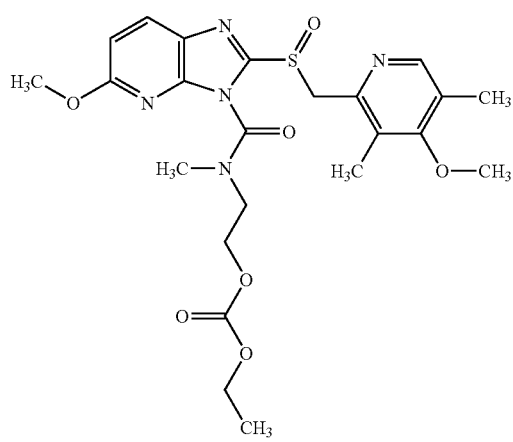

(−)-Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate 5-Methoxy-2-[[(4-methoxy-3,5-dimethyl-2-pyridyl)methyl]sulfinyl]-1H-imidazo[4,5-b]pyridine synthesized according to the method described in JP-A-63-146882 was subjected to preparative HPLC for optical resolution to give a (−) enantiomeric form (0.10 g) thereof. To a solution (5 mL) of this form in tetrahydrofuran were added 2-[(chlorocarbonyl)(methyl)amino]ethyl ethyl carbonate (0.081 g) obtained in Reference Example 34, triethylamine (0.080 mL) and 4-dimethylaminopyridine (0.007 g) and the mixture was stirred at 50° C. for 18 hrs. After concentration under reduced pressure, water (30 mL) was added to the residue and the mixture was extracted with ethyl acetate (50 mL). The ethyl acetate layer was washed with saturated brine (30 mL) and dried over anhydrous sodium sulfate. After concentration under reduced pressure, the residue was purified by basic silica gel column chromatography (eluted with ethyl acetate:hexane=2:1) to give the title compound (0.053 g) as a colorless oil.

$^1$H-NMR(CDCl$_3$): 1.30(3H,t,J=7.1 Hz), 2.24(6H,s), 3.15, 3.32(total 3H,s), 3.73(3H,s), 3.90-4.55(9H,m), 4.85(1H,d,J=13.2 Hz), 4.97(1H,d,J=13.2 Hz), 6.80(1H,d,J=8.8 Hz), 7.96(1H,d,J=8.8 Hz), 8.23(1H,s).

Example 66

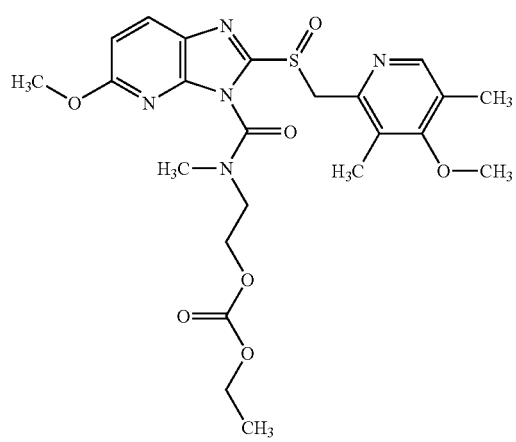

(+)-Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate 5-Methoxy-2-[[(4-methoxy-3,5-dimethyl-2-pyridyl)methyl]sulfinyl]-1H-imidazo[4,5-b]pyridine synthesized according to the method described in JP-A-63-146882 was subjected to preparative HPLC for optical resolution to give a (+) enantiomeric form (0.10 g) thereof. To a solution (5 mL) of this form in tetrahydrofuran were added 2-[(chlorocarbonyl)(methyl)amino]ethyl ethyl carbonate (0.081 g) obtained in Reference Example 34, triethylamine (0.080 mL) and 4-dimethylaminopyridine (0.007 g) and the mixture was stirred at 50° C. for 18 hrs. After concentration under reduced pressure, water (30 mL) was added to the residue and the mixture was extracted with ethyl acetate (50 mL). The ethyl acetate layer was washed with saturated brine (30 mL) and dried over anhydrous sodium sulfate. After concentration under reduced pressure, the residue was purified by basic silica gel column chromatography (eluted with ethyl acetate:hexane=2:1) to give a 2:1 mixture (0.115 g) of the title compound and (+)-ethyl 2-[[[5-methoxy-2-[[(4-methoxy-3,5-dimethyl-2-pyridyl) methyl]sulfinyl]-1H-imidazo[4,5-b]pyridin-1-yl]carbonyl](methyl)amino]ethyl carbonate as a colorless oil.

$^1$H-NMR(CDCl$_3$): 1.20-1.38(3H,m), 2.24(6H,s), 3.08, 3.15,3.33(total 3H,s), 3.73(3H,s), 3.88-4.55(9H,m), 4.78-5.05(2H,m), 6.80,6.86(1H,d,J=8.8 Hz), 7.76,7.96(1H,d,J=8.8 Hz) 8.21,8.22(total 1H,s).

Preparation Example

According to the following formulation and using a centrifugal rolling granulator, a dusting powder consisting of the remaining components was coated on sucrose•starch spherical granules while spraying a hydroxypropyl cellulose solution, thereby producing spherical granules, which spherical granules were vacuum dried and passed through a round sieve to give granules.

| composition in 300 mg of granules | (mg) |
|---|---|
| sucrose · starch spherical granules | 10.0 |
| compound of Example 1 | 30.0 |
| magnesium carbonate | 22.4 |
| purified sucrose | 59.8 |
| corn starch | 36.4 |
| low substituted hydroxypropyl cellulose | 40.0 |
| hydroxypropyl cellulose | 1.4 |
| total | 300.0 |

INDUSTRIAL APPLICABILITY

The compound of the present invention is converted to a proton pump inhibitor in living organisms to show a superior anti-ulcer activity, a gastric acid secretion inhibitory action, a mucosa-protecting action, an anti-*Helicobacter pylori* action and the like. Since it shows low toxicity, the compound is useful as a pharmaceutical product. In addition, it is stable to acid, which obviates the need to formulate an enteric-coated preparation, which in turn reduces the cost for producing an enteric preparation, and reduces the size of preparation to facilitate swallowing for patients having difficulty in swallowing, particularly for the elderly and children. Inasmuch as the compound shows faster absorption than enteric-coated preparations, a gastric acid secretion-inhibitory action is rapidly expressed, and since it is gradually converted to conventionally known proton pump inhibitor in living organisms the compound is sustainable and useful as an anti-ulcer drug and the like.

This application is based on patent application Nos. 2002-175086 and 2003-41085 filed in Japan, the contents of which are hereby incorporated by reference.

The invention claimed is:

1. An imidazole compound represented by the formula (I):

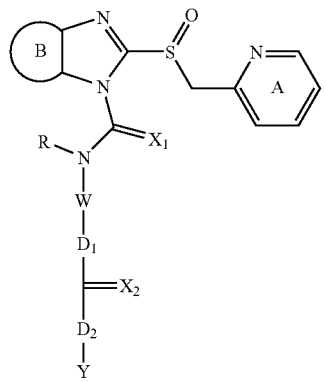

(I)

wherein
ring A is a pyridine ring optionally having substituents selected from
(1) $C_{1-6}$ alkyl group, and
(2) $C_{1-6}$ alkoxy group optionally substituted by substituent(s) selected from halogen atom(s) and $C_{1-6}$ alkoxy group, ring B is a benzene ring optionally having substituents selected from
$C_{1-6}$ alkoxy group optionally substituted by halogen atom(s), $X_1$ and $X_2$ are each an oxygen atom or a sulfur atom, W is a $C_{1-6}$ alkylene group optionally having substituents selected from $C_{1-6}$ alkyl-carbonyloxy and ethoxycarbonyloxy or a divalent group represented by the formula:

—$W_1$-Z-$W_2$— wherein $W_1$ and $W_2$ are each a $C_{1-6}$ alkylene group or a bond, Z is $C_{6-14}$ arene, an oxygen atom, $SO_n$ wherein n is 0, 1 or 2, or >N-E wherein E is a hydrogen atom, a lower alkanoyl group, a lower alkoxycarbonyl group, an aralkyloxycarbonyl group, a thiocarbamoyl group, a lower alkylsulfinyl group, a lower alkylsulfonyl group, a sulfamoyl group, a mono-lower alkylsulfamoyl group, a di-lower alkylsulfamoyl group, an arylsulfamoyl group, an arylsulfinyl group, an arylsulfonyl group, an arylcarbonyl group or a carbamoyl group, and when Z is an oxygen atom, $SO_n$ or >N-E, $W_1$ and $W_2$ are each $C_{1-6}$ alkylene group, R is a group selected from
(1) $C_{1-6}$ alkyl group optionally substituted by $C_{1-6}$ alkyl-carbonyloxy,
(2) $C_{3-10}$ cycloalkyl group, and
(3) $C_{6-14}$ aryl group optionally substituted by a group represented by —CO—$NR^2R^3$ (wherein $R^2$ and $R^3$ are each $C_{1-6}$ alkyl group), $D_1$ is an oxygen atom, a sulfur atom or >$NR_1$, $D_2$ is a bond, an oxygen atom, a sulfur atom or >$NR_1$ wherein each $R_1$ is independently $C_{1-6}$ alkyl group, and Y is a group selected from
(1) $C_{1-6}$ alkyl group optionally having substituent(s) selected from $C_{1-6}$ alkoxy group, ethoxycarbonyloxy group, $C_{6-14}$ aryl group and a group represented by —$NR^2R^3$ (wherein $R^2$ and $R^3$ are each $C_{1-6}$ alkyl group),
(2) $C_{3-10}$ cycloalkyl group,
(3) $C_{6-14}$ aryl group optionally having substituent(s) selected from (i) halogen atom and (ii) $C_{1-6}$ alkoxy group optionally having halogen atom(s), and
(4) tetrahydropyran,
or a salt thereof.

2. The compound of claim 1, wherein Z is $C_{6-14}$ arene.

3. The compound of claim 1, which is represented by the formula (II):

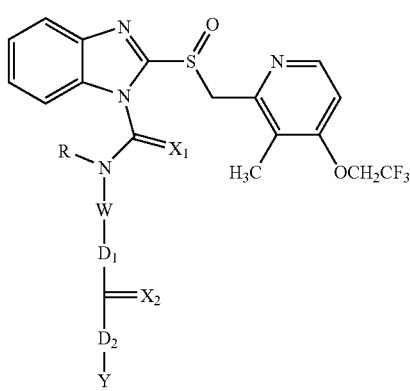

(II)

wherein each symbol in the formula is as defined in claim 1.

4. The compound of claim 1 wherein $X_1$ and $X_2$ are each an oxygen atom.

5. The compound of claim 1, wherein $D_1$ is an oxygen atom and $D_2$ is a bond or an oxygen atom.

6. The compound of claim 1, wherein W is a divalent chain $C_{1-6}$ alkylene group optionally having substituents selected from $C_{1-6}$ alkyl-carbonyloxy and ethoxycarbonyloxy.

7. The compound of claim 1, wherein W is an ethylene group.

8. The compound of claim 1, wherein Y is a group selected from
(1) $C_{1-6}$ alkyl group optionally having substituent(s) selected from $C_{1-6}$ alkoxy group, ethoxycarbonyloxy group, $C_{6-14}$ aryl group and a group represented by —$NR^2R^3$ (wherein $R^2$ and $R^3$ are each $C_{1-6}$ alkyl group),
(2) $C_{3-10}$ cycloalkyl group, and
(3) $C_{6-14}$ aryl group optionally having substituent(s) selected from (i) halogen atom and (ii) $C_{1-6}$ alkoxy group optionally having halogen atom(s).

9. The compound of claim 1, wherein $X_1$ and $X_2$ are each an oxygen atom, $D_1$ is an oxygen atom and $D_2$ is a bond or an oxygen atom, W is an ethylene group, R is a $C_{1-6}$ alkyl group, and Y is a group selected from (1) $C_{1-6}$ alkyl group optionally having substituent(s) selected from $C_{1-6}$ alkoxy group, ethoxycarbonyloxy group, $C_{6-14}$ aryl group and a group represented by —$NR^2R^3$ (wherein $R^2$ and $R^3$ are each $C_{1-6}$ alkyl group), (2) $C_{3-10}$ cycloalkyl group, and (3) $C_{6-14}$ aryl group optionally having substituent(s) selected from (i) halogen atom and (ii) $C_{1-6}$ alkoxy group optionally having halogen atom(s).

10. The compound of claim 1, which is a compound selected from 2-[methyl[[(R)-2-[[[3-methyl-4-(2,2,2-trifluoroethoxy)-2-pyridyl]methyl]sulfinyl]-1H-benzimida zol-1-yl]carbonyl]amino]ethyl acetate, ethyl 2-[methyl[[(R)-2-[[[3-methyl-4-(2,2,2-trifluoroethoxy)-2-pyridyl]methyl] sulfinyl]-1H-benzimidazol-1-yl]carbonyl]amino]ethyl carbonate, 2-[methyl[[(R)-2-[[[3-methyl-4-(2,2,2-trifluoroethoxy)-2-pyridyl]methyl]sulfinyl]-1H-benzimida zol-1yl] carbonyl]amino]ethyl tetrahydropyran-4-yl carbonate, 2-[methyl[[2-[[[3-methyl-4-(2,2,2-trifluoroethoxy)-2-pyridyl]methyl]sulfinyl]-1 H-benzimidazol-1-yl]carbonyl] amino]ethyl tetrahydropyran-4-yl carbonate, ethyl 2-[methyl [[2-[[[3-methyl-4-(2,2,2-trifluoroethoxy)-2-pyridyl]methyl] sulfinyl]-1H-benzimi dazol-1-yl]carbonyl]amino]ethyl carbonate, ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate, 2-[[[5-methoxy-2-[[(4-methoxy-3,5-dimethyl-2-pyridyl)methyl] sulfinyl]-3H-imidazo[4,5-b]pyrid in-3-yl]carbonyl](methyl) amino]ethyl acetate, 2-[methyl[[2-[[[3-methyl-4-(2,2,2-trifluoroethoxy)-2-pyridyl]methyl]sulfinyl]-1H-benzimidazol-1-yl]carbonyl]amino]ethyl acetate, ethyl 2-[[[5-methoxy-2-[[(4-methoxy-3,5-dimethyl-2-pyridyl) methyl]sulfinyl]-1H-benzimidazol-1-yl]carbonyl](methyl) amino]ethyl carbonate, ethyl 2-[[[(S)-5-methoxy-2-[[(4-methoxy-3,5-dimethyl-2-pyridyl)methyl]sulfinyl]-1H-benzimida zol-1-yl]carbonyl](methyl)amino]ethyl carbonate, ethyl 2-[[[2-[[[4-(3-methoxypropoxy)-3-methyl-2-pyridyl]methyl]sulfinyl]-1H-benzimidazol-1-yl]carbonyl] (methyl)amino]ethyl carbonate, and 2-[[[5-(difluoromethoxy)-2-[[(3,4-dimethoxy-2-pyridyl)methyl]sulfinyl]-1H-benzimidazol-1-yl]c arbonyl](methyl)amino]ethyl ethyl carbonate, or a salt thereof.

11. A production method of a compound of claim 1, which comprises (1) condensing a compound represented by the formula (III):

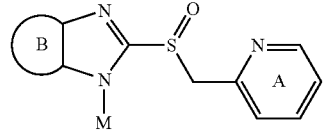

(III)

wherein
ring A is a pyridine ring optionally having substituents selected from
(1) $C_{1-6}$ alkyl group, and
(2) $C_{1-6}$ alkoxy group optionally substituted by substituent(s) selected from halogen atom(s) and $C_{1-6}$ alkoxy group,
ring B is a benzene ring optionally having substituents selected from $C_{1-6}$ alkoxy group optionally having halogen atom(s), and
M is a hydrogen atom, a metal cation or a quaternary ammonium ion, or a salt thereof, with a compound represented by the formula (IV):

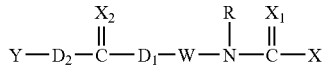

(IV)

wherein
X is a leaving group,
$X_1$ and $X_2$ are each an oxygen atom or a sulfur atom,
W is $C_{1-6}$ alkylene group optionally having substituents selected from $C_{1-6}$ alkyl-carbonyloxy and ethoxycarbonyloxy, or a divalent group of the formula:

—$W_1$-Z-$W_2$— wherein $W_1$ and $W_2$ are each a $C_{1-6}$ alkylene group or a bond, Z is $C_{6-14}$ arene, an oxygen atom, $SO_n$ wherein n is 0, 1 or 2, or >N-E wherein E is a hydrogen atom, a lower alkanoyl group, a lower alkoxycarbonyl group, an aralkyloxycarbonyl group, a thiocarbamoyl group, a lower alkylsulfinyl group, a lower alkylsulfonyl group, a sulfamoyl group, a mono-lower alkylsulfamoyl group, a di-lower alkylsulfamoyl group, an arylsulfamoyl group, an arylsulfinyl group, an arylsulfonyl group, an arylcarbonyl group or a carbamoyl group, and when Z is an oxygen atom, $SO_n$ or >N-E, $W_1$ and $W_2$ are each $C_{1-6}$ alkylene group,
R is a group selected from
(1) $C_{1-6}$ alkyl group optionally substituted by $C_{1-6}$ alkyl-carbonyloxy,
(2) $C_{3-10}$ cycloalkyl group, and
(3) $C_{6-14}$ aryl group optionally substituted by a group represented by —CO—$NR^2R^3$ (wherein $R^2$ and $R^3$ are each $C_{1-6}$ alkyl group),
$D_1$ is an oxygen atom, a sulfur atom, or >$NR_1$,
$D_2$ is a bond, an oxygen atom, a sulfur atom, or >$NR_1$ wherein each $R_1$ is independently $C_{1-6}$alkyl group, and
Y is a group selected from
(1) $C_{1-6}$alkyl group optionally having substituent(s) selected from $C_{1-6}$ alkoxy group, ethoxycarbonyloxy group, $C_{6-14}$ aryl group and a group represented by —$NR^2R^3$ (wherein $R^2$ and $R^3$ are each $C_{1-6}$ alkyl group),
(2) $C_{3-10}$ cycloalkyl group,
(3) $C_{6-14}$ aryl group optionally having substituent(s) selected from (i) halogen atom and (ii) $C_{1-6}$ alkoxy group optionally having halogen atom(s), and (4) tetrahydropyran, or
a salt thereof.

12. A pharmaceutical composition comprising a compound of claim 1 together with a pharmaceutically acceptable carrier.

13. A method for the treatment of peptic ulcer in an animal, which comprises administering an effective amount of a compound of claim 1 to the animal.

* * * * *